United States Patent
Miyamoto et al.

(10) Patent No.: US 8,022,979 B2
(45) Date of Patent: Sep. 20, 2011

(54) ENDOSCOPE SYSTEM

(75) Inventors: Shinichi Miyamoto, Tokyo (JP);
Takayuki Kameya, Tokyo (JP);
Katsushi Watanabe, Tokyo (JP);
Kazutaka Matsumoto, Tokyo (JP);
Takeaki Nakamura, Tokyo (JP)

(73) Assignee: Olympus Corporation, Tokyo (JP)

( * ) Notice: Subject to any disclaimer, the term of this patent is extended or adjusted under 35 U.S.C. 154(b) by 1437 days.

(21) Appl. No.: 11/503,708

(22) Filed: Aug. 14, 2006

(65) Prior Publication Data

US 2007/0188604 A1 Aug. 16, 2007

Related U.S. Application Data

(63) Continuation of application No. PCT/JP2005/002284, filed on Feb. 15, 2005.

(30) Foreign Application Priority Data

| Feb. 16, 2004 | (JP) | 2004-038718 |
| Feb. 25, 2004 | (JP) | 2004-049248 |
| Mar. 24, 2004 | (JP) | P2004-086835 |
| Mar. 24, 2004 | (JP) | P2004-086836 |
| Jun. 7, 2004 | (JP) | P2004-168309 |

(51) Int. Cl.
*A62B 1/04* (2006.01)
*A61B 1/04* (2006.01)

(52) U.S. Cl. .......... 348/65; 600/109

(58) Field of Classification Search ............ 348/65; 600/109, 114, 160, 179, 188
See application file for complete search history.

(56) References Cited

U.S. PATENT DOCUMENTS

| 5,879,289 | A | * | 3/1999 | Yarush et al. | 600/179 |
| 5,928,137 | A | * | 7/1999 | Green | 600/160 |
| 6,387,043 | B1 | * | 5/2002 | Yoon | 600/109 |
| 6,652,453 | B2 | * | 11/2003 | Smith et al. | 600/188 |
| 6,830,545 | B2 | * | 12/2004 | Bendall | 600/114 |
| 7,048,686 | B2 | * | 5/2006 | Kameya et al. | 600/179 |
| 2002/0022769 | A1 | | 2/2002 | Smith et al. | |
| 2003/0078477 | A1 | | 4/2003 | Kang et al. | |

FOREIGN PATENT DOCUMENTS

| CN | 1415267 A | 5/2003 |
| JP | H10-127575 | 5/1998 |
| JP | H11-9548 | 1/1999 |
| JP | 2000-116599 | 4/2000 |
| JP | 2000-171729 | 6/2000 |
| JP | 2000-189385 | 7/2000 |
| JP | 2001-330784 | 11/2001 |

OTHER PUBLICATIONS

English language abstract of Japanese Patent Application Publication No. 2000-189385.
English language abstract of Japanese Patent Application Publication No. 2001-330784.

* cited by examiner

*Primary Examiner* — Gims Philippe
(74) *Attorney, Agent, or Firm* — Scully, Scott, Murphy & Presser, P.C.

(57) ABSTRACT

The endoscope system of the present invention includes: an endoscope that has an image pickup device that picks up an observation image of a test object; an image display unit that converts image pickup signals that have been sent from the image pickup device into images and then displays these images; a first mounting portion that is provided in an operating section of the endoscope and on which the image display unit is mounted; and a second mounting portion that is provided in the operating section of the endoscope and on which the image display unit is mounted in a different position from that of the first mounting portion.

13 Claims, 46 Drawing Sheets

ENDOSCOPE SYSTEM

PRIORITY CLAIM

This application is continuation application of a PCT Application No. PCT/JP2005/002284, filed on Feb. 15, 2005, entitled "ENDOSCOPE SYSTEM" whose priority is claimed on Japanese Patent Application No. 2004-86835 and Japanese Patent Application No. 2004-86836, filed Mar. 24, 2004, Japanese Patent Application No. 2004-168309, filed Jun. 7, 2004, Japanese Patent Application No. 2004-38718, filed Feb. 16, 2004, and Japanese Patent Application No. 2004-49248, filed Feb. 25, 2004, the contents of which are incorporated herein by reference.

BACKGROUND OF THE INVENTION

1. Field of the Invention

The present invention relates to an endoscope system and, in particular, to a portable endoscope system that incorporates a small image display device.

2. Description of Related Art

In endoscope systems that are widely used in medical and industrial fields, it is common for a fixed television monitor to be left permanently connected via a cable to an eyepiece portion, and for an image obtained by the endoscope to be formed on a light receiving portion of an image pickup element such as a CCD. This formed image is then converted into a signal and the image in the form of a signal is supplied via a cable to a television monitor in a separate location. The signal is then reconverted into an image and displayed on the screen of this television monitor.

Endoscope systems have also been proposed (for example, refer to Japanese Patent Application, First Publication, No. H10-127575, Japanese Patent Application, First Publication, No. H11-9548, Japanese Patent Application, First Publication, No. 2000-116599, and Japanese Patent Application, First Publication, No. 2000-171729) in which a light source apparatus, an image display unit such as a miniature liquid crystal monitor, and a battery that drives the light source, image pickup elements, and the liquid crystal monitor are incorporated in an endoscope.

SUMMARY OF THE INVENTION

The endoscope system according to a first aspect of the present invention, includes: an endoscope that has an image pickup device that picks up an observation image of a test object; an image display unit that converts image pickup signals that have been sent from the image pickup device into images and then displays these images; a first mounting portion that is provided in an operating section of the endoscope and on which the image display unit is mounted; and a second mounting portion that is provided in the operating section of the endoscope and on which the image display unit is mounted in a different position from that of the first mounting portion.

In the endoscope system of the present invention, it may be arranged such that there are provided: a first output terminal that is provided on the first mounting portion and that outputs image pickup signals that have been sent from the image pickup device; a second output terminal that is provided on the second mounting portion and that outputs image pickup signals that have been sent from the image pickup device; and an input terminal that is provided on the image display unit and, when the image display unit is mounted at the first mounting portion, is connected to the first output terminal and inputs the image pickup signals into the image display unit, and, when the image display unit is mounted at the second mounting portion, is connected to the second output terminal and inputs the image pickup signals into the image display unit.

The endoscope system according to a second aspect of the present invention, includes: an endoscope that has an image pickup device that picks up an observation image of a test object; an image display unit that converts image pickup signals that have been sent from the image pickup device into images and then displays these images; and a supporting portion that is provided on the operating section of the endoscope and that supports the image display unit such that it can be opened up from and shut against the operating section.

In the endoscope system of the present invention, it may be arranged such that the supporting portion is provided with: a first rotation shaft that extends in a direction that intersects a side surface of the operating section and that forms a center of rotation when the image display unit is rotated; and a second rotation shaft that extends in another direction that is perpendicular to the first rotation shaft and that forms a center of rotation when the image display unit is rotated in another direction.

In the endoscope system of the present invention, it may be arranged such that the supporting portion supports the image display unit such that it can be housed within a recessed portion that is provided in an outer circumferential surface of the operating section.

In the endoscope system of the present invention, it may be arranged such that the first rotation shaft and the second rotation shaft are each located away from the central axis of the image display unit.

The endoscope system according to a third aspect of the present invention, includes: an endoscope that is provided with an image pickup device that picks up an image of a test object and a gripping portion that is formed in a longitudinal direction of the endoscope; and an image display unit that is formed integrally with the endoscope and that converts pictures of the test object that have been obtained by the image pickup device into images and then displays these images, wherein the image display unit is mounted so as to protrude from a side portion of the endoscope such that, when the gripping portion is gripped by a hand whose thumb is positioned uppermost, the image display unit is positioned above the fingers of the hand that is gripping the gripping portion excluding the thumb.

In the endoscope system of the present invention, it may be arranged such that there is provided a light source apparatus that is formed integrally with the endoscope and that protrudes in a symmetrically opposite direction from the image display unit with a longitudinal axis of the endoscope sandwiched in between.

The endoscope system according to a fourth aspect of the present invention, includes: an endoscope that is provided with an image pickup device that picks up an image of a test object and an operating section that operates the endoscope; a finger piece portion that is provided so as to intersect an axis n the longitudinal direction of the operating section; and an image display unit that is formed integrally with the finger piece portion and that converts pictures of the test object that have been obtained by the image pickup device into images and then displays these images.

In the endoscope system of the present invention, it is preferable if a rotatable operating lever is provided in the operating section, and the image display unit is provided at substantially the same position as a rotation shaft of this operating lever.

The endoscope system according to a fifth aspect of the present invention, includes: an insertion portion that can be inserted inside a body cavity of a test object; an observation image acquisition portion that acquires an observation image of the interior of the body cavity from a distal end side of the insertion portion; an operating section that is connected to a base end portion of the insertion portion; an observation portion that is provided in the operating section and that makes it possible to observe the observation images that have been acquired by the observation image acquisition portion; and three setting down portions that are arranged in a triangle extending across at least one of the operating section and the observation portion.

In the endoscope system of the present invention, it may be arranged such that at least one of the setting down portions is formed by a connector component that is used for connecting an external cable and is provided so as to protrude from the observation portion or the operating section.

The endoscope system according to a sixth aspect of the present invention, includes: an insertion portion that can be inserted inside a body cavity of a test object; an observation image acquisition portion that acquires an observation image of the interior of the body cavity from a distal end side of the insertion portion; an image pickup device that picks up the observation images; an image display unit that includes a display screen that displays observation images based on image pickup signals from the image pickup device; an operating section that is provided with a gripping portion and that is connected to a base end portion of the insertion portion; and a supporting portion that is provided in the operating section and rotatably supports the image display unit, wherein the display screen can be rotated around an axis that intersects a longitudinal direction of the gripping portion.

In the endoscope system of the present invention, it may be arranged such that the operating section is provided with an operating component that controls movements of the insertion portion, and, in the gripping portion, the operating component can be operated by an operator when the operator is gripping the gripping portion, and, in the image display unit, when the operator is gripping the gripping portion the display screen can be rotated so as to face towards the operator.

In the endoscope system of the present invention, it may be arranged such that the supporting portion is provided with: a first rotation supporting portion that is provided on the operating section; a second rotation supporting portion that is provided on the image display unit; and an arm component that is rotatably linked to both the first rotation supporting portion and the second rotation supporting portion.

DETAILED DESCRIPTION OF THE INVENTION

First Embodiment

Figure 1:
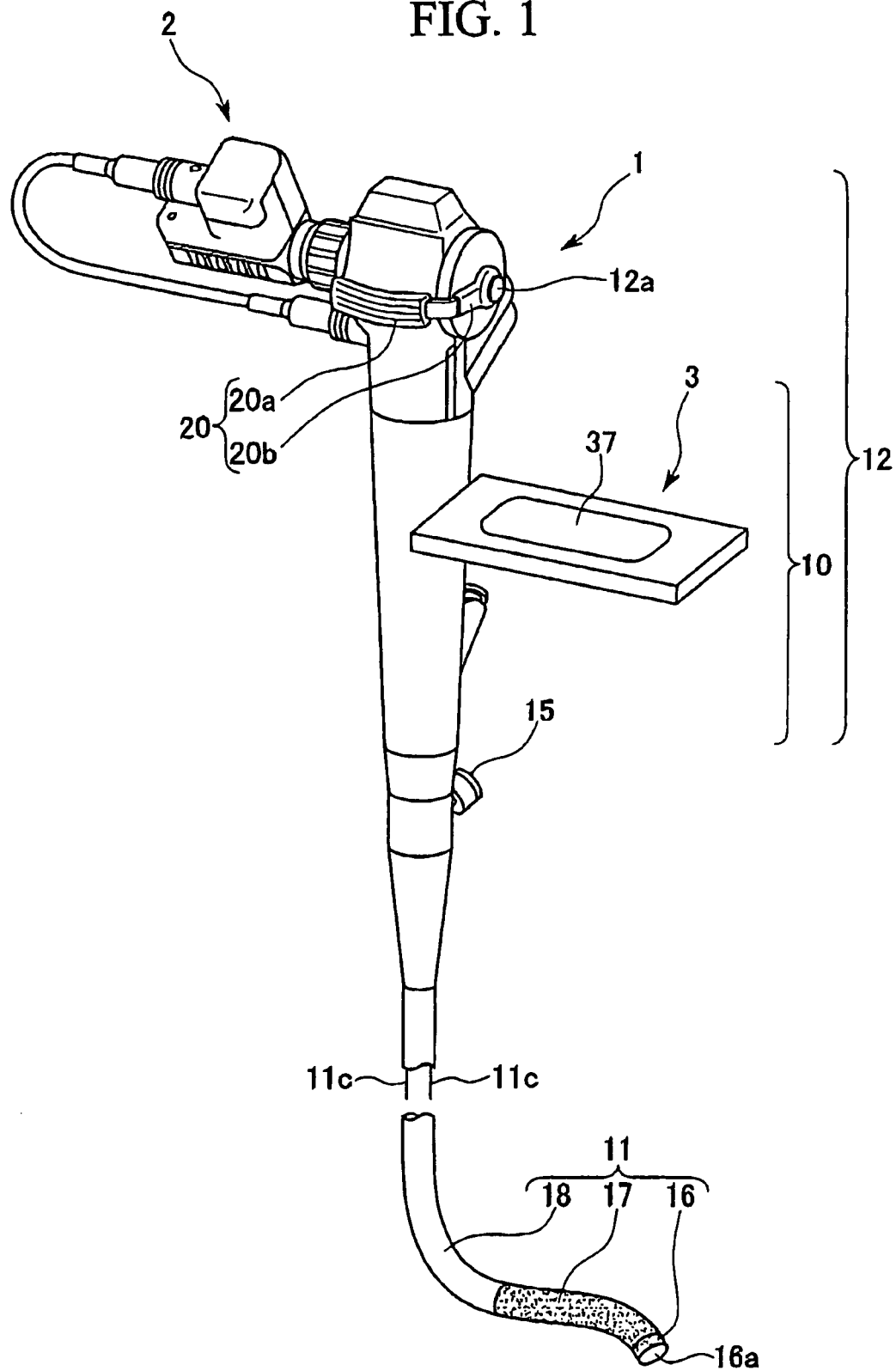
FIG. 1 is a perspective view showing a first embodiment of the endoscope system of the present invention.
Figure 2:
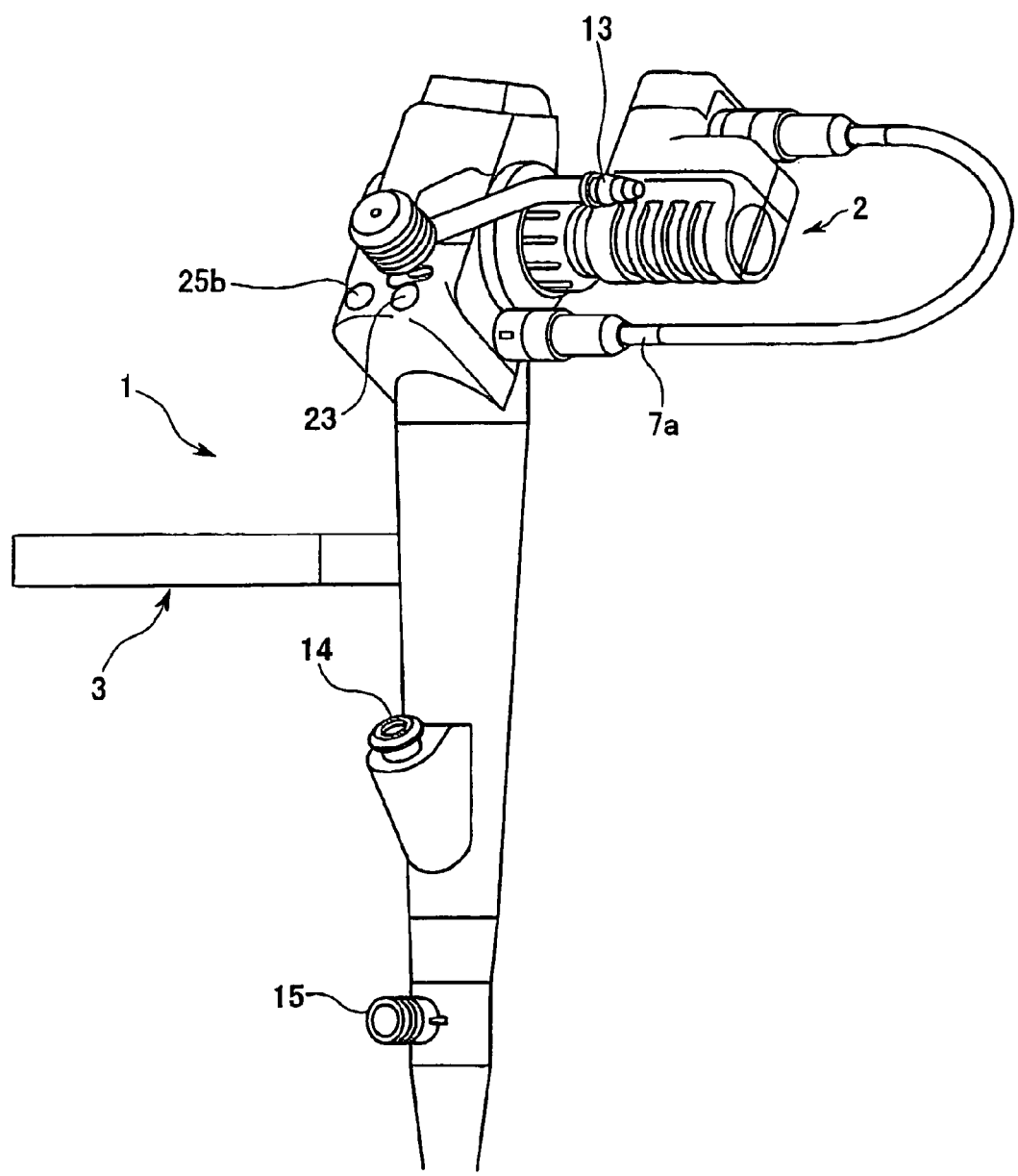
FIG. 2 is a perspective view looking from a different direction from that in FIG. 1 of the endoscope system of the first embodiment.
Figure 3:
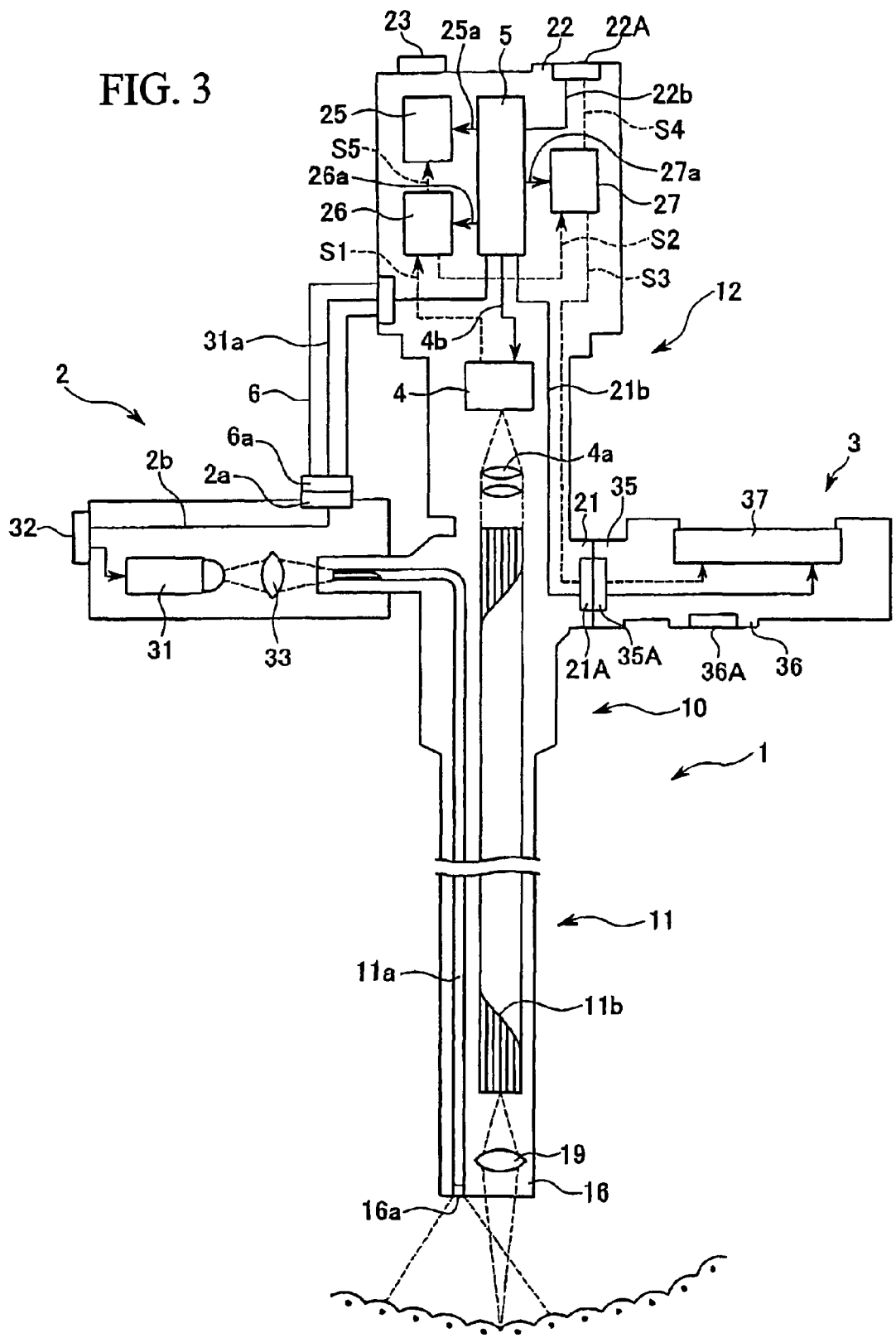
FIG. 3 is a schematic view showing the internal structure of the endoscope system of the first embodiment.

The first embodiment of the endoscope system of the present invention will now be described using FIG. 1 through FIG. 5.

As is shown in FIG. 1 through FIG. 4, the principal component elements of the endoscope system of the present embodiment are an endoscope 1, a light source apparatus 2 that generates illumination light for illuminating an object, and an image display unit 3 that creates an image from the image of the object obtained by the endoscope 1 and displays this created image.

The endoscope 1 is provided with an insertion section 11 whose distal end is inserted into an observation position, and an operating section 12 that is used to bend the distal end of the insertion section 11. In addition, the endoscope 1 is also provided with an image pickup element (i.e., image pickup device) 4 such as a CCD or the like that receives light from an image (i.e., from light) that is guided by an image guide 11b (described below), and a condenser lens 4a that forms an image on the light receiving portion of the image pickup device 4. The insertion section 11 is formed having a flexible elongated configuration and is connected to one end of the operating section 12. The insertion section 11 is provided with a hard distal end portion 16 that is located at a distal end thereof, a bending portion 17 that continues from the distal end portion 16, and a flexible portion 18 that continues from the bending portion 17 and is connected to the operating section 12. The distal end portion 16 is provided with an objective lens 19 that forms an image from reflected light that is reflected from the object which has been illuminated by the illumination light, and an illumination window 16a through which the illumination light is irradiated. A light guide 11a that guides illumination light from the light source apparatus 2 to the distal end portion 16, and an image guide 11b that guides images formed on the objective lens 19 to the image pickup element 4 are incorporated in the bending portion 17 and flexible portion 18. Note that, in some cases, the image pickup element 4 may be provided in the distal end portion 16 of the insertion portion 11.

The operating section 12 is provided with a gripping portion 10 that an operator uses to grip the endoscope 1, and a bending operation lever 20 that is used to bend the bending portion 17 in a desired direction via two wires 11c that pass through the insertion portion 11. The gripping portion 10 is formed in a rod shape that allows it to be gripped by wrapping the thumb and the other fingers around it. The gripping portion 10 is provided with a suction cap 13 that is used for sectioning liquids such as body fluids and the like, a forceps insertion aperture 14 that is used for inserting treatment tools such as forceps and the like, and an aeration mouthpiece 15 that is used for feeding air into the interior of the endoscope 1 during inspections to check for leakages in the endoscope 1. A suction apparatus is connected by a tube (not shown) to the suction cap 13 and body fluids and the like can be suctioned through the suction cap 13 by operating the suction apparatus. An air supply apparatus is connected by a tube (not shown) to the aeration mouthpiece 15 and, by operating the air supply apparatus, air can be supplied from the aeration mouthpiece 15 to the endoscope 1 so that a leakage inspection of the interior of the endoscope 1 can be performed.

First and second mounting portions 21 and 22 on which the image display unit 3 is mounted are provided in the operating section 12. The first mounting portion 21 is positioned at the other end of the operating section 12, while the second mounting portion 22 is positioned on a side surface of the operating section 12. The operating section 12 is also provided with a startup switch 23 that starts up the endoscope system, and an image recording switch 25b that causes images that are displayed on the image display unit 3 to be recorded on an image recording device 25 (described below).

A first output terminal 21A is provided on the first mounting portion 21. The first output terminal 21A is connected to either an input terminal 35A or an input terminal 36A that are provided on mounting portions 35 and 36 of the image display unit 3, and supplies image signals and power to the image display unit 3. A second output terminal 22A is provided on the second mounting portion 22. The second output terminal 22A is also connected to either the input terminal 35A or the input terminal 36A that are provided on the mounting portions 35 and 36 of the image display unit 3, and supplies image signals and power to the image display unit 3.

Note that, in the present embodiment, the first and second mounting portions 21 and 22 are provided in two different locations on the operating section 12, however, the mounting portions are not limited to being provided in two locations and may be provided in three or more locations.

Inside the operating section 12 are provided the image recording device 25 that records images of an object, an image pickup element control circuit 26 that converts images of an object that have been picked up by the image pickup element 4 into signals and then outputs these, and a display element control circuit 27 that converts signals output from the image pickup element control circuit 26 into images and then displays these on a display element 37 of the image display unit 3. In addition, a replaceable battery 5 that supplies power respectively to the light source apparatus 2, the image pickup element 4, and the image display unit 3 is fitted inside the operating section 12. The battery 5 is a secondary battery that can be used by being repeatedly recharged. Inside the image recording device 25 a memory card, for example, is employed as a recording medium. This recording medium is fitted inside the endoscope 1 such that it can be replaced.

The bending operation lever 20 is provided adjacent to the gripping portion 10 such that it can be operated by the fingers of the hand gripping the gripping section 10. The bending operation lever 20 is formed in an L shape that is made up of a distal end portion 20a that is operated by the thick part of the thumb holding the gripping portion 10, and a base end portion 20b that is connected to one end of the distal end portion 20a, and is axially supported by the base end portion 20b on a shaft 12a, which is provided on the operating section 12, such that it can swing vertically. In the bending operation lever 20, the bending portion 17 can be made to bend freely by pushing or pulling the distal end portion 20a thereof using the thumb such that tensile force is applied to one of the wires 11c while thrust force is applied to the other of the wires 11c.

The light source apparatus 2 is provided with a light source lamp 31, a finger switch 32 that an operator uses to turn on or turn off the light source lamp 31 as desired, and a condenser lens 33 that condenses illumination light generated by the light source lamp 31. A connector 2a to which a power cable 6 (described below) can be removably connected is also provided in the light source apparatus 2. The light source lamp 31, the finger switch 32, and the connector 2a are connected in series by a power supply line 2b that is built into the power supply apparatus 2.

Illumination light that is generated by the light source lamp 31 is condensed by the condenser lens 33, guided by the light guide 11a, and is then emitted through the illumination window 16a so as to illuminate the interior of a body cavity.

The image display unit 3 is provided with a display element 37 such as an LCD that converts observed pictures of an object into images and then displays these. The two mounting portions 35 and 36 that can removably engage with the first mounting portion 21 or the second mounting portion 22 that are provided in the operating section 12 are provided in the image display unit 3.

The input terminal 35A is provided in the mounting portion 35. When the mounting portion 35 is engaged with either the first mounting portion 21 or the second mounting portion 22 that are provided in the operating section 12, the input terminal 35A is connected to either the first output terminal 21A or the second output terminal 22A so that power that is supplied from the battery 5 is input to the display element 37 and image signals that are supplied from the display element control circuit 27 are input into the display element 37.

The input terminal 36A is provided in the mounting portion 36. When the mounting portion 36 is engaged with either the first mounting portion 21 or the second mounting portion 22 that are provided in the operating section 12, the input terminal 36A is connected to either the first output terminal 21A or the second output terminal 22A so that power that is supplied from the battery 5 is input to the display element 37 and image signals that are supplied from the display element control circuit 27 are input into the display element 37.

Note that, in the present embodiment, the mounting portions 35 and 36 are provided in two locations on the image display unit 3, however, the mounting portions of the image display unit are not limited to being provided in two locations and may be provided in one location or in three or more locations.

The light source apparatus 2 is connected by the power supply cable 6 that encloses a power supply line 31a (described below). A base end of the power supply cable 6 is fixed to the endoscope 1 side, while a distal end thereof is provided with a connector 6a. The connector 6a is removably connected to the connector 2a of the power supply apparatus 2.

A power supply line 4b that supplies power to the image pickup element 4 is provided between the image pickup element 4 and the battery 5, while the power supply line 31a that supplies power to the light source lamp 31 is provided between the light source apparatus 2 and the battery 5, and a power supply line 25a is provided between the image recording device 25 and the battery 5. In the same way, a power supply line 21b that supplies power to the display element 37 when either one of the input terminals 35A or 36A of the image display unit 3 is connected to the first output terminal 21A is provided between the first output terminal 21 and the battery 5, and a power supply line 22b that supplies power to the display element 37 when either one of the input terminals 35A or 36A of the image display unit 3 is connected to the second output terminal 22A is provided between the second output terminal 22A and the battery 5. Moreover, a power supply line 26a that supplies power to the image pickup element control circuit 26 is provided between the image pickup element control circuit 26 and the battery 5, while a power supply line 27a that supplies power to the display element control circuit 27 is provided between the display element control circuit 27 and the battery 5.

A signal line S1 that transmits image signals acquired by the image pickup element 4 to the image pickup element control circuit 26 is provided between the image pickup element 4 and the image pickup element control circuit 26, while a signal line S2 that transmits image signals that have been input into the image pickup element control circuit 26 to the display element control circuit 27 is provided between the image pickup element control circuit 26 and the display element control circuit 27. In addition, a signal line S3 that inputs image signals into the display element 37 when either one of the input terminals 35A and 36A of the image display unit 3 is connected to the first output terminal 21A is provided between the display element control circuit 27 and the first output terminal 21, while a signal line S4 that inputs image signals into the display element 37 when either one of the input terminals 35A and 36A of the image display unit 3 is connected to the second output terminal 22A is provided between the display element control circuit 27 and the second output terminal 22A. Furthermore, a signal line SS that transmits image signals that have been input into the image pickup element control circuit 26 to the image recording device 25 is provided between the image recording device 25 and the image pickup element control circuit 26.

Figure 4:
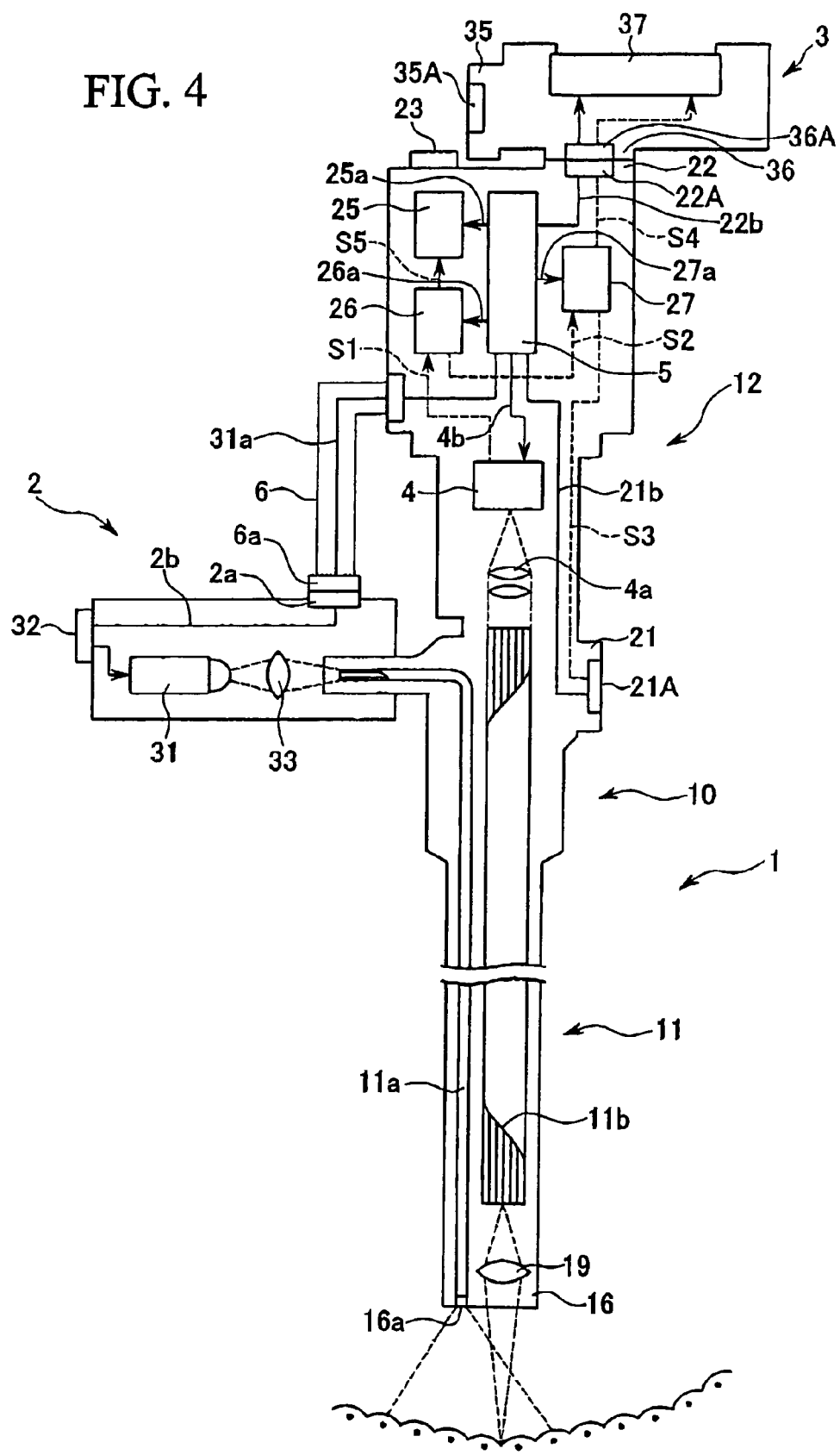
FIG. 4 is a schematic view showing with the internal structure of the endoscope system of the first embodiment.

Note that, in the present embodiment, the first mounting portion 21 is engaged with the mounting portion 35 of the image display unit 3, however, as is shown in FIG. 4, it is also possible for the second mounting portion 22 to be engaged with the mounting portion 36. It is also possible to engage the first mounting portion 21 with the mounting portion 36, and to engage the second mounting portion 22 with the mounting portion 35, Namely, the image display unit 3 can be set in any position desired by the operator.

In an endoscope system having the above described structure, the image display unit 3 can be removably fitted to the first mounting portion 21 that is provided on a side surface of the operating section 12 or to the second mounting portion 22 that is provided on a top surface of the operating section 12. When an operator alters the way they hold the gripping portion 10 in order to suit the operation or examination being performed, the operator selects whichever of the first mounting portion 21 or the second mounting portion 22 is in a location that makes it easier to view the screen of the image display unit 3, and mounts the image display unit 3 in that mounting portion. As a result, irrespective of the way in which the operator is gripping the endoscope 1, it is always possible to obtain an excellent view of the image of the object that is displayed on the image display unit 3.

Moreover, because the mounting portion 35 is provided with the input terminal 35A, and the mounting portion 36 is provided with the input terminal 36A, and because the first mounting portion 21 is provided with the first output terminal 21A, and the second mounting portion 22 is provided with the second output terminal 22A, if either of the mounting portions 35 and 36 is engaged with either of the first and second mounting portions 21 and 22, then the output terminals and input terminals with which each is provided are connected and power and image signals are supplied to the image display unit 3. Accordingly, the image display unit can be easily engaged or disengaged without the endoscope 1 and image display unit having to be connected by a cable.

Note that the present invention is not limited to the above described embodiment and various modifications may be made thereto insofar as they do not depart from the spirit or scope of the present invention.

For example, it is also possible to provide a separate cable to connect the endoscope 1 and image display unit 3 without providing the output terminals and input terminals in the respective mounting portions, and to supply power and image signals via this cable.

Moreover, the endoscope system of the present embodiment has a structure in which the image recording device 25, the image pickup element control circuit 26, and the display element control circuit 27 are provided in the operating section 12, however, it is also possible for the endoscope system to have a structure in which the image recording device 25, the image pickup element control circuit 26, and the display element control circuit 27 are provided in the image display unit 3.

Figure 5:
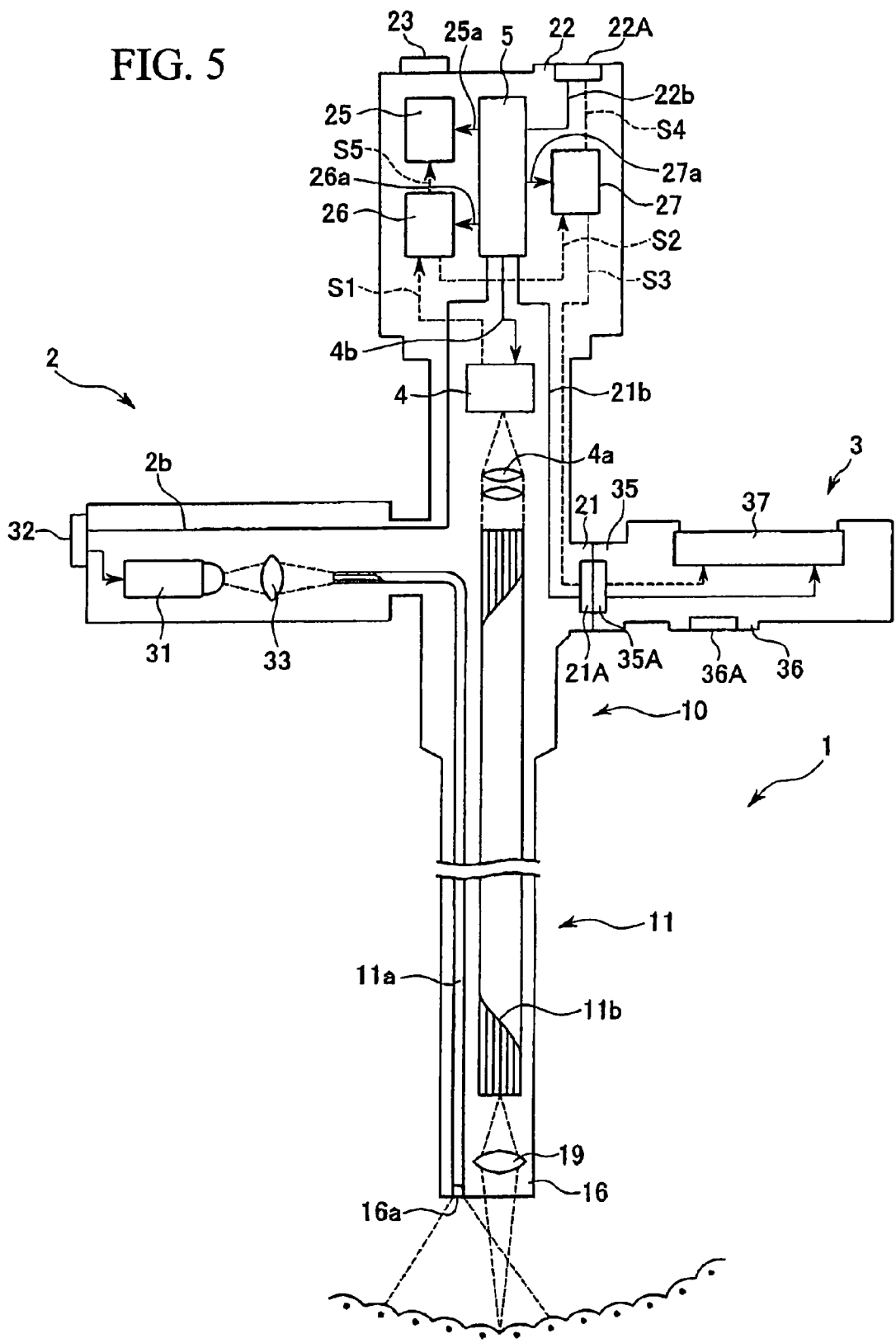
FIG. 5 is a schematic view showing the internal structure of an endoscope system to which the present invention can be applied in addition to the endoscope system of the first embodiment.
Figure 6:
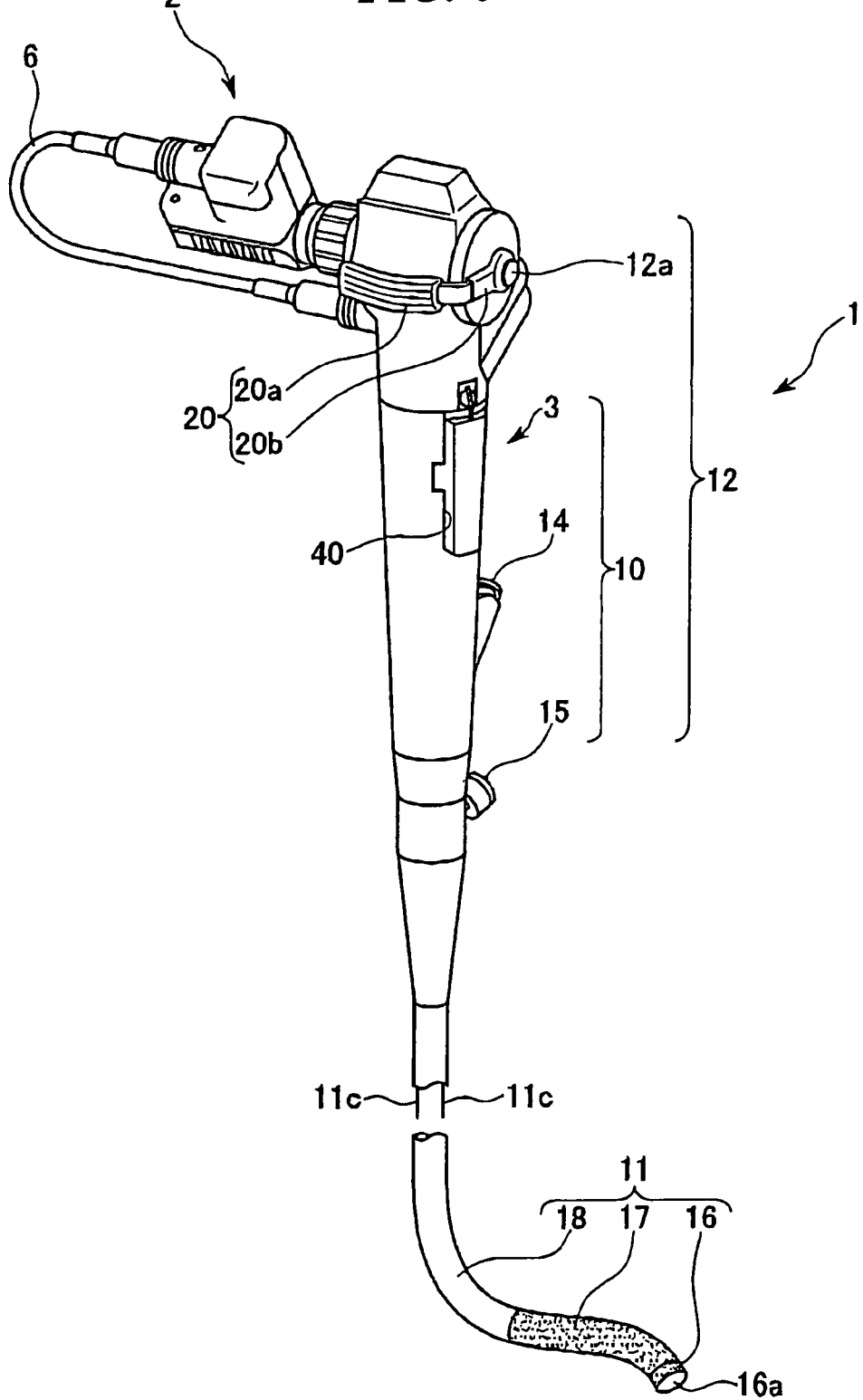
FIG. 6 is a perspective view showing an endoscope system of the second embodiment of the present invention.
Figure 7:
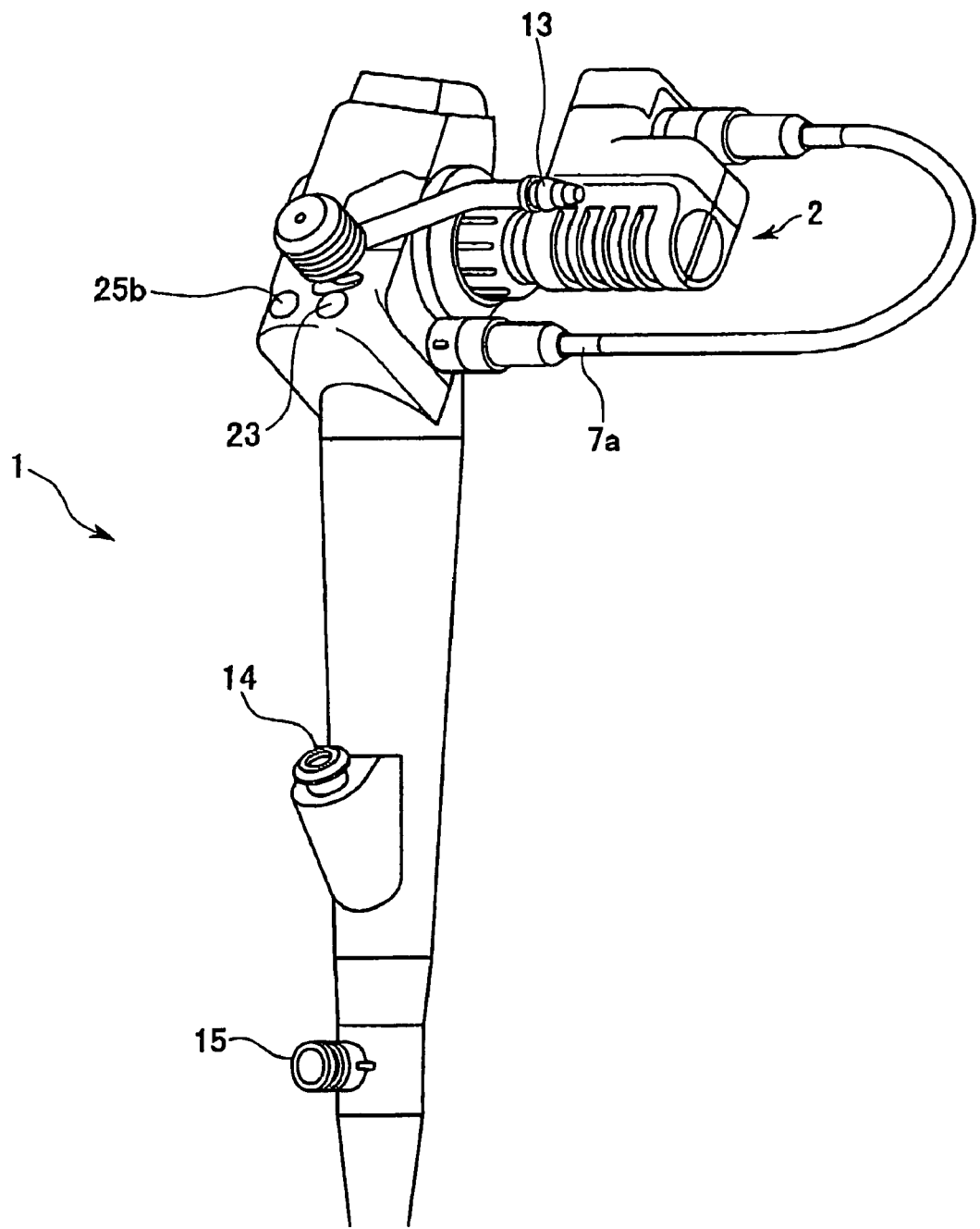
FIG. 7 is a perspective view looking from a different direction from that in FIG. 1 of the endoscope system of the second embodiment.
Figure 8:
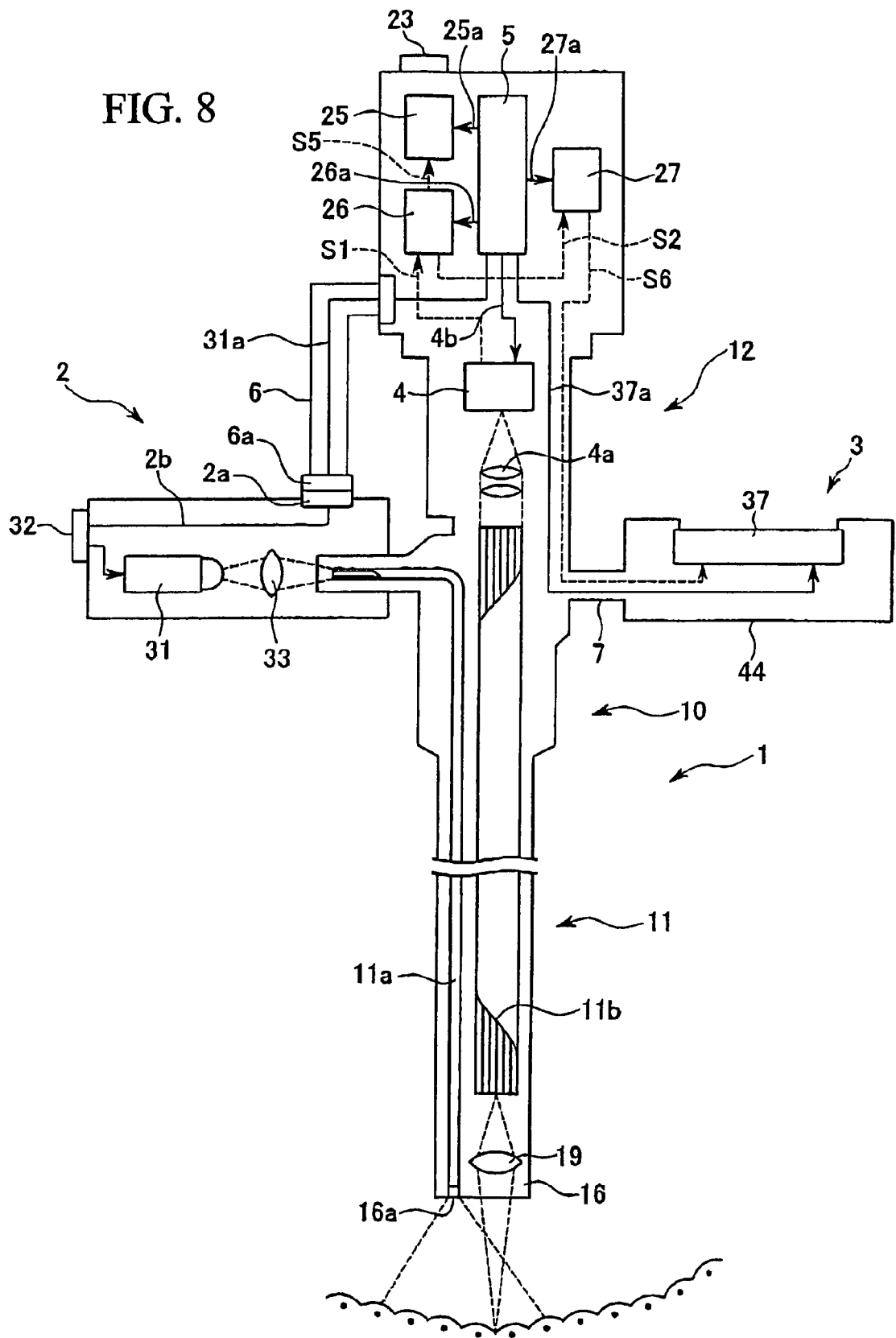
FIG. 8 is a schematic view showing the internal structure of the endoscope system of the second embodiment.

Furthermore, the endoscope system of the present embodiment has a structure in which the endoscope 1 and the power supply apparatus 2 are connected by the power supply cable 6, however, as is shown in FIG. 5, it is also possible for the endoscope system to have a structure in which, for example, the endoscope 1 and the power supply apparatus 2 are formed integrally Second Embodiment The second embodiment of the present invention will now be described with reference made to FIG. 6 through FIG. 12. Note that component elements that have previously been described in the above embodiment are given the same symbols and a description thereof is omitted.

As is shown in FIG. 6 through FIG. 10, the principal component elements of the endoscope system of the present embodiment are the endoscope 1, the light source apparatus 2, and the image display unit 3.

Figure 9:
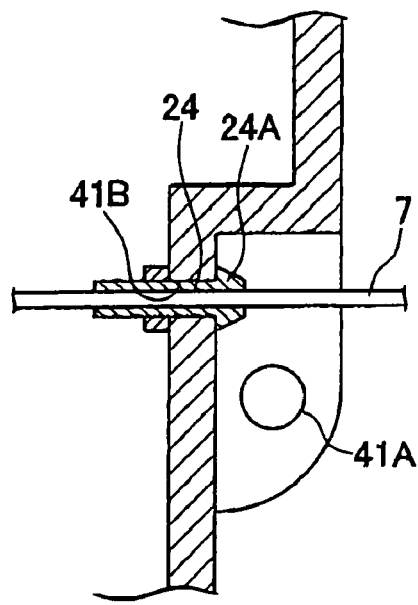
FIG. 9 is a cross-sectional view showing a first linking portion that is provided in the endoscope system of the second embodiment.
Figure 10:
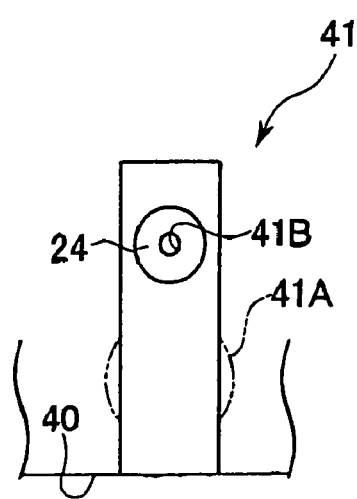
FIG. 10 is a plan view showing the first linking portion that is provided in the endoscope system of the second embodiment.

A recessed portion 40 in which the image display unit 3 can be housed is formed in the operating section 12 of the endoscope 1, and a first linking portion (i.e., supporting portion) 41 that supports the image display unit 3 is also provided in the operating section 12 of the endoscope 1. As is shown in FIG. 9 and FIG. 10, the first linking portion 41 is provided with a socket 41A that is a substantially ball-shaped hole and is a recessed portion that is formed adjacent to a recessed portion 21. A cable extraction hole 41B that enables a cable 7 (described below) to be extracted to the outside of the endoscope 1 is formed in the first linking portion 41. A filling component 24 is also provided in the space created between the cable extraction hole 41B and the cable 7. This filling component 24 is a hollow shaft-shaped component that has a flange portion 24A formed at one end thereof, and fits together with the housing of the endoscope 1.

Figure 11:
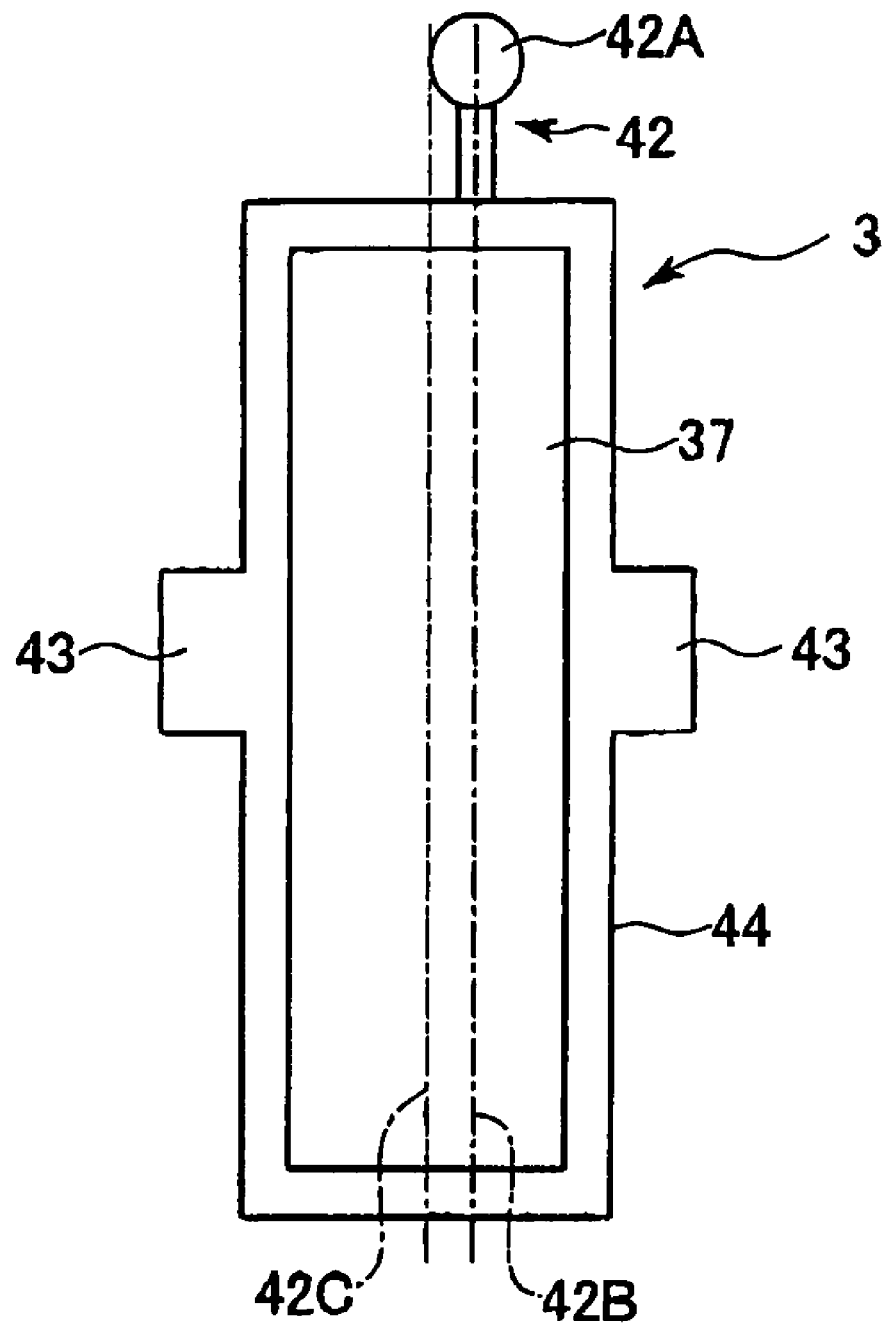
FIG. 11 is a plan view showing an image display unit that is provided in the endoscope system of the second embodiment.

The image display unit 3 is substantially shaped as a rectangular parallelepiped and is positioned so as to face an outer circumferential surface of the operating section 12 as a result of being engaged with the first linking portion 41, and is supported such that it is able to rotate relative to the endoscope 1. As is shown in FIG. 11, this image display unit 3 is provided with a second linking portion (i.e., supporting portion) 42 that is formed at one end thereof and that enables the image display unit 3 to be supported on the endoscope 1 when it links with the first linking portion 41, and with a pair of handhold portions 43 that protrude from two side surfaces of the image display unit 3, and an image display unit body 44 that has a display element 37 such as an LCD that converts observed pictures of an object into images and then displays these.

The second linking portion 42 is a shaft-shaped member and a ball-shaped stud 42A that is engaged in the socket 41A is provided at a distal end thereof. When this stud 42A is engaged with the socket 41A, what is known as a ball-joint connection is formed between the image display unit 3 and the endoscope 1. As a result, the image display unit 3 is able to swing freely relative to the endoscope 1. In addition, a central axis 42B of the second linking portion 42 is provided at a position away from a central axis 42C of the image display unit 3. As a result, the screen of the image display unit 3 can avoid being housed in the recessed portion 40 when it is facing the outside of the endoscope 1.

The handhold portions 43 are provided such that they can be operated by the thumb and middle finger of the gripping hand as it grips the gripping portions provided on the operating section 12. The angle of the image display unit 3 relative to the endoscope 1 can be adjusted using the thumb and thick part of the middle finger of the hand holding the gripping portion 10.

Figure 12:
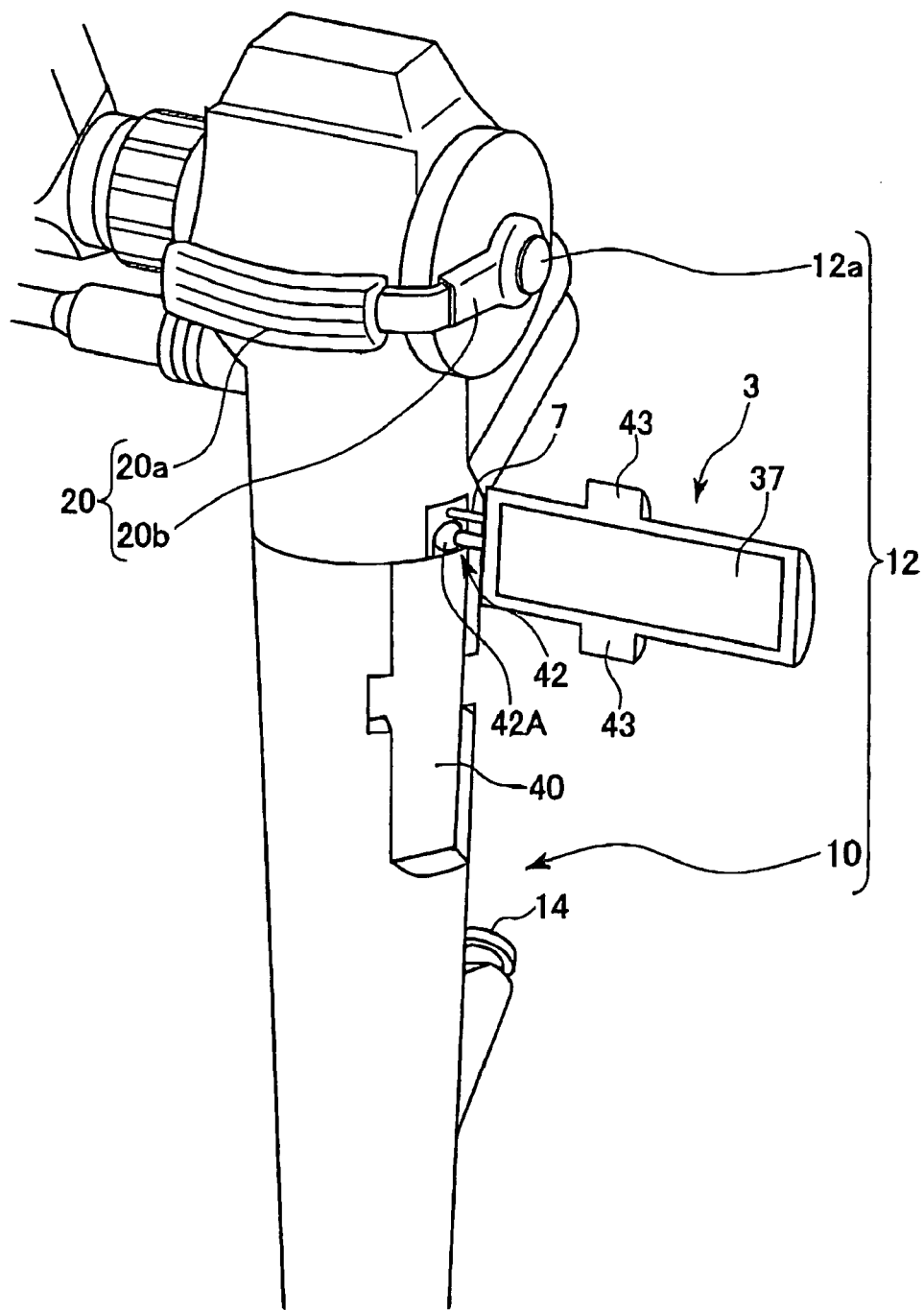
FIG. 12 is a perspective view showing the image display unit that is provided in the endoscope system of the second embodiment in an open state.

As is shown n FIG. 12, the image display unit 3 can be opened up from and shut inside the outer side surface of the operating section 12 as a result of the second linking portion 42 being engaged with the first linking portion 41. Accordingly, the orientation of the screen of the image display unit 3 can be adjusted.

A power supply line 37a that supplies power to the display element 4 is provided between the display element 37 and the battery 5. The image display unit 3 is connected by a cable that encloses the power supply line 37a and the signal line S3. A signal line S6 that transmits image signals that are input into the display element control circuit 27 to the display element 37 is also provided between the display element control circuit 27 and the display element 37.

In the endoscope system having the above described structure, the image display unit 3 is supported such that it can be opened and shut inside the outer side surface of the operating section 12 as a result of the second linking portion 42 being engaged with the first linking portion 41. If an operator finds it difficult to obtain an image of an object that is displayed on the image display unit 3 while operating the endoscope system, the operator can alter the orientation of the screen of the image display unit 3 using the fingers of the hand holding the operating section 12 so that the image of the object is easier to view. By employing this type of structure, it is possible to obtain an excellent view of an image of an object that is displayed on the image display unit 3 irrespective of the viewing angle of the display element 37. As a result, the operability of the endoscope system is improved.

At this time, because the first and second linking portions 41 and 42 form what is known as a ball joint, the image display unit 3 can be rotated in a variety of directions relative to the operating section 12 of the endoscope 1. Accordingly, the degree of freedom is increased when an operator wishes to adjust to the orientation of the screen of the image display unit 3. Furthermore, because the handhold portions 43 protrude from both side surfaces of the image display unit body 44, rating the image display unit 3 is simplified.

Moreover, because the recessed portion 40 is formed in the outer circumferential surface of the operating section 12, the image display unit 3 is housed inside the recessed portion 40 when it is shut inside the operating section 12. As a result, a reduction in the size of the endoscope system is achieved and the image display unit 3 can be stored with the image display unit 3 shut inside the operating section 12. Accordingly, not only is a reduction in the size of the endoscope system achieved, but the portability thereof is also improved.

Furthermore, because the central axis 42C of the image display unit 3 is provided at a position away from the central axis 42B of the second linking portion 42, it is possible to prevent the image display unit 3 being housed inside the recessed portion 40 while the display screen thereof is still facing towards the outside of the endoscope 1.

Third Embodiment

The third embodiment of the present invention will now be described with reference made to FIG. 13 through FIG. 19.

Note that component elements that have previously been described in the above embodiments are given the same symbols and a description thereof is omitted.

Figure 13:
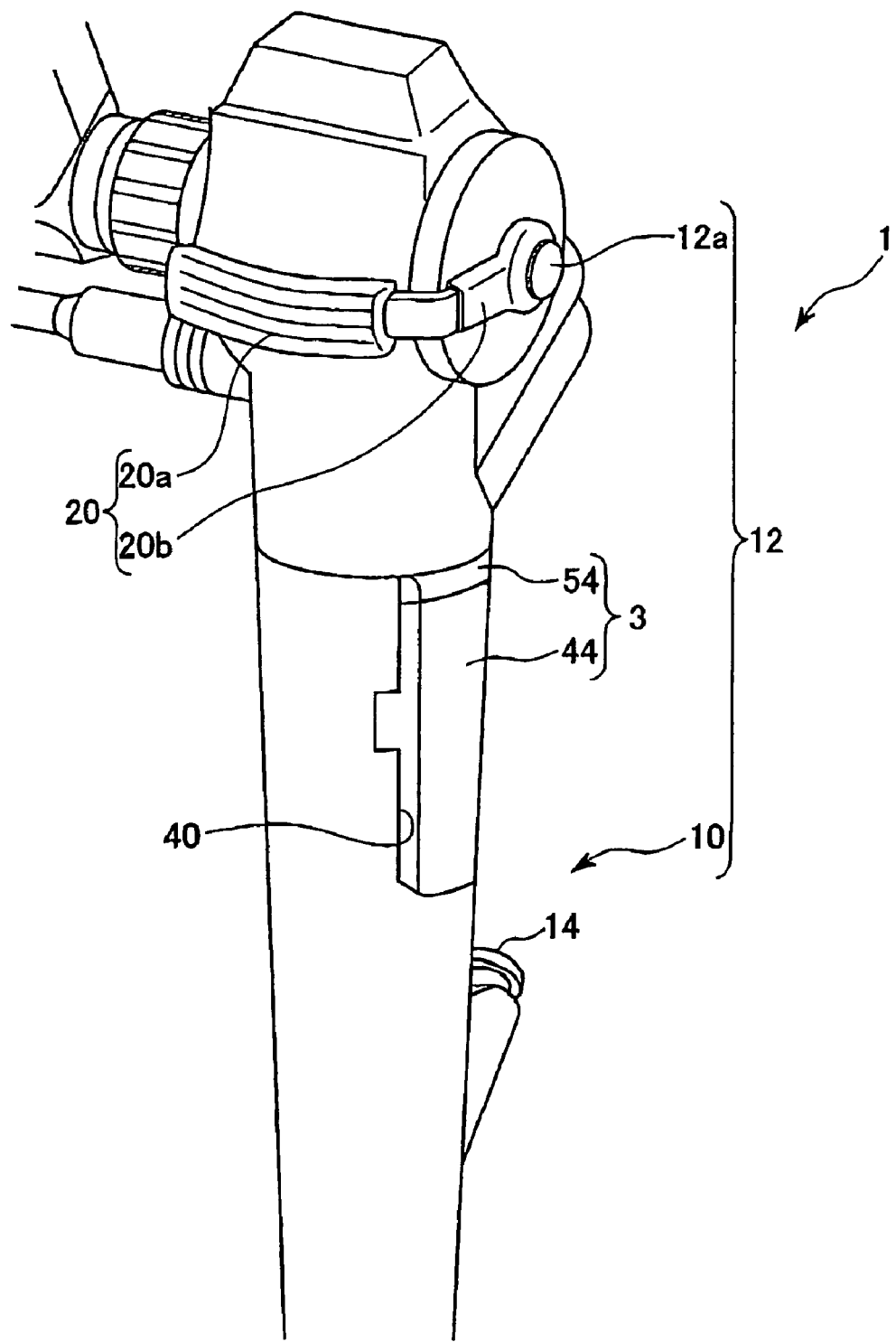
FIG. 13 is a perspective view showing an endoscope system of the third embodiment of the present invention.

In the endoscope system in the first embodiment, the image display unit 3 is supported by what is known as a ball joint. In contrast, in the endoscope system of the second embodiment, as is shown in FIG. 13, the image display unit 3 is supported by a rotation mechanism (i.e., a supporting portion) 54 that enables the image display unit 3 to be rotated around the endoscope 1.

Figure 14:
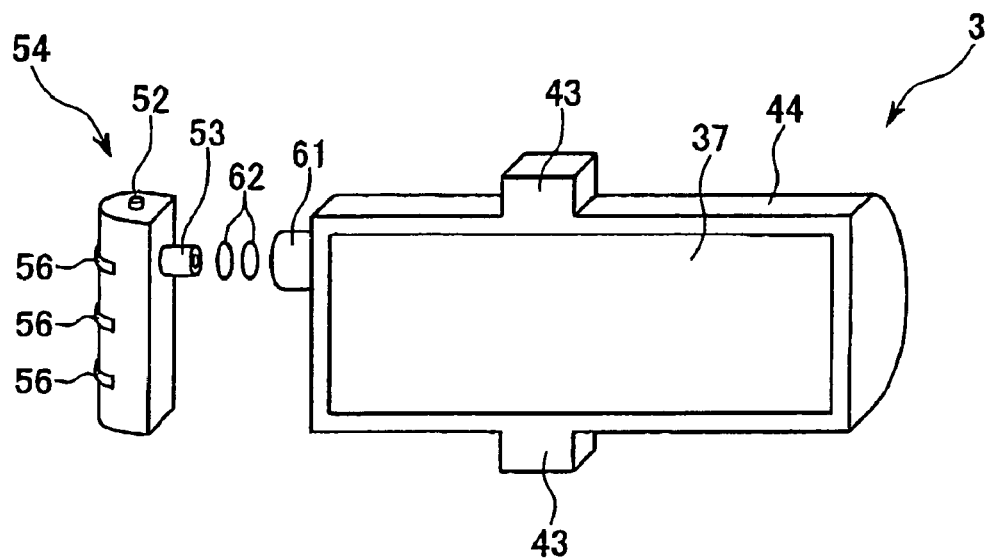
FIG. 14 is an exploded perspective view showing an image display unit that is provided in the endoscope system of the third embodiment.
Figure 15:
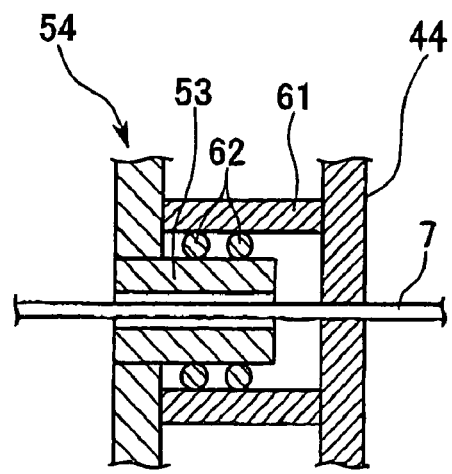
FIG. 15 is a cross-sectional view showing a second rotation shaft that is provided in the endoscope system of the third embodiment.
Figure 16:
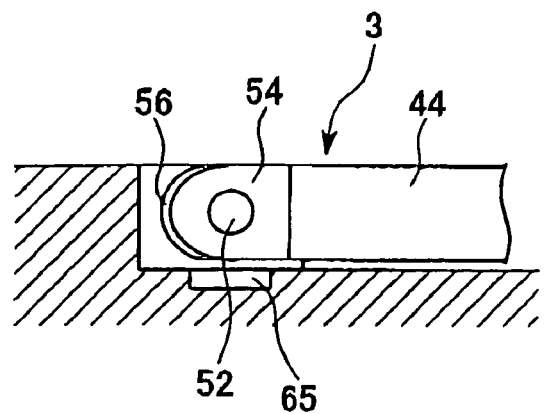
FIG. 16 is a cross-sectional view showing a first rotation shaft that is provided in the endoscope system of the third embodiment as well as portions adjacent thereto.
Figure 17:
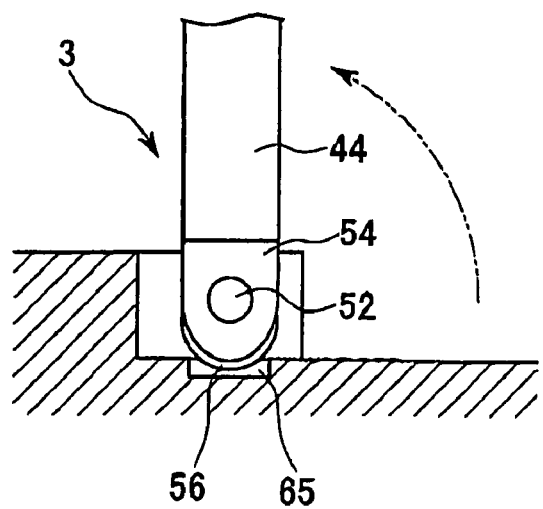
FIG. 17 is a cross-sectional view showing a first rotation shaft that is provided in the endoscope system of the third embodiment as well as portions adjacent thereto.

As is shown in FIG. 14 and FIG. 15, the rotating mechanism 54 is provided with a first rotation shaft 52 that extends in a perpendicular direction relative to the axis of the endoscope 1, and a second rotation shaft 53 that extends in a perpendicular direction relative to the first rotation shaft 52 and that supports the image display unit 3 such that it can rotate in a different direction from that of the first rotation shaft 52. The first rotation shaft 52 is a convex portion that is provided on both side surfaces in the longitudinal direction of the rotation mechanism 54 and that engages with a supporting hole 21B (described below). The second rotation shaft 53 is a convex portion that has a cylindrical shape and is provided at one end of the rotation mechanism 54. The second rotation shaft 53 engages with the image display unit body 44. In addition, as is shown in FIG. 16 and FIG. 17, an electrode 56 that supplies power and image signals from the endoscope 1 is provided at a base end of the rotation mechanism 54 such that, when the rotation mechanism 54 is axially rotated 90 degrees around the first rotation shaft 52, the electrode 56 is electrically connected to an electrode 65 (described below) which is formed in the recessed portion 21.

A convex portion 61 that has a cylindrical configuration and engages with the second rotation shaft 53 is formed at the end of the image display unit 44 that is linked to the rotation mechanism 54. A power supply cable 7 that supplies power and image signals to the display element 37 is located in aperture portions of the second rotation shaft 53 and the convex portion 61. The diameter of the aperture of the convex portion 61 is formed either substantially the same as or slightly larger than the outer diameter of the second rotation shaft 53, and an O-ring 62 that enables the convex portion 61 to rotate around the second rotation shaft 53 is placed in the gap that is created when the convex portion 61 and the second rotation shaft 53 are engaged. By employing this type of structure, the airtightness of the power supply cable 7 that is located inside the convex portion 61 and the second rotation shaft 53 is increased.

Figure 18:
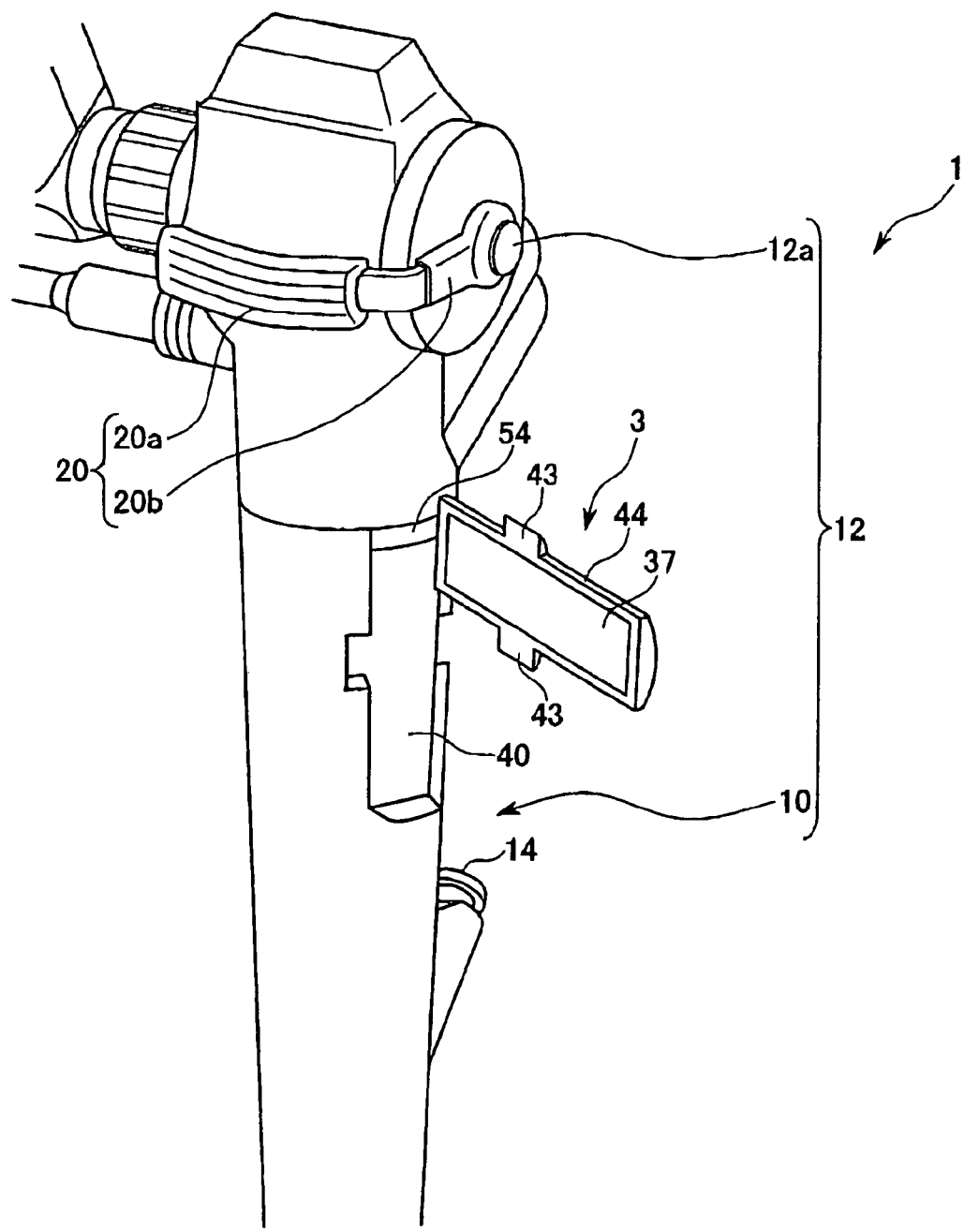
FIG. 18 is a perspective view showing the image display unit that is provided in the endoscope system of the third embodiment in an open state.

As is shown in FIG. 18, the image display unit 3 is able to be opened up from or shut inside the outer side surface of the operating section 12 through the rotation mechanism 54 that is provided with the first rotation shaft 52 and the second rotation shaft 53. As a result, in the same way as in the above described first embodiment, the orientation of the screen of the image display unit 3 can be freely adjusted.

A pair of supporting holes 21B are formed in the recessed portion 21 and the electrode 65 is additionally provided therein. The first rotation shaft 52 is engaged in the supporting holes 21 so that the image display unit 3 is supported such that it is able to rotate around the endoscope 1. The electrode 65 outputs power and image signals from the endoscope 1 to the image display unit 3 as a result of being in contact with the electrode 56.

The same operation and effects as those of the endoscope system of the previously described second embodiment are also present in the endoscope system having the structure described above. Furthermore, because the endoscope 1 and the image display unit 3 are electrically connected not by a cable but by the electrode 56, it is possible to avoid a situation in which the cable becomes tangled as a result of the image display unit 3 being rotated in a variety of directions relative to the endoscope 1.

Figure 19:
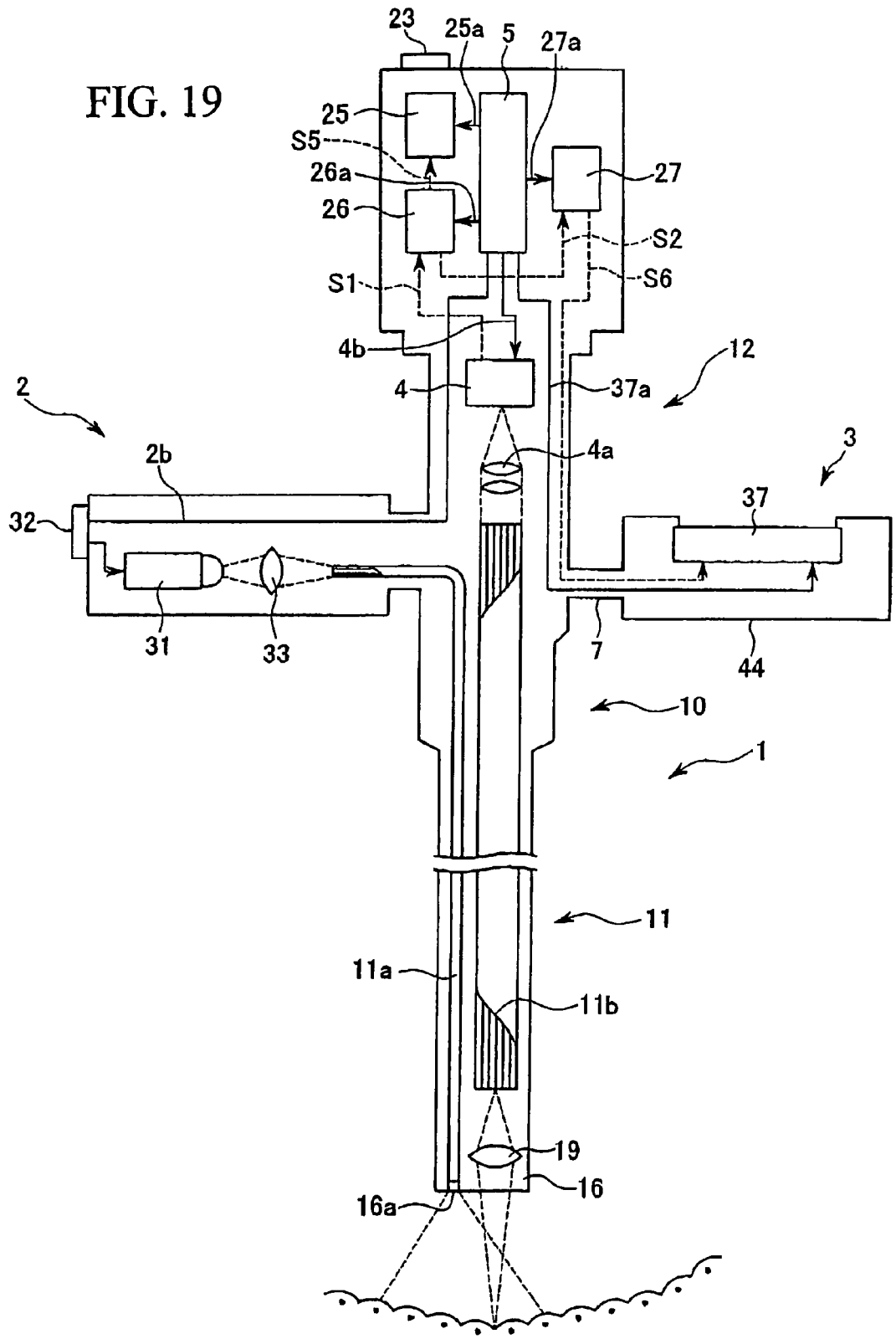
FIG. 19 is a schematic view showing the internal structure of an endoscope system to which the present invention can be applied in addition to the endoscope system of the third embodiment.

It is also possible in the present invention for the endoscope system to have a structure in which the image recording device 25, the image pickup element control circuit 26, and the display element control circuit 27 are provided in, for example, the image display unit 3. Moreover, the image display unit 3 is supported so that it can be opened or shut so as to face upwards in relation to the endoscope 1, however, it may also be supported so that it can be opened or shut so as to face in other directions (for example, in a downward direction). In addition, for example, as is shown in FIG. 19, the endoscope system may also have a structure in which the endoscope 1 and the light source apparatus 2 are formed integrally.

Fourth Embodiment

The fourth embodiment of the present invention will now be described with reference made to FIG. 20 through FIG. 25. Note that component elements that have previously been described in the above embodiments are given the same symbols and a description thereof is omitted.

Figure 20:
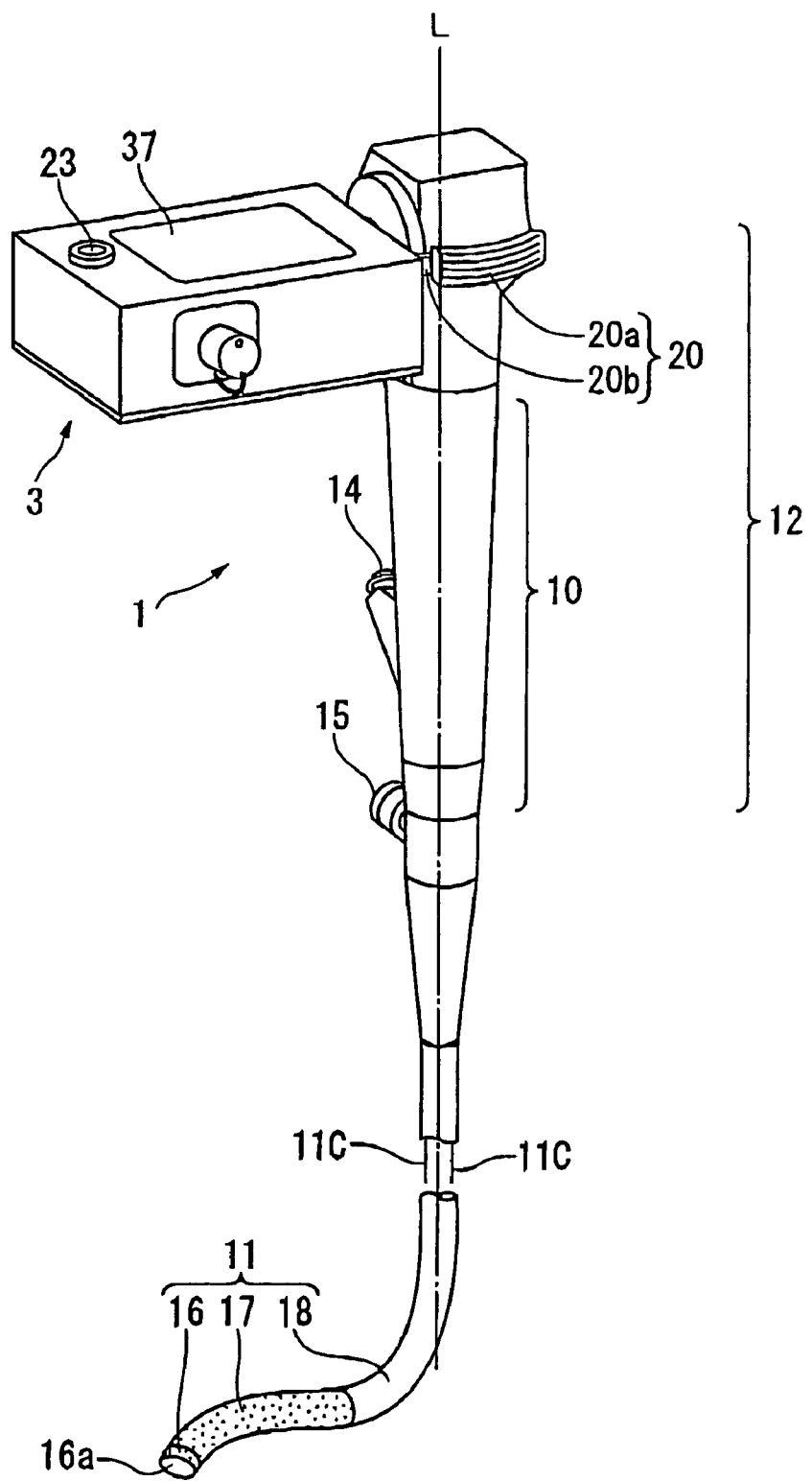
FIG. 20 is a perspective view showing an endoscope system of the fourth embodiment of the present invention.
Figure 21:
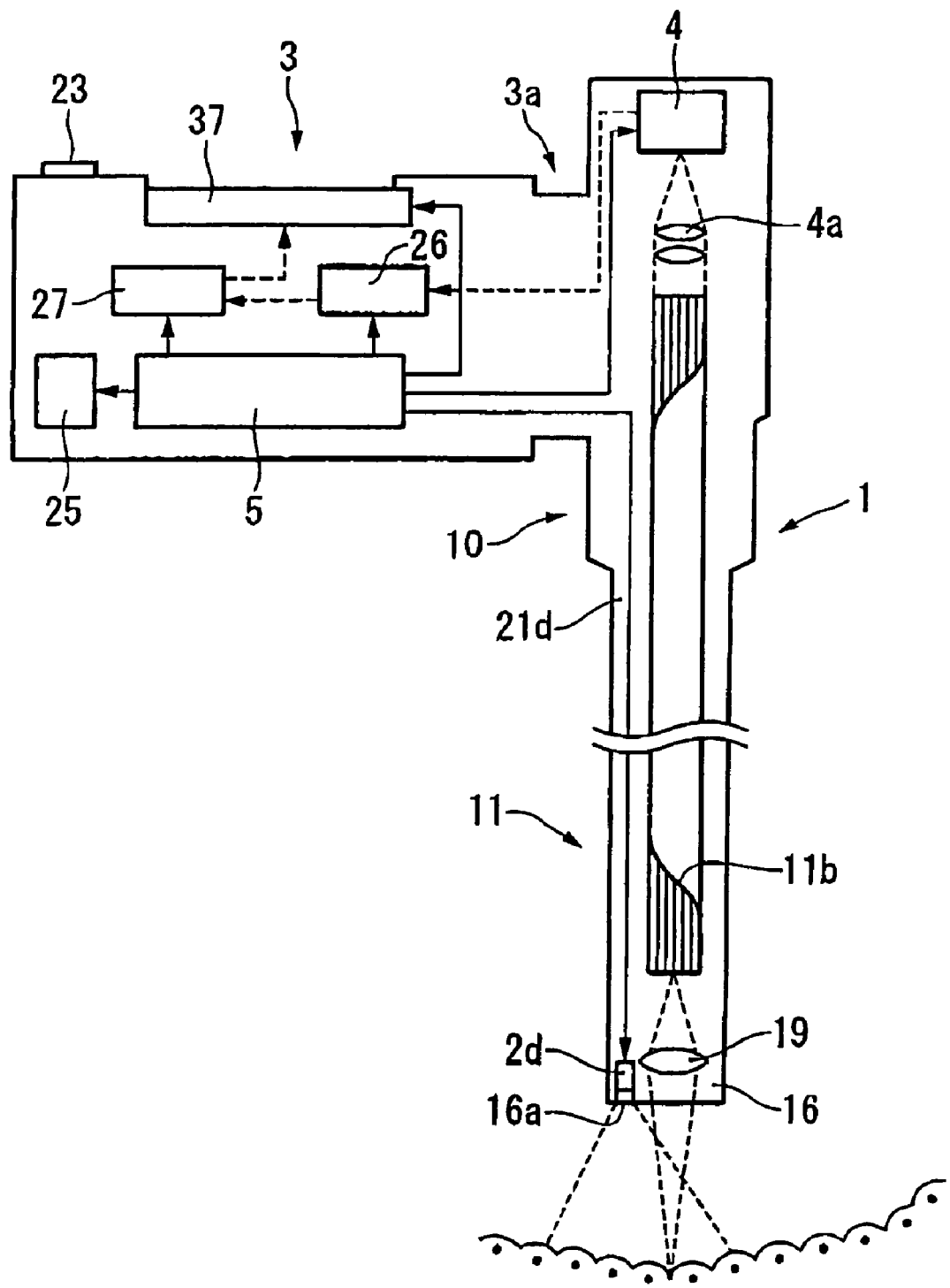
FIG. 21 is a schematic structural view showing the internal structure of the endoscope system of the fourth embodiment.

As is shown in FIG. 20 and FIG. 21, the principal component elements of the endoscope system of the present embodiment are an endoscope 1 and an image display unit 3 that creates an image from the image of the object obtained by the endoscope 1 and displays this created image.

As is shown in FIG. 20, the gripping portion 10 is formed in a rod shape extending in the longitudinal direction of an endoscope 1A such that it can be gripped by being enveloped by the thumb and the other fingers. The insertion portion 11 is flexible and is formed in a narrow elongated shape, and is provided so as to hang down from the gripping portion 10 when the gripping portion 10 is held with the thumb uppermost. The operating section 12 is provided adjacent to the portion immediately above the gripping portion 10 so that it can be operated by the thumb of the hand holding the gripping portion 10.

As is shown in FIG. 21, a light emitting diode (LED) is provided in the distal end portion 16 of the insertion portion 11. Inside the insertion portion 11 are incorporated an image guide 11b that guides images formed on the objective lens 19 to the image pickup element 4, and a power supply line 21d that is used to supply power from the battery 5 to an LED2d (described below). A finger switch 22d that an operator uses to turn on or turn off the LED2d as is desired is connected partway along the power supply line 21d.

Figure 22:
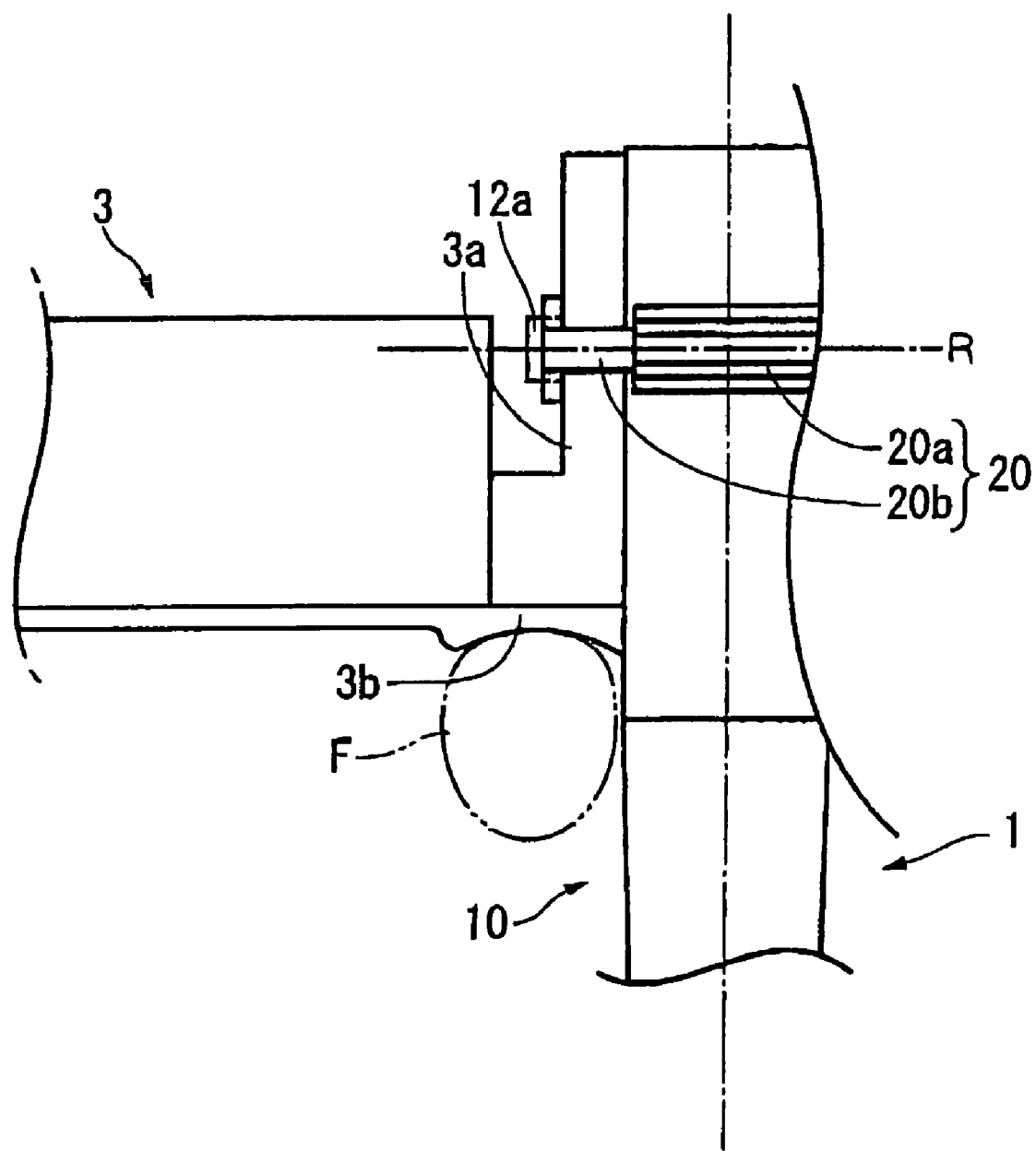
FIG. 22 is a frontal view showing an enlargement of a portion of the endoscope system of the fourth embodiment.

As is shown in FIG. 22, the bending operation lever 20 has a base end portion 20b that is axially supported by the rotation shaft 12a that is provided on the operation section 12, and the bending operation lever 20 is supported such that it is able to swing up and down around the rotation axis R of the rotation shaft 12a.

Figure 24:
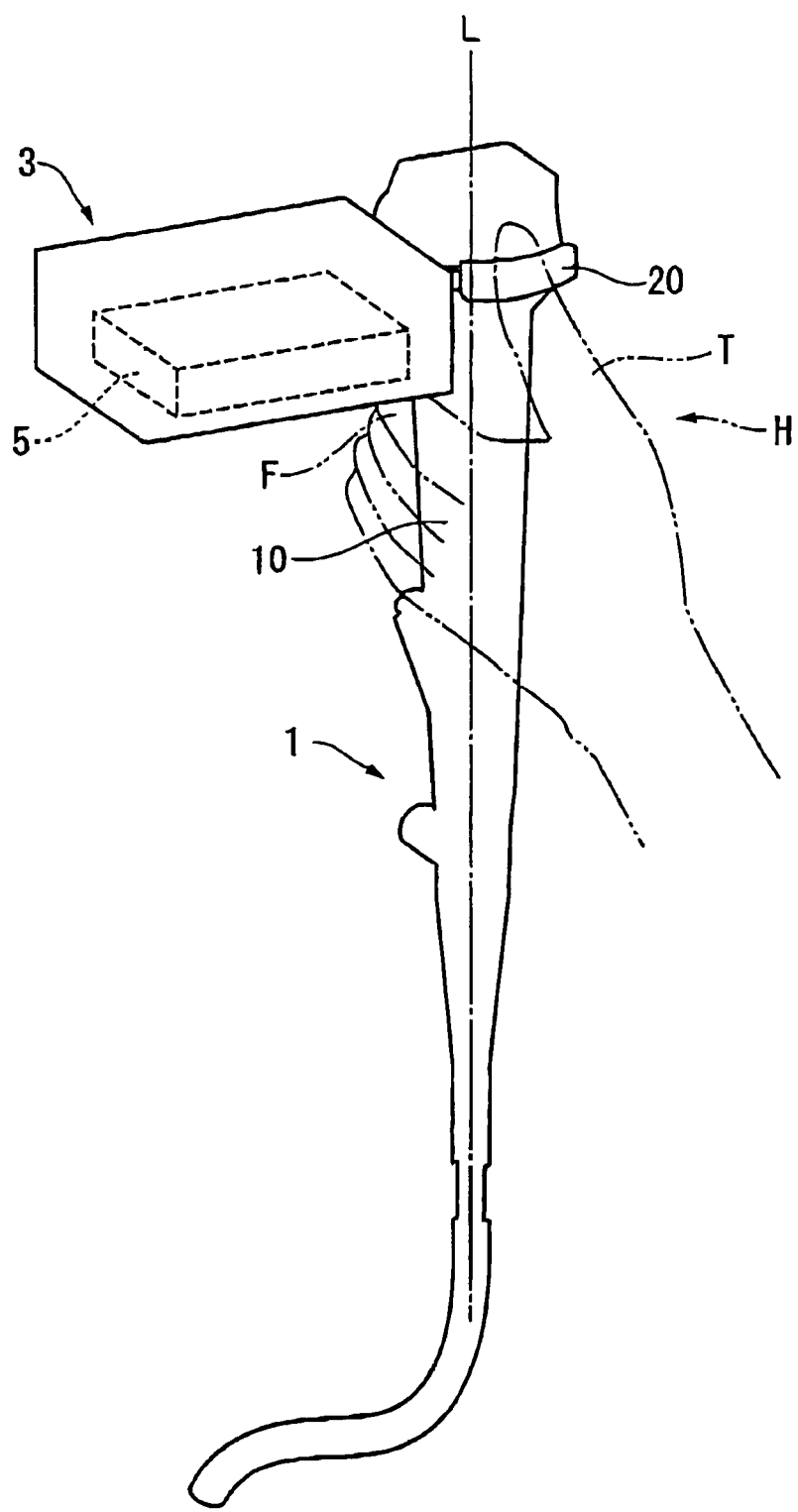
FIG. 24 is a view showing positional relationships between respective portions of the endoscope system when a gripping portion is gripped by a left hand.

As is shown in FIG. 20, FIG. 22, and FIG. 24, the image display unit 3 is mounted on the endoscope 1A using a linking portion 3a such that when a thumb T (shown only in FIG. 24) is positioned uppermost and the gripping portion 10 of the endoscope 1A is gripped by a left hand (i.e., the fingers thereof) H, the image display unit 3 is positioned above the gripping fingers apart from the thumb T and protrudes from a side portion of the operating section 12 of the endoscope 1A.

A replaceable battery 5 that supplies power to the respective portions including the LED 2d, the image pickup element 4, and the image display unit 3 is built into the image display unit 3. As is shown in FIG. 22, the image display unit 3 is provided at such a position that the display element 37 is substantially equal in the vertical direction to the rotation shaft 12a of the bending operation lever 20.

Furthermore, a finger piece 3b protrudes from a side portion of the endoscope 1 where the image display unit 3 is provided. This finger piece 3b is provided at a position where it can be squeezed by an index finger (i.e., a finger) F when the gripping portion 10 is gripped by the left hand H. For example, it can be squeezed by the portion extending from the base of the index finger to the first joint thereof. The image display unit 3 is integrally provided on the upper side of this finger piece 3b, and an excellent weight balance can be obtained by supporting the image display unit 3 from below using the index finger F.

The image display unit 3 and the endoscope 1 are mutually connected via a power supply line 4b (described below) and the signal line S1 that pass through a linking portion 3a.

Figure 23:
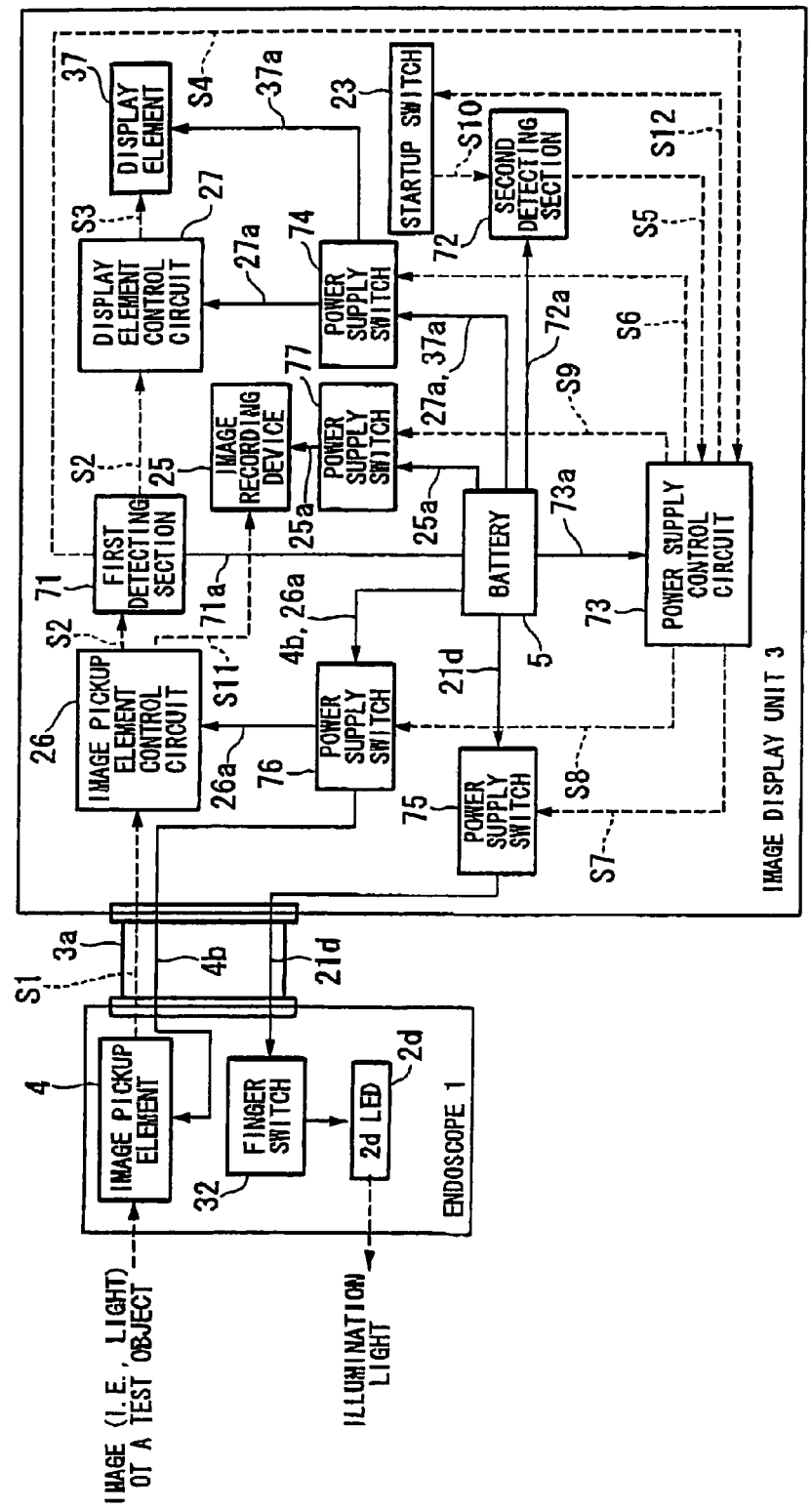
FIG. 23 is a functional block view of the endoscope system of the fourth embodiment.

Next, FIG. 23 shows functional blocks of the endoscope system. As is shown in FIG. 23, this endoscope system is provided with a first detecting section 71 that detects whether or not image signals (i.e., images that have been converted into signals in the image pickup element 4) that have been transmitted to the image display unit 3 from the image pickup element 4 have been input, a second detecting section 72 that detects the ON/OFF state of the startup switch 23, and a power supply control circuit (i.e., a control portion) 73 that cuts out the supply of power to the LED2d, the image pickup element 4, the display element 37, and the image recording device 25 and that renders invalid operations of the startup switch 23 based on detection results from the first detecting section 71 and the second detecting section 72.

In addition, this endoscope system is also provided with a power supply switch 74 that is driven by the power supply control circuit 73 and interrupts the power supply paths (i.e., the power supply lines 27a and 37a described below) from the battery 5 to the display element 37 and the display element control circuit 27, a power supply switch 77 that, in the same way, is driven by the power supply control circuit 73 and interrupts the power supply path (i.e., the power supply line 25a described below) from the battery 5 to the image recording device 25, a power supply switch 75 that, in the same way, is driven by the power supply control circuit 73 and interrupts the power supply path (i.e., the power supply line 21d described below) from the battery 5 to the LED2d, and a power supply switch 76 that is driven by the power supply control circuit 73 and interrupts the power supply paths (i.e., the power supply lines 4b and 26a described below) from the battery 5 to the image pickup element 4 and the image pickup element control circuit 26.

The power supply line 4b that supplies power to the image pickup element 4 is provided between the image pickup element 4 and the battery 5, while the power supply line 21d that supplies power to the LED2d is provided between the LED2d and the battery 5. In the same way, the power supply line 71a that supplies power to the first detecting section 71 is provided between the first detecting section 71 and the battery 5, the power supply line 26a that supplies power to the image pickup element control circuit 26 is provided between the image pickup element control circuit 26 and the battery 5, the power supply line 27a that supplies power to the display element control circuit 27 is provided between the display element control circuit 27 and the battery 5, and the power supply line 37a that supplies power to the display element 37 is provided between the display element 37 and the battery 5.

Furthermore, the power supply line 25a that supplies power to the image recording device 25 is provided between the image recording device 25 and the battery 5, the power supply line 72a that supplies power to the second detecting section 72 is provided between the second detecting section 72 and the battery 5, and the power supply line 73a that supplies power to the power supply control circuit 73 is provided between the power supply control circuit 73 and the battery 5. The power supply switch 74 is provided partway along the power supply lines 27a and 37a, the power supply switch 75 is provided part way along the power supply line 21d, the power supply switch 76 is provided partway along the power supply lines 4b and 26a, and the power supply line 77 is provided partway along the power supply line 25a.

The signal line S1 that transmits image signals that have been acquired by the image pickup element 4 to the image pickup element control circuit 26 is provided between the image pickup element 4 and the image pickup element control circuit 26, the signal line S2 that transmits image signals that have been input into the image pickup element control circuit 26 to the display element control circuit 27 is provided between the image pickup element control circuit 26 and the display element control circuit 27, and the signal line S3 that inputs image signals that have been input into the display element control circuit 27 to the display element 37 is provided between the display element control circuit 27 and the display element 37. In addition, the first detecting section 71 is provided partway along the signal line S2.

The signal line S4 that transmits signals output from the first detecting section 71 to the power supply control circuit 73 is provided between the power supply control circuit 73 and the first detecting section 71, while the signal line that S5 also transmits signals output from the second detecting section 72 to the power supply control circuit 73 is provided between the power supply control circuit 73 and the second detecting section 72. Moreover, a signal line S6 that transmits to the power supply switch 74 signals that have been output from the power supply control circuit 73 in order to interrupt the supply of power to the display element 37 is provided between the power supply control circuit 73 and the power supply switch 74, and a signal line S7 that transmits to the power supply switch 75 signals that have been output from the power supply control circuit 73 in order to interrupt the supply of power to the LED2d is provided between the power supply control circuit 73 and the power supply switch 75.

Furthermore, a signal line S8 that transmits to the power supply switch 76 signals that have been output from the power supply control circuit 73 in order to interrupt the supply of power to the image pickup element 4 is provided between the power supply control circuit 73 and the power supply switch 76, and a signal line S9 that transmits to the power supply switch 77 signals that have been output from the power supply control circuit 73 in order to interrupt the supply of power to the image recording device 72 is provided between the power supply control circuit 73 and the power supply switch 77.

A signal line S10 that transmits signals showing the ON/OFF state of the startup switch 23 is provided between the startup switch 23 and the second detecting section 72, while a signal line S11 that transmits image signals to the image recording device 25 is provided between the image pickup element control circuit 26 and the image recording device 25. Moreover, a signal line S12 that transmits signals in order to start up or shut down the endoscope system is provided between the power supply control circuit 73 and the startup switch 23.

In an endoscope system having the above described structure, when the endoscope system is started up by the startup switch 23, the power supply control circuit 73 firstly closes the power supply switches 74, 75, and 76 and secures the respective power supply paths (i.e., the power supply lines 4b, 25a, 26a, 27a, 37a, and 21d) to the image pickup element 4, the image pickup element control circuit 26, the display element control circuit 27, the display element 37, the image recording device 25, and the LED2d.

The power supply control circuit 73 determines whether or not image signals have been input from the image pickup element 4 to the image display unit 3 based on detection results from the first detecting section 71, and determines whether or not the LED2d is being driven. If the first detecting section 71 outputs a signal showing a detection result that indicates that an image signal has not been input from the image pickup element 4 to the image display unit 3, the power supply control circuit 73 opens the power supply switches 74 and 75 and interrupts the power supply paths to the display element control circuit 27, the display element 37, the image recording device 25, and the LED2d (i.e., the power supply lines 25a, 27a, 37a, and 21d), and also renders the startup switch 23 invalid.

Next, the power supply control circuit 73 determines whether or not an external command to end processing is present, and if this end command is present, the above described processing is ended. If there is no end command, the above described processing is repeated.

Moreover, if the LED2d is being driven, the power supply control circuit 73 determines whether or not operations of the startup switch 23 are valid or invalid. If the LED2d is not being driven, then, in the same way, the power supply control switch 73 opens the power supply switches 74 and 75, interrupts the power supply lines 25a, 27a, 37a, and 21d, and also renders the startup switch 23 invalid.

Note that even if the operations of the startup switch 23 are valid, because the startup switch 23 has been turned off, namely, is in an OFF state, the power supply control circuit 73 determines whether the startup switch 23 is in an ON state or an OFF state based on detection results from the second detecting section 72. Here, if the operations of the startup switch 23 are invalid, the power supply control circuit 73 switches the operations of the startup switch 23 to a valid state.

If the second detecting section 72 outputs a signal showing a detection result that indicates that the startup switch 23 is in an ON state, the power supply control circuit 73 determines whether or not the power supply switches 74 and 75 are closed. If the second detecting section 72 outputs a signal showing a detection result that indicates that the startup switch 23 is in an OFF state, in the same way as is described above, the power supply control circuit 73 opens the power supply switches 74 and 75, interrupts the power supply lines 25a, 27a, 37a, and 21d, and also renders the startup switch 23 invalid.

If the power supply switches 74 and 75 are closed, in the same way as is described above, the power supply control circuit 73 determines whether or not an external command to end processing is present. If the power supply switches 74 and 75 are open, then after the power supply control circuit 73 has closed the power supply switches 74 and 75 and secured the power supply lines 25a, 27a, 37a, and 21d, the processing is ended if the end command is present. If, however, no end command is present, then in the same way as is described above, the processing to determine whether or not image signals have been input from the image pickup element 4 to the image display unit 3 is repeated.

In the endoscope system according to the present embodiment, the endoscope 1 that is provided with the image pickup element 4 that picks up an image of an object is provided integrally with the image display unit 3 that converts pictures of an object that have been obtained by the image pickup element 4 into images and then displays these. When a thumb T is positioned uppermost and the gripping portion 10 of the endoscope 1A is gripped, the image display unit 3 is attached such that it is positioned above the gripping fingers apart from the thumb T and protrudes from a side portion of the operating section 12 of the endoscope 1A. As a result, the weight of the image display unit 3 can be supported by the fingers. Because of this, it is possible to appropriately suppress the effects on the hand gripping the endoscope from the force trying to rotate it towards the image display unit 3 side, namely, the opposite forces that are trying to twist the wrist. As a result, an excellent weight balance can be obtained and the load on the hand during use can be reduced. Moreover, because the image display unit 3 is supported by the fingers, it is difficult for any wavering or the like to be generated in the displayed image and the viewability of an image during an operation is vastly improved. Accordingly, an even greater increase in operability is obtained.

In addition, in the present embodiment there are provided the endoscope 1 that includes the image pickup element 4 that picks up an image of an object and the operation section 12 that is able to operate the endoscope 1, the finger piece portion 3b that is provided so as to intersect the longitudinal axis L of the operating section 12, and the image display unit 3 that is provided integrally with the finger piece portion 3b and converts pictures of objects obtained by the image pickup element 4 into images and then displays them. In this manner, because the image display unit 3 is provided integrally with the finger piece portion 3b, the weight of the image display unit 3 is supported by the index finger F and an excellent weight balance can be obtained in the endoscope system.

Furthermore, because the operating section 12 is provided with the bending operation lever 20 that is provided so as to be able to rotate in a vertical direction around the rotation axis R, and the image display unit 3 is provided at substantially the same position in the vertical direction as the rotation shaft 12 of the bending operation lever 20, it is also possible to suppress opposing forces that might twist a wrist from being generated when the bending operation lever 20 is being operated as well. Because of this, the stability of the endoscope system that is being held is further increased.

Moreover, because it is possible for an operator to accurately check both the finger movement of the operating lever 20 and the images simply by moving their line of sight and without moving their face, operability can be improved even further.

Figure 25:
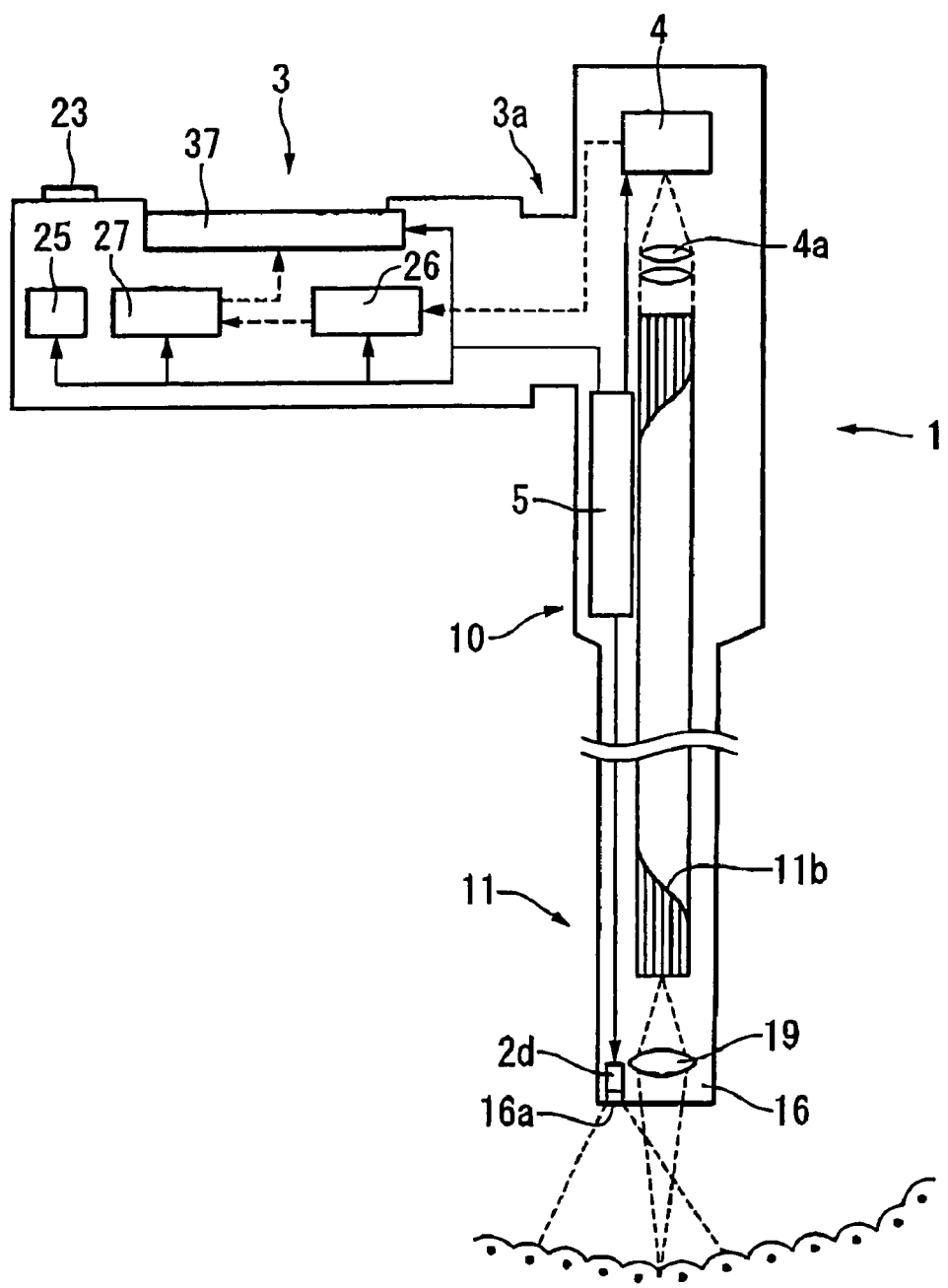
FIG. 25 is a view showing a modification of the endoscope system of the fourth embodiment and is a functional block view of this endoscope system.

Note that, in this endoscope system, the battery 5 is provided inside the image display unit 3, however, as is the case with the endoscope system shown in FIG. 25, for example, it is also possible to employ a structure in which the battery 5 is reduced in size and provided inside the gripping portion 10. This endoscope system differs from the above endoscope system only in that the position of the battery 5 is different.

By employing this structure, because the thickness and size of the image display unit 3 can be reduced even further, and because the battery 5 which is comparatively heavy is positioned right next to the longitudinal axis L of the endoscope, it is possible to even more effectively prevent the occurrence of opposing forces that might twist a wrist.

Fifth Embodiment

The fifth embodiment of the present invention will now be described with reference made to FIG. 26 through FIG. 31. Note that component elements that have previously been described in the above embodiments are given the same symbols and a description thereof is omitted.

As is shown in FIG. 26 through FIG. 29, instead of the LED 2d there is provided the light source apparatus 2 that generates a larger quantity of irradiation light to illuminate an object. The light source apparatus 2 is provided integrally with the endoscope 1 so as to protrude towards the symmetrically opposite side from the image display unit 3 with the longitudinal axis of the endoscope 1 sandwiched in between.

Figure 26:
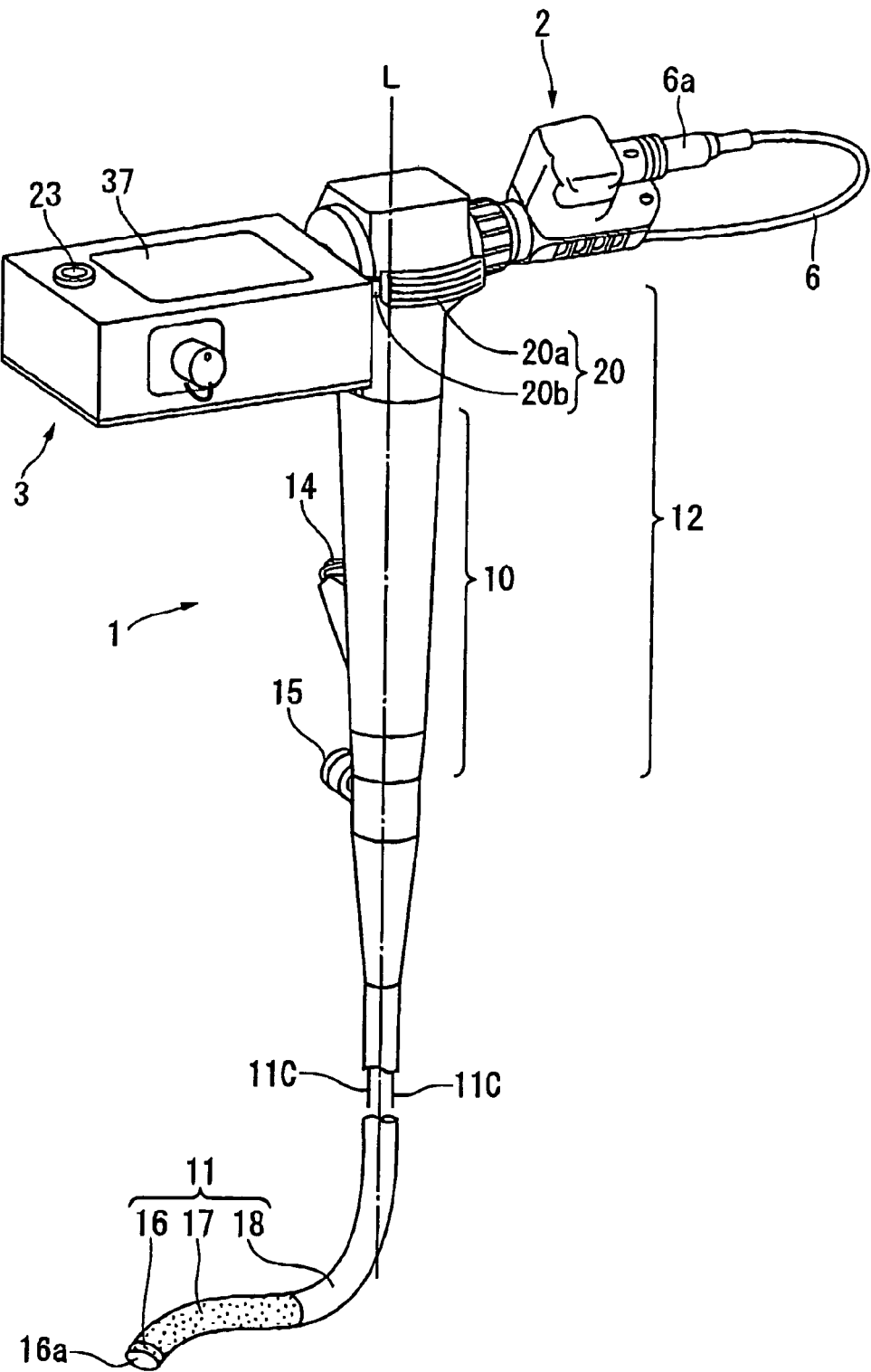
FIG. 26 is a perspective view showing an endoscope system of the fifth embodiment of the present invention.
Figure 27:
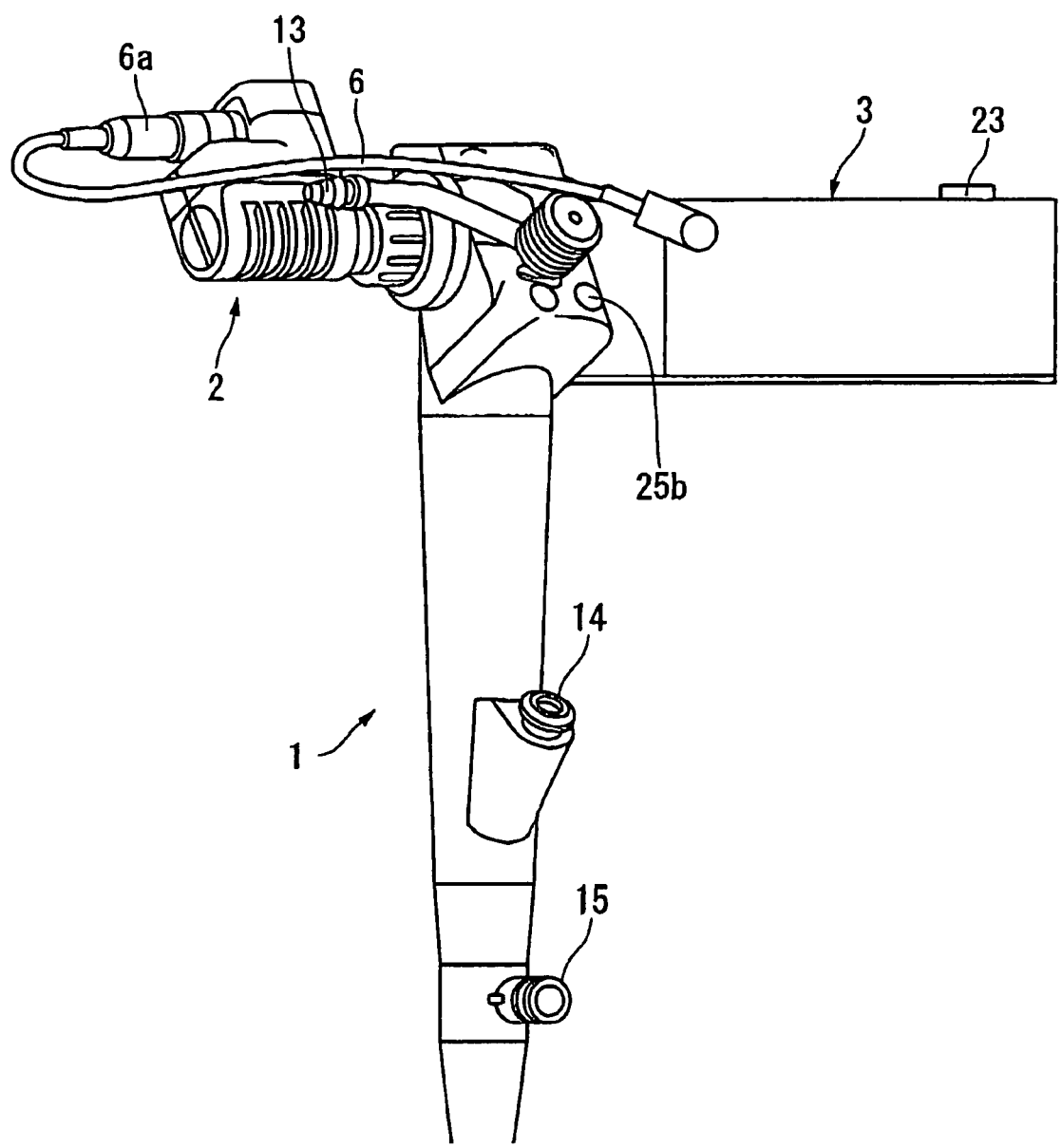
FIG. 27 is a perspective view looking from a different direction from that in FIG. 7 of the endoscope system of the fifth embodiment.
Figure 28:
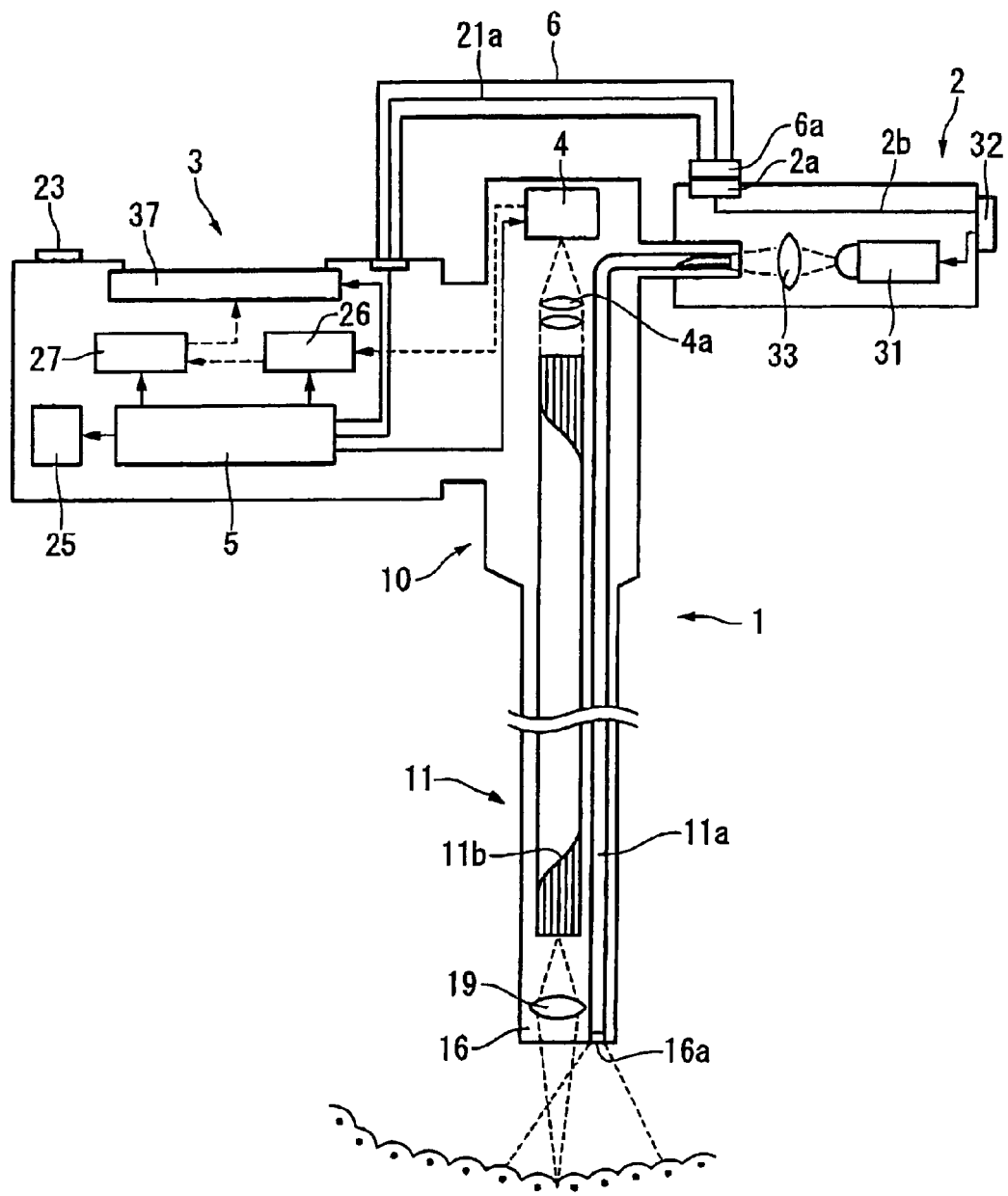
FIG. 28 is a schematic structural view showing the internal structure of the endoscope system of the fifth embodiment.
Figure 29:
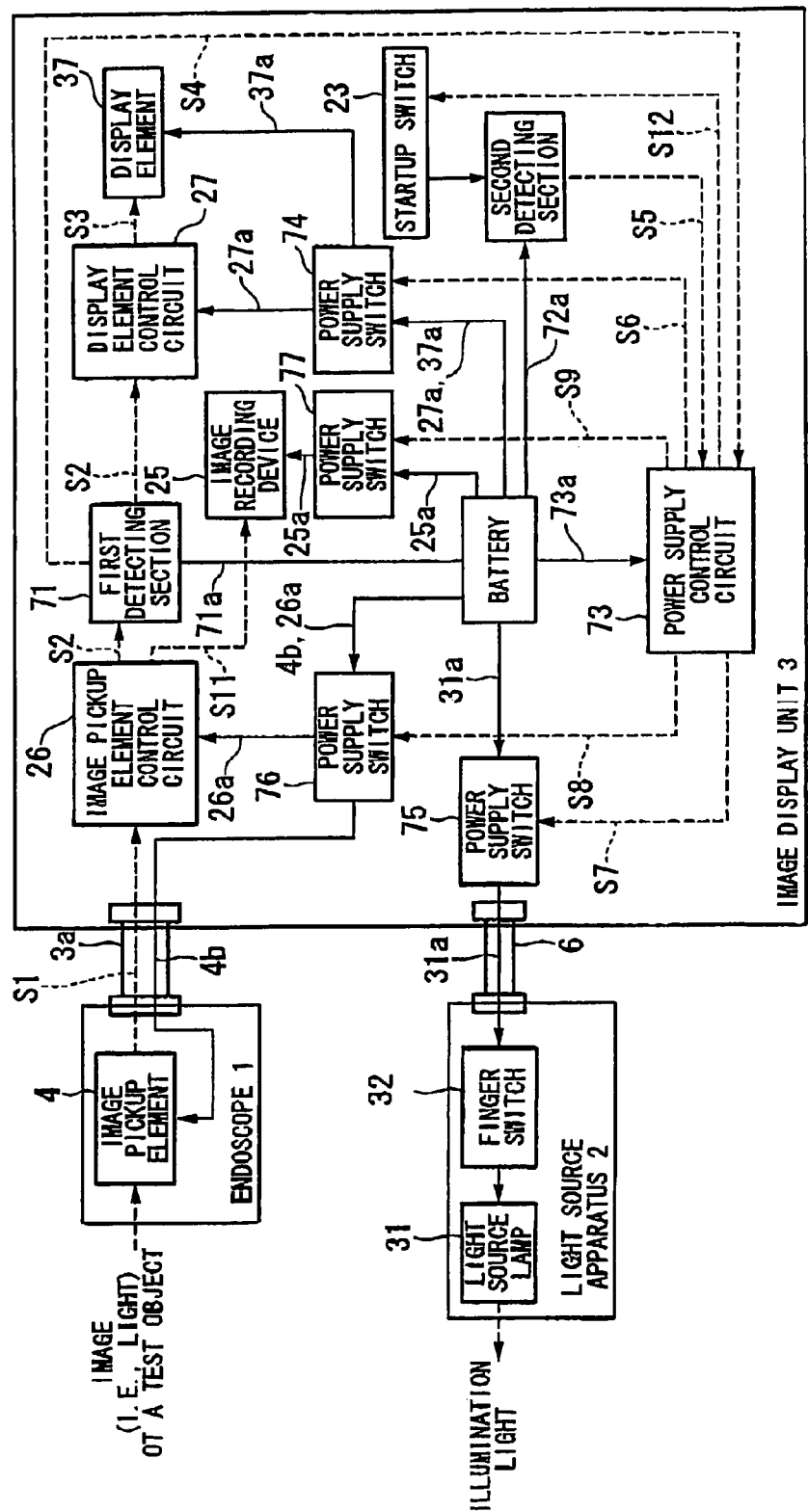
FIG. 29 is a functional block view of the endoscope system of the fifth embodiment.
Figure 31:
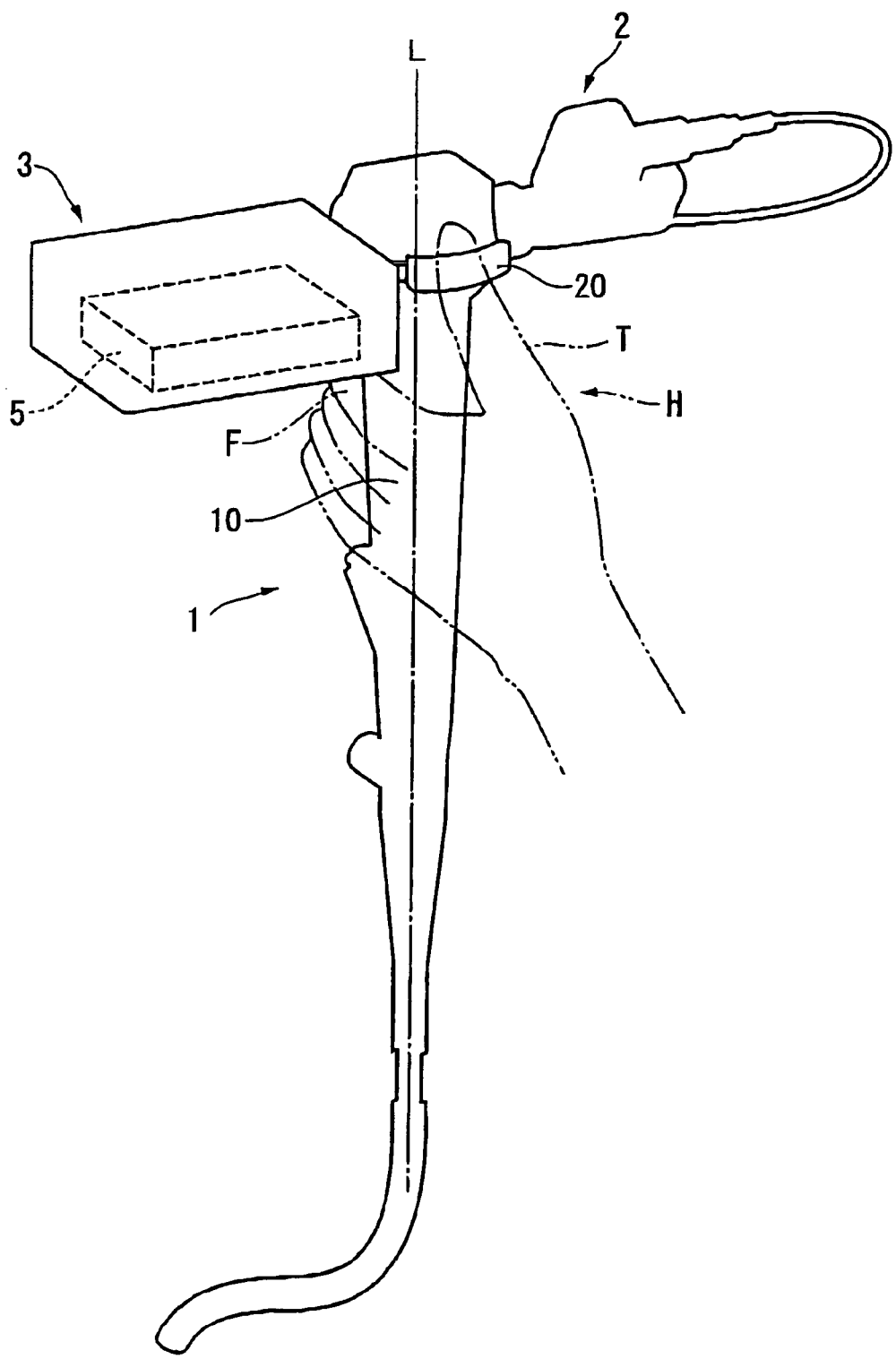
FIG. 31 is a view showing positional relationships between respective portions of the endoscope system when a gripping portion is gripped by a left hand.

As is shown in FIG. 26, FIG. 27, and FIG. 31, the image display unit 3 is mounted on the endoscope 1 using a linking portion 3a such that when a thumb T is pointing upwards and the gripping portion 10 of the endoscope 1 is gripped by a left hand H, the image display unit 3 is positioned above the gripping fingers apart from the thumb T and protrudes from a side portion of the operating section 12 of the endoscope 1.

Figure 30:
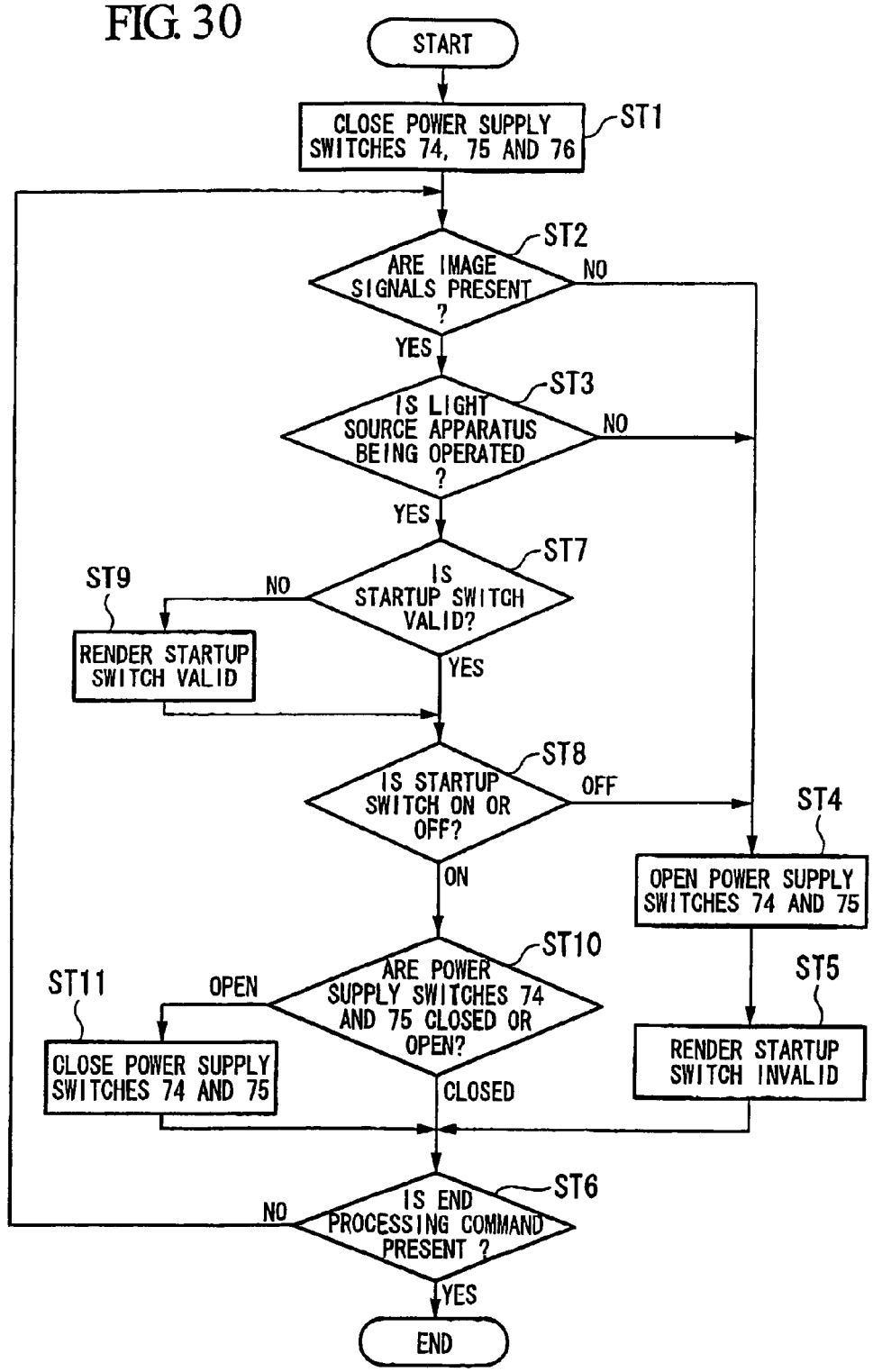
FIG. 30 is a flow chart for illustrating control for reducing power consumption that is implemented in the endoscope system of the fifth embodiment.

Control to reduce power consumption that is carried out in an endoscope system having the above described structure will now be described using the flow chart shown in FIG. 30.

When the endoscope system is started up by the startup switch 23, the power supply control circuit 73 firstly closes the power supply switches 74, 75, and 76 and secures the respective power supply paths (i.e., the power supply lines 4b, 25a, 26a, 27a, 31a, and 37a) to the image pickup element 4, the image pickup element control circuit 26, the display element control circuit 27, the display element 37, the image recording device 25, and the light source apparatus 2 (step ST1).

The power supply control circuit 73 determines whether or not image signals have been input from the image pickup element 4 to the image display unit 3 based on detection results from the first detecting section 71 (step ST2)

In step ST2, even if the first detecting section 71 outputs a signal showing a detection result that indicates that an image signal has been input from the image pickup element 4 to the image display unit 3, there may still be cases in which the power supply cable 6 is not connected to the light source apparatus 2. Therefore, the power supply control circuit 73 determines whether or not the light source apparatus 2 is being driven (step ST3).

In step ST2, if the first detecting section 71 outputs a signal showing a detection result that indicates that an image signal has not been input from the image pickup element 4 to the image display unit 3, the power supply control circuit 73 opens the power supply switches 74 and 75 and interrupts the power supply paths to the display element control circuit 27, the display element 37, the image recording device 25, and the light source apparatus 2 (i.e., the power supply lines 25a, 27a, 31a, and 37a) (step ST4), and also renders the startup switch 23 invalid (step ST5). Next, the power supply control circuit 73 determines whether or not an external command to end processing is present (step ST6), and if this end command is present, the above described processing is ended. If there is no end command, the routine returns to step ST2 and the above described processing is repeated.

In step ST3, if the light source apparatus 2 is being driven (i.e., if the cable 6 is connected), the power supply control circuit 73 determines whether or not operations of the startup switch 23 are valid or invalid (step ST7). If, in step ST3, the light source apparatus 2 is not being driven (i.e., if the cable 6 is not connected), the power supply control switch 73 moves to the above described step ST4.

In step ST7, even if the operations of the startup switch 23 are valid, because the startup switch 23 has been turned off, namely, is in an OFF state, the power supply control circuit 73 determines whether the startup switch 23 is in an ON state or an OFF state based on detection results from the second detecting section 72 (step ST8). In step ST7, if the operations of the startup switch 23 are invalid, the power supply control circuit 73 switches the operations of the startup switch 23 to a valid state (step ST9) and then moves to step ST8.

In step ST8, if the second detecting section 72 outputs a signal showing a detection result that indicates that the startup switch 23 is in an ON state, the power supply control circuit 73 determines whether or not the power supply switches 74 and 75 are closed (step ST10). In step ST8, if the second detecting section 72 outputs a signal showing a detection result that indicates that the startup switch 23 is in an OFF state, then the power supply control circuit 73 moves to the above described step ST4.

In step ST10, if the power supply switches 74 and 75 are closed, then the power supply control circuit 73 moves to the above described step ST6. If, however, in step ST10, the power supply switches 74 and 75 are open, then after the power supply control circuit 73 has closed the power supply switches 74 and 75 and secured the supply of power to the display element control circuit 27, the display element 37, the image recording device 25, and the light source apparatus 2 (i.e., the power supply lines 25a, 27a, 37a, and 21d) (step ST11), the routine moves to step ST6 and the processing is ended if an end command is present. If, however, no end command is present, then the routine returns to step ST2 and the above described processing is repeated.

In the above described endoscope system, if signals have not been input from the image pickup element 4 to the image display unit 3, then unnecessary power consumption can be prevented by not supplying power to the display element 37, by not supplying power to the light source apparatus 2, and by rendering operations of the startup switch 23 invalid. As a result, an extended period of use is possible even if a small size battery is installed in order to improve portability.

In the endoscope system according to the present embodiment, the light source apparatus 2 that illuminates an object is provided integrally with the endoscope so as to protrude towards the symmetrically opposite side from the image display unit 3 with the longitudinal axis L of the endoscope 1B sandwiched in between. In this manner, by mounting the light source apparatus 2 and the image display unit 3, which are both comparatively heavy component elements, in symmetrical positions relative to each other on either side of the longitudinal axis L, the center of gravity of the endoscope system can be placed in a closer position to the central axis, and a more suitable equilibrium can be obtained for the left-right weight balance of the endoscope system. As a result, this endoscope system is easy to operate over an extended period of time.

Sixth Embodiment

The sixth embodiment of the present invention will now be described with reference made to FIG. 32 through FIG. 37. Note that component elements that have previously been described in the above embodiments are given the same symbols and a description thereof is omitted.

Figure 32:
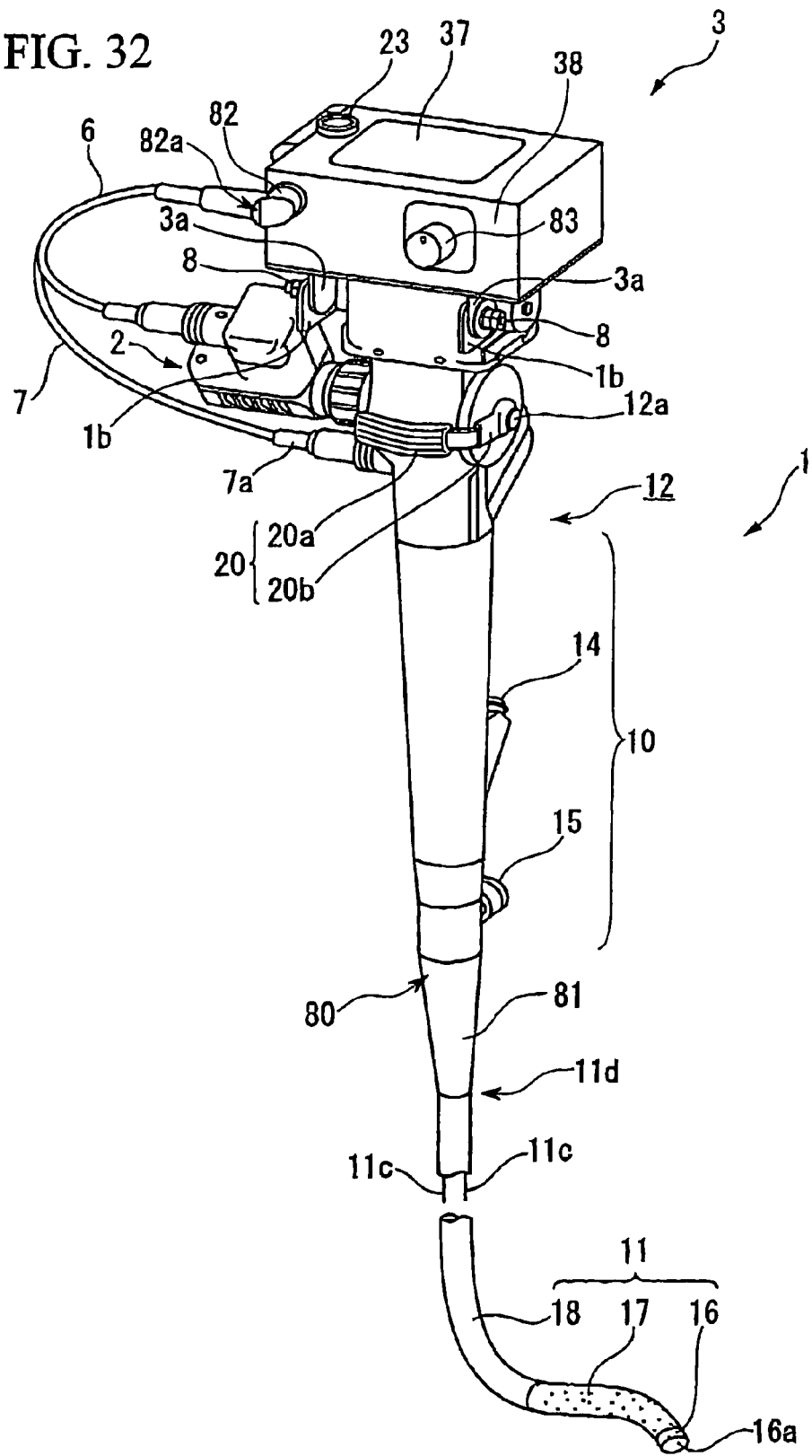
FIG. 32 is a perspective view showing an endoscope system of the sixth embodiment of the present invention.
Figure 33:
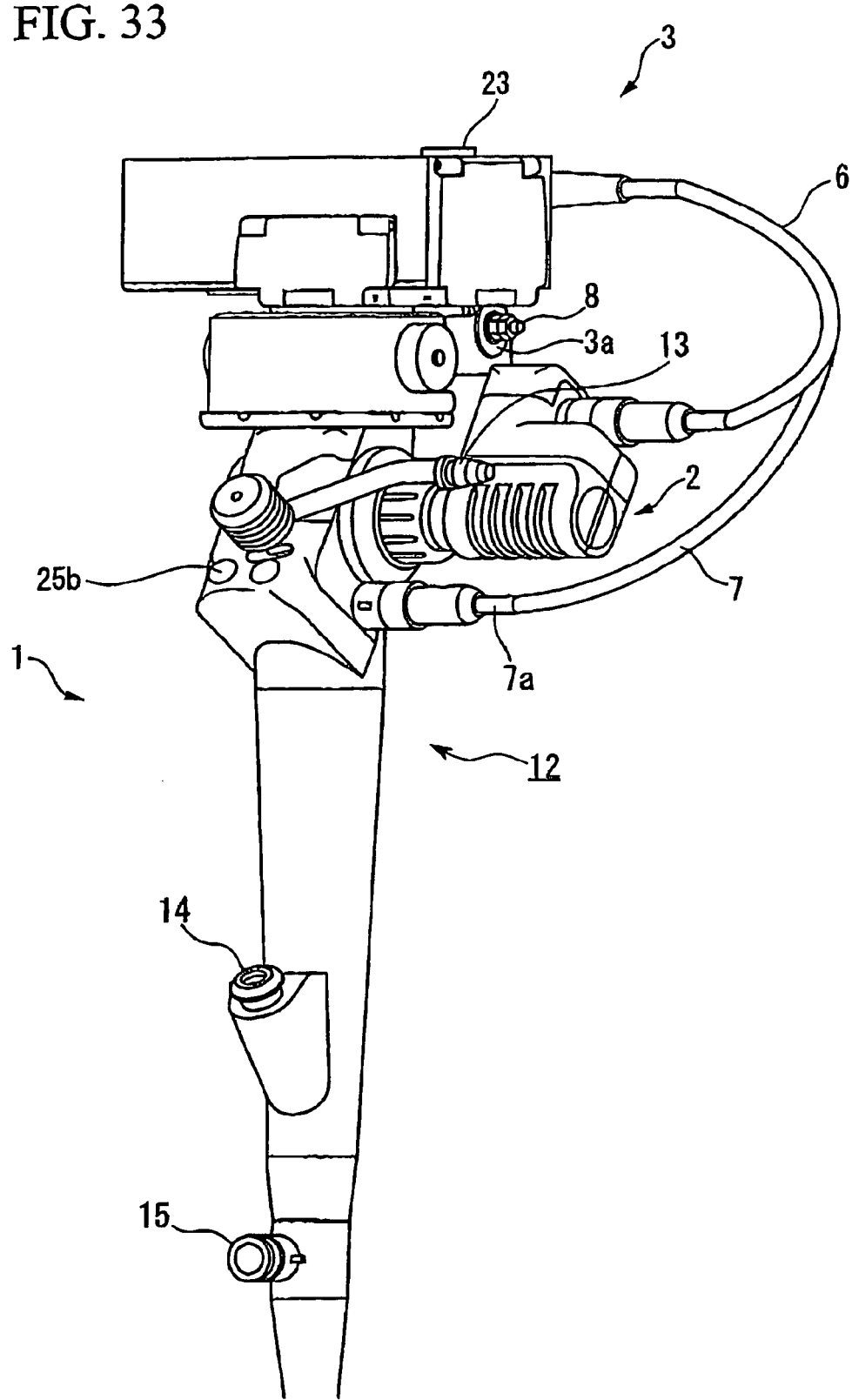
FIG. 33 is a perspective view looking from a different direction from that in FIG. 1 of the endoscope system of the sixth embodiment.
Figure 34:
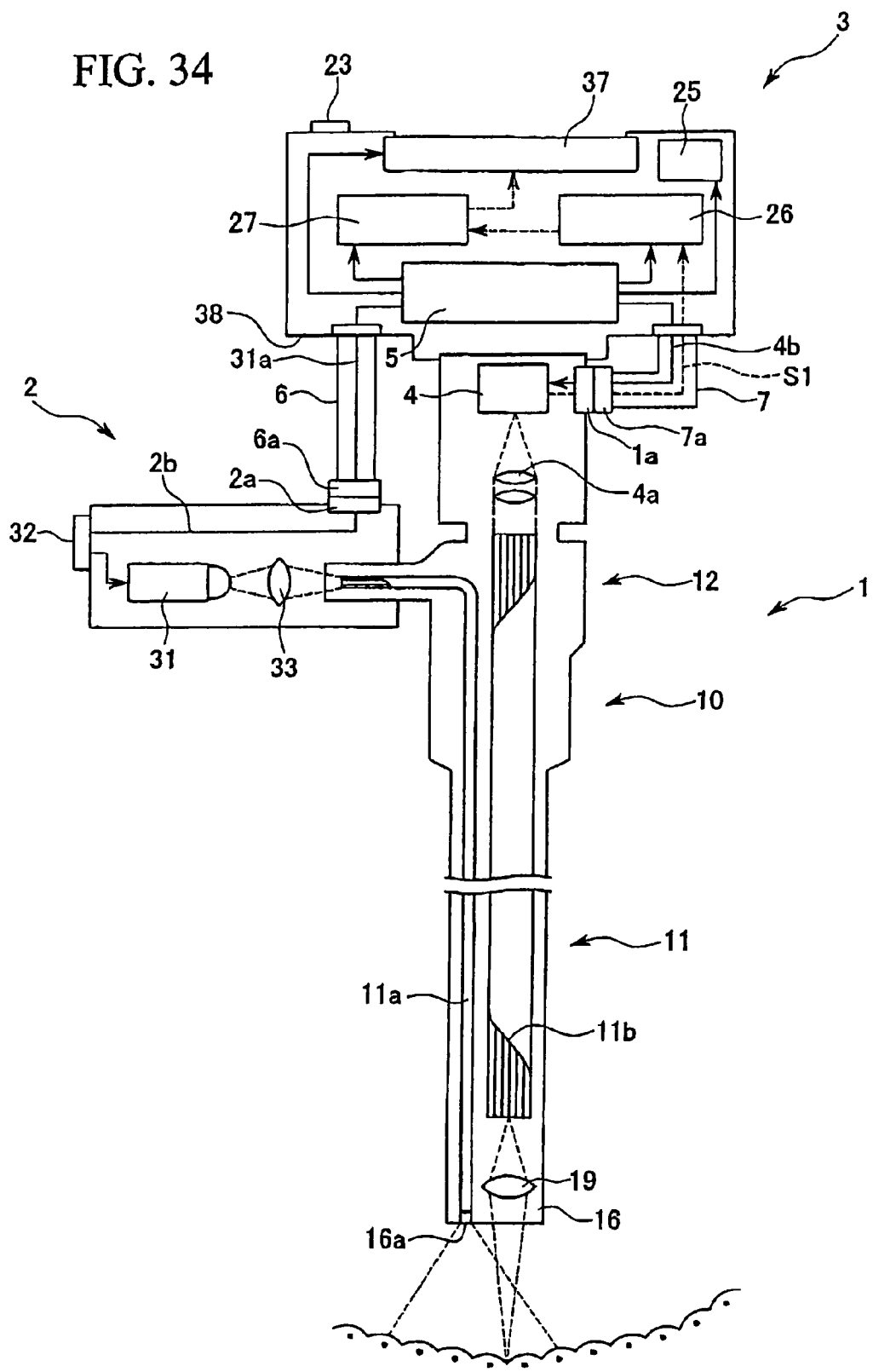
FIG. 34 is a typical view to schematically illustrate the internal structure of the endoscope system of the sixth embodiment.

As is shown in FIG. 32 to FIG. 34, the principal component elements of the endoscope system of the present embodiment are an endoscope 1, a light source apparatus 2 that generates illumination light to illuminate an object, and an image display unit 3 (i.e., an observation section) that creates an image from the image of the object obtained by the endoscope 1 (i.e., from an observed image) and displays this created image.

A connecting portion 81 that is shaped like a truncated cone that narrows as it approaches the insertion portion 11 is provided at one end of the gripping portion 10 and is connected to a base end portion 11d of the insertion portion 11. In addition, of the portion where the one end of the gripping portion 10 is in contact with the connecting portion 81, a setting down portion 80 is formed on the side thereof where the distal end portion 20a of the bending operation lever 20 is provided.

The image display unit 3 is substantially shaped as a rectangular parallelepiped and is removable provided at the other end of the operation portion 12. It is fitted onto the other end of the operation section 12 at least while an observation is being made.

A display element 37 such as an LCD or the like that converts observed pictures of an object into images and then displays them is provided in the image display unit 3 so that the display surface is exposed to the outside. The display surface of the display element 37 is a screen that has a larger surface area than the image pickup element 4 and the condensing lens 4a and the like in order that it is always easily viewed. Therefore, in the present embodiment, the display element 37 is provided on that surface of the rectangular parallelepiped that makes up the image display unit 3 that has the greatest surface area. This surface is large enough to cover a cross section orthogonal to the longitudinal axis of the operating section 12. Accordingly, as is shown in FIG. 32, when the image display element 3 is fixed such that the direction faced by the display element 37 is substantially parallel to the direction of the optical axis of the endoscope 1, then the image display unit 3 and the operating section 12 form a T-shape irrespective of which direction intersecting the optical axis they are viewed from.

Figure 35:
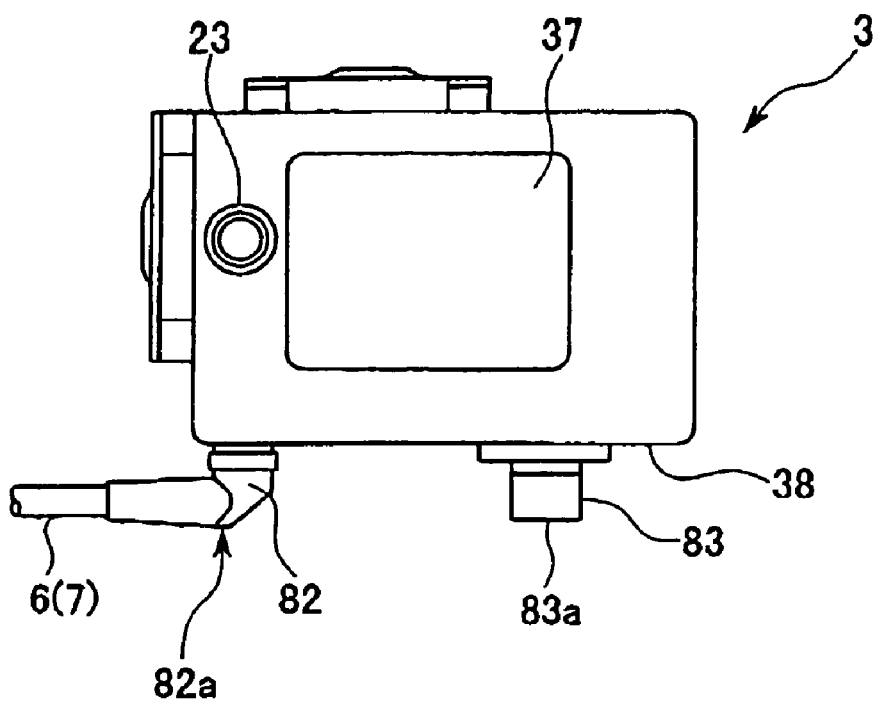
FIG. 35 is a frontal view to illustrate the structure of an observation section of the endoscope system of the sixth embodiment.

As is shown in FIG. 35, the startup switch 23 that starts up the endoscope system, the connector 82 (i.e., a connector component), and a foot portion 83 are provided on an external side of the image display unit 3.

The connector 82 is used to connect the power supply cable 6 which is an external cable and the collection cable 7 which is an external cable (described below) to the image display unit 3. In addition, the connector 82 is provided so as to protrude above a display unit bottom surface 38 that is located below the screen of the display element 37, and is bent in an L-shape such that the power supply cable 6 and the collection cable 7 can be guided towards the outer side in the horizontal direction of the display unit bottom surface 38.

A connector setting down portion 82a (i.e., a setting down portion) where the height to which the connector 82 protrudes from the display unit bottom surface 38 in the vicinity of the bend portion is at its greatest is provided in the connector 82. Because of this, if the image display unit 3 or the endoscope 1 including the image display unit 3 is put down such that the display unit bottom surface 38 is facing a suitable setting down surface, then at least a portion of the connector setting down portion 82a is in contact with this setting down surface. As a result, the power supply cable 6 and the collection cable 7 are guided in a horizontal direction between the setting down surface and the display unit bottom surface 38.

Note that the connector 82 may be fixed to the image display unit 3, or it may be removably connected to the image display unit 3. In addition, in order to provide a smooth set down and to prevent slippages, it is preferable that at least the connector setting down portion 82a is covered by synthetic rubber or a soft synthetic resin.

In addition, the connector 82 is formed in an L-shape such that the power supply cable 6 and the collection cable 7 do not get in the way when the image display unit 3 is put down. However, this structure also has the advantage that, in the state shown in FIG. 32, when the bending operation lever 20 is turned towards the operator and the operator grips the gripping portion 10 while operating the bending operation lever 20, the power supply cable 6 and the collection cable 7 protrude towards the operator and do not obstruct operations.

The foot portion 83 is a projection that protrudes above the display unit bottom surface 38 at a suitable distance from the connector 82. A foot portion setting down surface 83*a* (i.e., a setting down portion) is formed in this protrusion direction. The height to which the foot portion setting down surface 83*a* protrudes from the display unit bottom surface 38 is substantially the same as the height of the connector setting down portion 82*a*.

Note that, in the foot portion 83, in order to provide a smooth set down and to prevent slippages, it is preferable that at least the foot portion setting down surface 83*a* is covered by synthetic rubber or a soft synthetic resin.

Moreover, in the drawings, the foot portion setting down surface 83*a* is formed as a flat surface and the foot portion 83 is formed in a columnar shape, however, this is just one example and, provided that there is a projection from the display unit bottom surface 38, then other configurations may also be used. For example, the foot portion 83 may be formed in a cone shape and a point-shaped setting down portion may be formed by the apex thereof so that the setting down location is fixed. Neither is it essential for the setting down portion to have a planar shape.

As is shown in FIG. 32, a bracket 1*b* is provided on a top portion of the endoscope 1, and brackets 3*a* are provided at a bottom portion of the image display unit 3. These brackets 1*b* and 3*a* are fastened by fastening bolts 8. The orientation of the screen of the image display unit 3 can be tilted towards the bending operation lever 20 side by loosening the bolts 8 if this is required during an operation or an observation, and the screen can then be fixed in a desired position within the range of movement by then refastening the bolts 8.

As has been described above, in the endoscope 1, the image display unit 3 is provided at an end portion of the operating section 12 and various components are provided on the outer circumferential surface. In addition, the power supply cable 6 and the collection cable 7 are also connected. As a result, if the endoscope 1 is placed casually on a desktop or the like, there is a possibility that the image display unit 3 will receive a shock, or that the delicate components will be damaged or receive a shock, or that a load will be applied to the cables. Alternatively, there is a possibility that the operating lever and operating switches will malfunction. Moreover, in some case the endoscope may fall off after being placed in an unstable manner.

Therefore, in the present embodiment, it is possible to avoid situations like those described above by putting down the endoscope such that the three setting down portions, i.e., the connector 82, the foot portion 83, and the setting down portion 80 are set down on a setting down surface.

Figure 36:
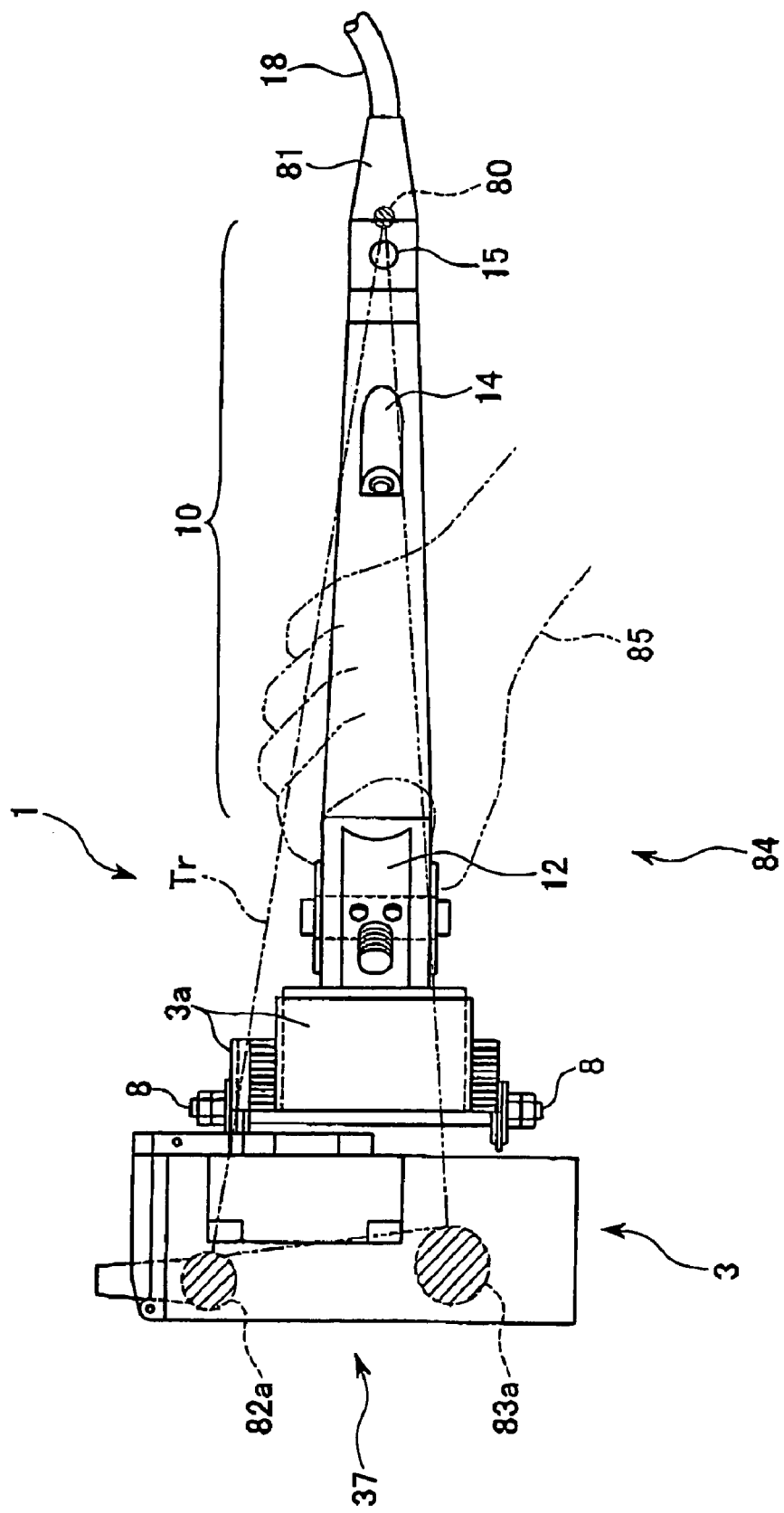
FIG. 36 is a plan view to illustrate a method of placing the endoscope system of the sixth embodiment on a surface.
Figure 37:
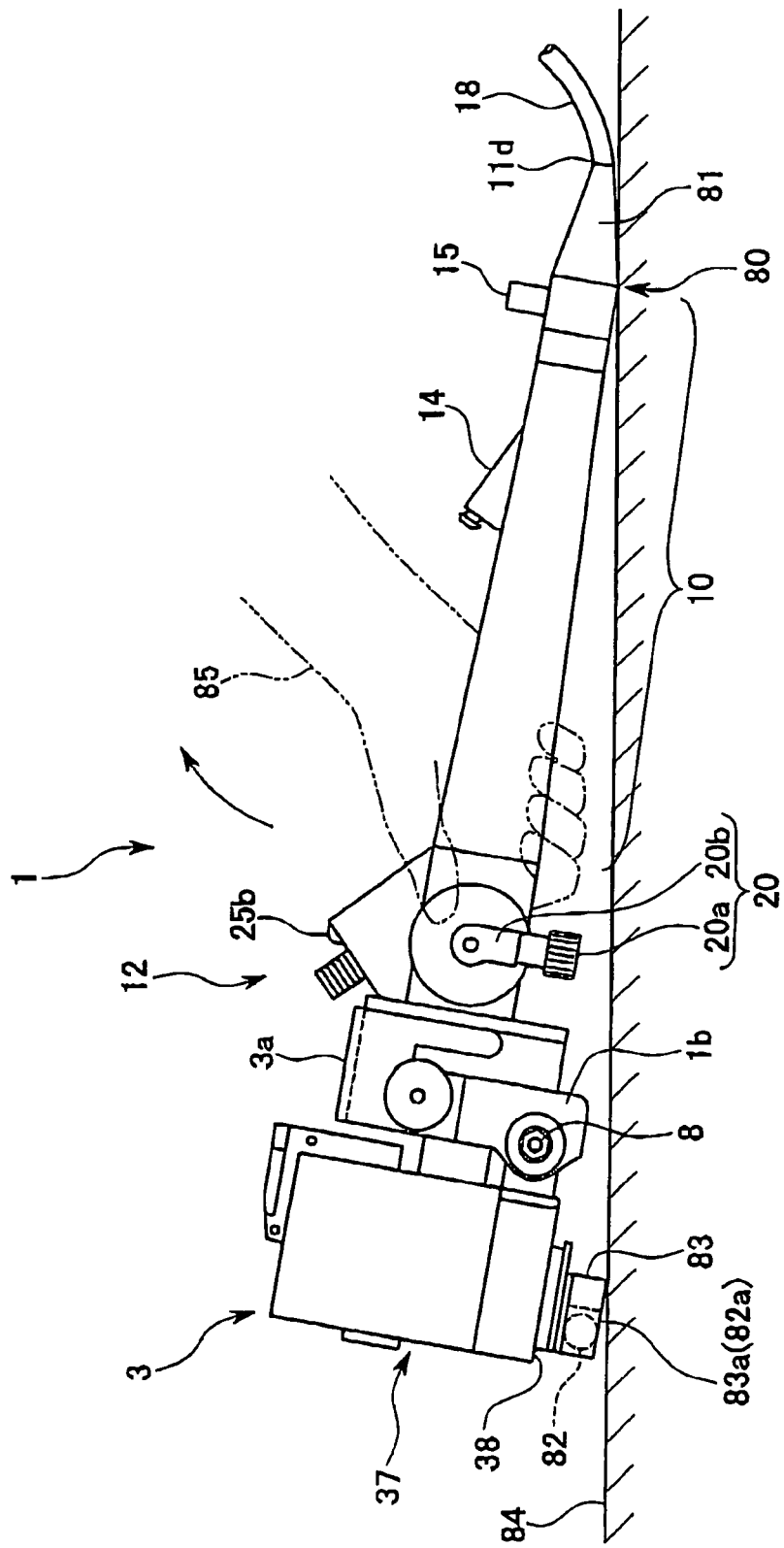
FIG. 37 is a plan view to illustrate a method of placing the endoscope system of the sixth embodiment on a surface.

In the present embodiment, as is shown in FIG. 36 and FIG. 37, the image display unit 3 is fixed such that the image display unit 3 and the operating section 12 form a T shape. In this state, the connector 82 and the foot portion 83 that protrude from the display unit bottom surface 38 are positioned on the outer side in the radial direction of the operating section 12. In addition, the endoscope 1 placed on a setting down surface 84 with the connector setting down portion 82*a* and the foot portion setting down surface 83*a* facing towards the setting down surface 84.

Consequently, as is shown in FIG. 37, the connector setting down portion 82*a* and foot portion setting down surface 83*a* as well as the setting down portion 80 that is located on the same side as these two are in contact with the setting down surface 84. These positions that are set down on the setting down surface 84 are separated from each other on the setting down surface 84 and are also not on the same straight line. As a result, a triangle Tr (refer to FIG. 36) that joins the three is formed. Namely, the three setting down portions are placed in a triangle.

Accordingly, by providing the triangle Tr within such a range that the center of gravity of the image display unit 3 and the endoscope 1 excluding the insertion portion 11 falls within a triangle-shaped range, the image display unit 3 and endoscope 1 can be placed stably on the setting down surface 84 without them rolling off or being unsteady.

Here, because only a portion of these setting down portions is in contact with the setting down surface 84, and, moreover, because the setting down area is extremely small in proportion to the area of the triangular placement, it is possible to regard the contact as being analogous to a point contact. Because of this, the support is essentially a three-point support so that even if, for example, a small amount of unevenness is present in the setting down surface 84, the image display unit 3 and endoscope 1 can be placed stably.

In contrast, in the frontal view shown in FIG. 37, the connector setting down portion 82*a* and the foot portion setting down portion 83*a* protrude from the display unit bottom surface 38 that is positioned at one end in the extension direction of the image display unit 3 which extends so as to form a T shape together with the operating section 12. As a result, the operating section 12 is tilted relative to the setting down surface 84 and a schematic right-angle triangle-shaped gap is formed between the operating section 12 and the setting down surface 84. Accordingly, the components such as, for example, the bending operation lever 20 and the bracket 1*b* that are provided on an outer circumference of the operating section 12 are not in contact with the setting down surface 84. Accordingly, such components do not strike against the setting down surface 84 and become damaged, or receive shocks, or malfunction. Because of this, it is possible to improve the reliability of the endoscope 1. Moreover, because an operator does not need to exercise special caution over the placement of the endoscope 1 or the location where the endoscope is placed, the usability of the endoscope is greatly improved. The particular advantage is gained that this endoscope system is portable and can be carried around and favorably used in a variety of locations.

Moreover, by setting the space that is created between the operating section 12 and the setting down surface 84 to a suitable size, as is shown in FIG. 37, a space for gripping the gripping portion 10 using a hand 85 can be provided resulting in it being extremely easy to hold when the endoscope is picked up from a surface.

Note that the above description is of an example in which a set down portion is provided in two locations in the observation section and in one location in the operating section. If the observation portion is formed by the image display unit 3, as is the case in the present embodiment, and the observation section is comparatively large and heavy, then this type of placement is rational. However, the placement positions and the number thereof are not limited to these. Depending on the shape and mounting position and the like of the observation section and the operation section, it is also possible for all three to be located on one of the observation section and the operation section. For example, in cases such as when the observation section is formed by a small and lightweight eyepiece optical system, then it is possible for either one or no setting down portion to be provided in the observation section.

Moreover, the above description is of an example in which the connector 82 and the foot portion 83 protrude from the display unit bottom surface 38. In this case, when it is set down, the image on the display unit 37 can be viewed in an upright state, however, if the only intention is to place the apparatus stably on a setting down surface, then provided that a triangular placement is possible, it is unimportant where it is located on the image display unit 3 and the location is not restricted to the display unit bottom surface 38.

Moreover, the above description is of an example in which, because no component that should not come into contact with the setting down surface 84 is present in the vicinity of the setting down portion 80 on the operating section side, the outer circumferential surface itself of the operating section can be used for the setting down portion. However, in cases such as when the vicinity of the setting down portion needs to be raised above the setting down surface or such as when the outer circumferential surface of the operating section or observation section must be protected, then it should be understood that it is also possible to provide a setting down portion that protrudes to an appropriate distance above the outer circumferential surface.

Furthermore, the above description is of an example in which the power supply cable 6 and the collection cable 7 extend from one end of the connector 82, however, it is also possible for the connector component and the external cables to be removably connected.

Moreover, the connector component is not limited to one to which external cables are always connected.

For example, it is also possible to provide a connection port so that the external cables can be disconnected when the apparatus is set down and connected when an operation or observation is being performed. In this case, a structure can be employed in which a cap component made of synthetic rubber or soft synthetic resin or the like that covers the setting down portion is removably fitted or else a configuration such as the foot potion 83 can be provided so that the connection port is not damaged when the apparatus is set down.

Seventh Embodiment

The seventh embodiment of the present invention will now be described using FIG. 38 through 57. Note that component elements that have previously been described in the above embodiments are given the same symbols and a description thereof is omitted.

Figure 38:
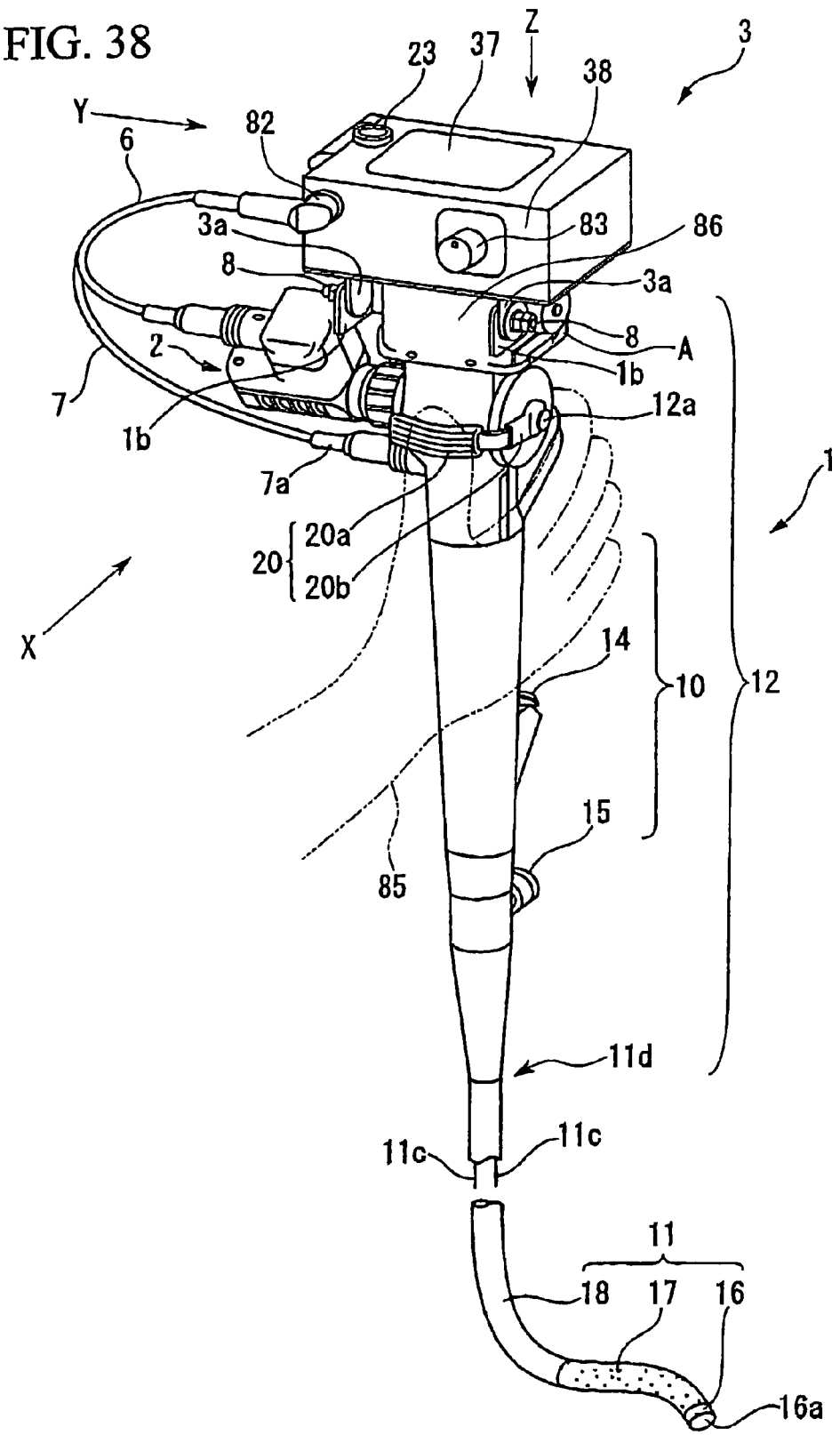
FIG. 38 is a perspective view to illustrate an endoscope system of the seventh embodiment of the present invention.
Figure 39:
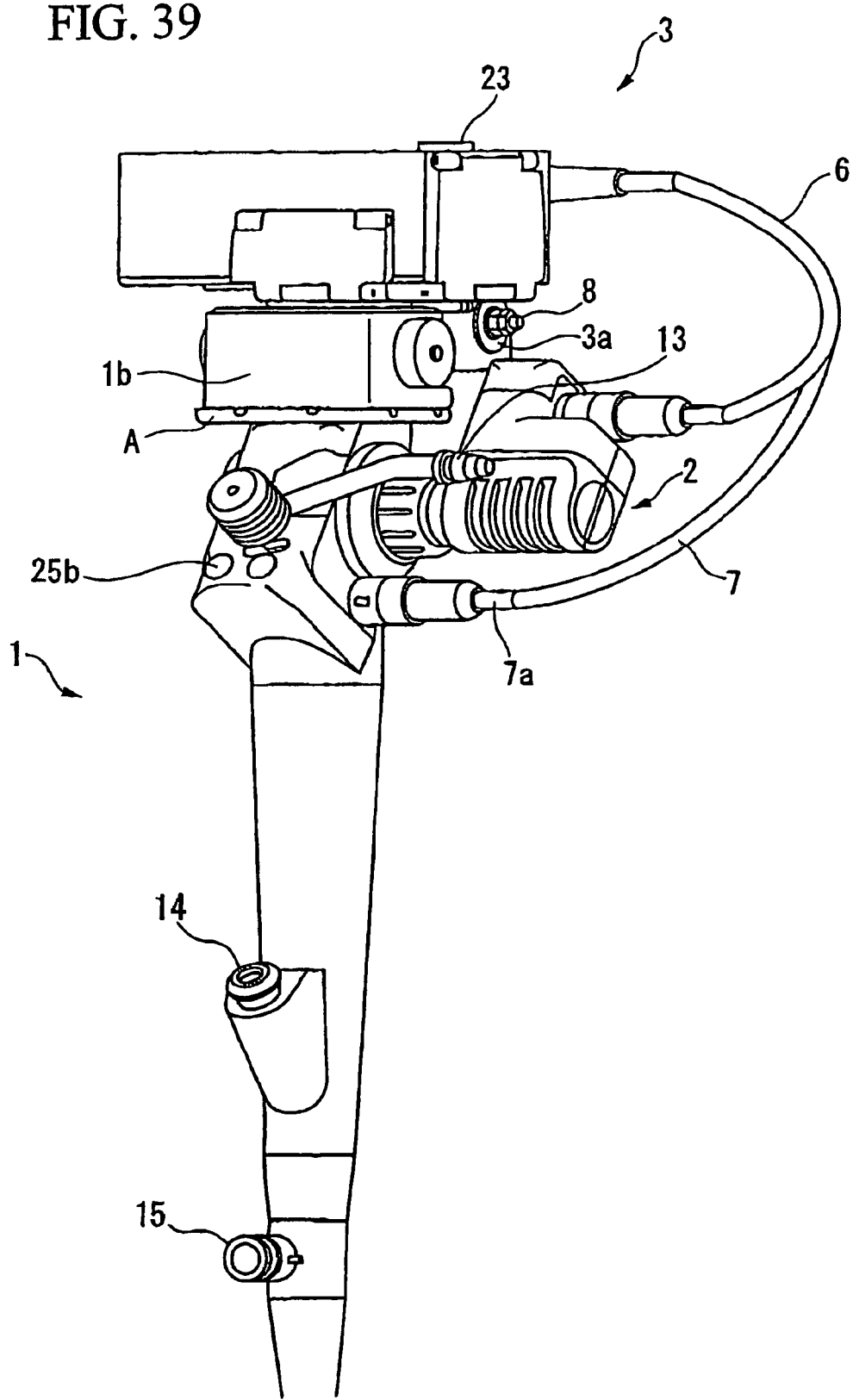
FIG. 39 is a perspective view looking from a different direction from that in FIG. 1 of the endoscope system of the seventh embodiment.
Figure 40:
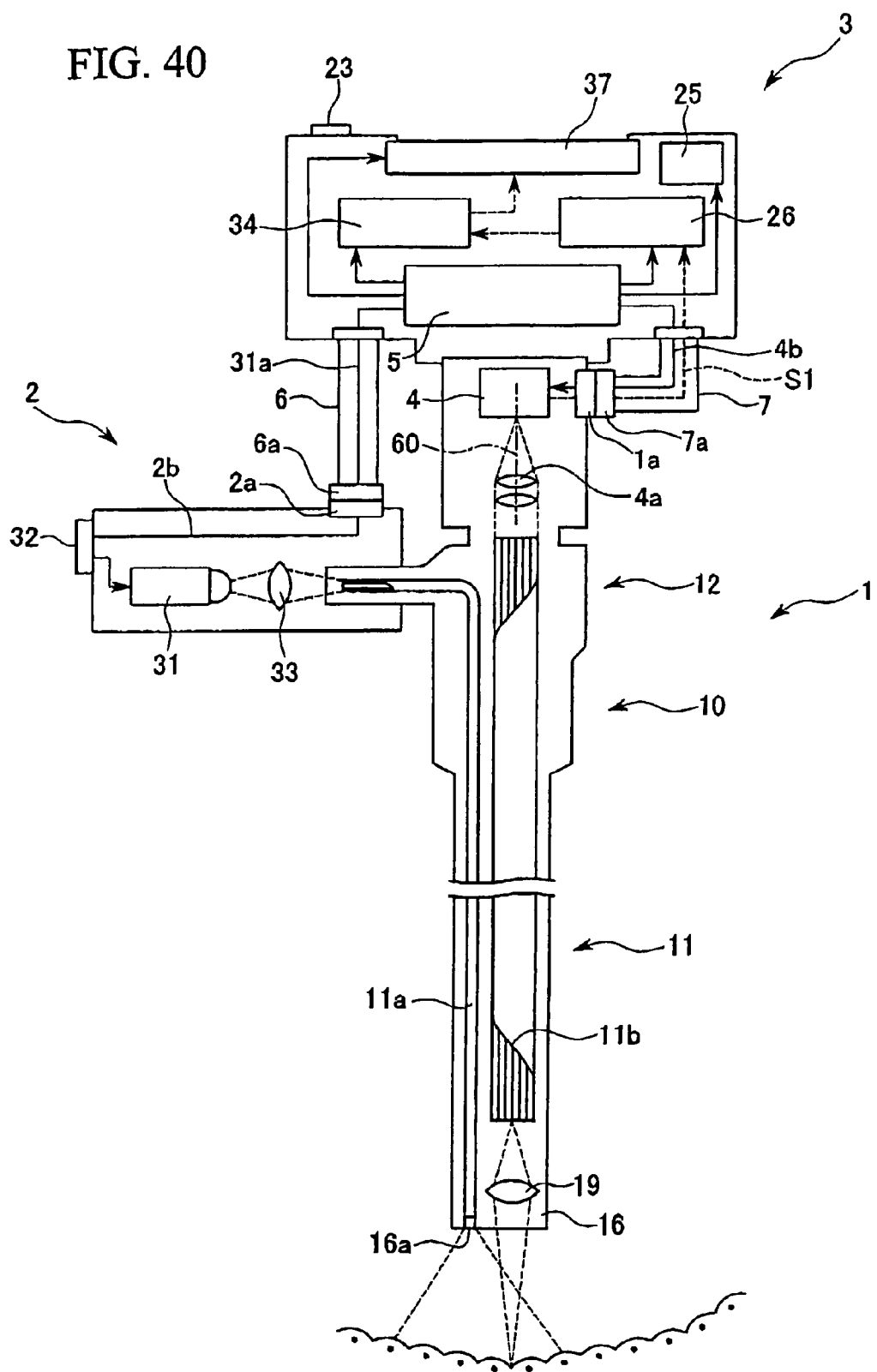
FIG. 40 is a typical view to schematically illustrate the internal structure of the endoscope system of the seventh embodiment.

As is shown in FIG. 38 through FIG. 40, the principal component elements of the endoscope system of the present embodiment are the endoscope 1, a light source apparatus 2 that generates illumination light for illuminating an object, and an image display unit 3 (i.e., a display device) that creates an image (i.e., an observation image) from the image of the object obtained by the endoscope 1 and displays this created image. Note that the X, Y, and Z directions in FIG. 38 are three axes that are perpendicular to each other, and, for the sake of convenience, directions may be referred to using these X, Y, and Z directions.

As is shown in FIG. 38, in the endoscope 1, an optical path from an image guide 11b that is placed inside the insertion portion 11 to the image pickup element 4 may be folded if this is appropriate, however, in the present embodiment, the condenser lens 4a and the image pickup element 4 are placed on an optical axis 60.

On one end side of the operating section 12 the gripping portion 10 is connected to the base end portion 11d of the insertion portion 11, while a display unit mounting portion 86 that is used to mount the image display unit 3 (described below) is provided at the other end side (i.e., on the top side in FIG. 38) that is adjacent to the bending operation lever 20. A display unit receiving surface 87 (refer to FIG. 41 and FIG. 42) that is used to receive the image display unit 3 in a direction that is substantially orthogonal to the optical axis 60 is provided at an end surface (i.e., on the top side in FIG. 38) of the display unit mounting portion 86. A convex portion 88 is provided at a bottom portion on an opposite side from the end surface of the display unit mounting portion 86.

As is shown in FIG. 38, on the external side of the image display unit 3 there are provided a startup switch 23 that is used to start up the endoscope system, a connector 82 that connects the power supply cable 6 which is an external cable and the collection cable 7 which is an external cable (described below) to the image display unit 3, a foot portion 83, and brackets 3a (i.e., support portions).

The connector 82 is provided so as to protrude above the display unit bottom surface 38 which is positioned below the screen of the display element 37, and is bent in an L shape such that the power supply cable 6 and the collection cable 7 can be guided to the external side in a horizontal direction of the display unit bottom surface 38. The foot portion 83 is a projection that protrudes above the display unit bottom surface 38 at an appropriate distance from the connector 82. The brackets 3a protrude from a display unit rear surface 39 which corresponds to the rear surface side of the display screen of the display element 37, and supporting shafts 8 each protrude towards the outside through a pair of parallel plates that are positioned in the vicinity of the display unit bottom surface 38. The brackets 3a and 3a are separated by a large enough space to allow the display unit mounting portion 86 to be sandwiched between them. From the distal end side of a supporting shaft 8 are formed in this order a threaded portion 8a and a shaft portion 8b (refer to FIG. 46) and the two shaft portions 8b are positioned so as to have the same axis.

A bracket 1b (i.e., a supporting portion) that can be fitted and removed is provided on the display unit mounting portion 86, and a supporting portion is formed that is able to rotatably support the image display unit 3 as a result of the brackets 3a and 3a being rotatably engaged with the bracket 1b.

Figure 41:
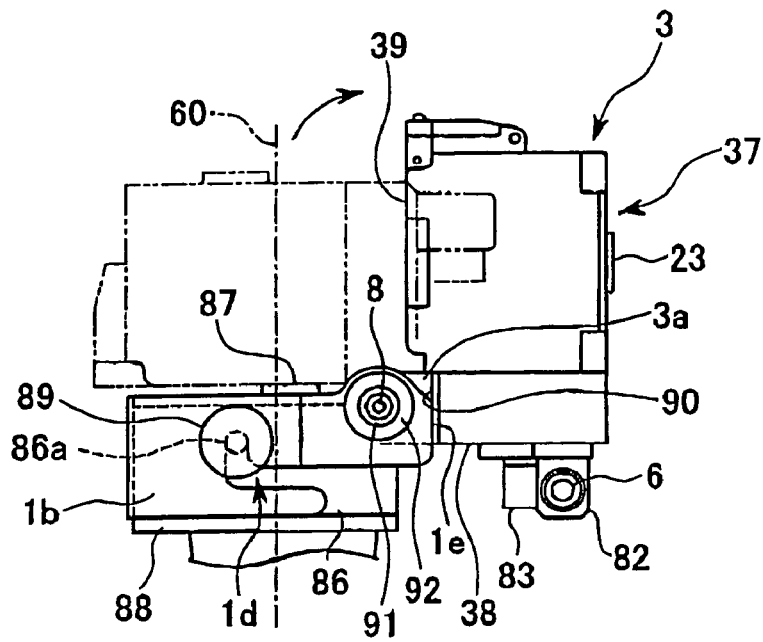
FIG. 41 is a view from the left side showing a supporting portion of the endoscope system of the seventh embodiment.
Figure 42:
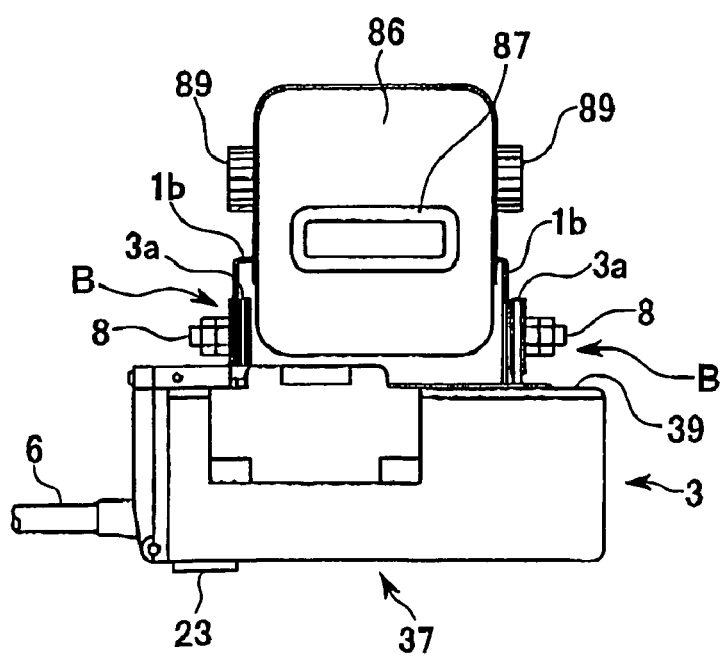
FIG. 42 is a plan view showing the supporting portion of the endoscope system of the seventh embodiment.
Figure 43:
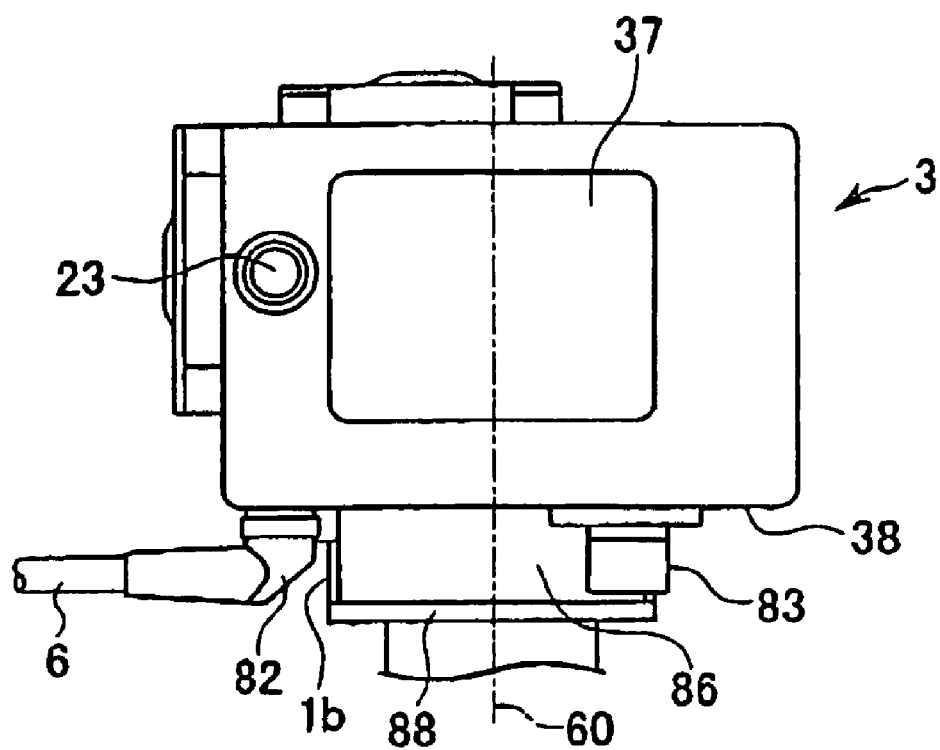
FIG. 43 is a frontal view showing the supporting portion of the endoscope system of the seventh embodiment.

FIG. 41, FIG. 42, and FIG. 43 are a left side view, a plan view, and a frontal view illustrating the supporting portion of the present embodiment Unlike FIG. 38, a state in which the display element 37 is rotated such that it can be viewed front on from the X direction shown in FIG. 38 is represented by the solid line. The placement of the image display unit 3 in FIG. 38 is shown by the double dot chain line in FIG. 41.

The bracket 1b is formed substantially in a U shape when seen in plan view such that it can be engaged at the side surfaces of the display unit mounting portion 86. Shaft holes 1c (refer to FIG. 46) that can be fitted smoothly together with the shaft portions 8b are provided at both distal end portions of the open side of the U shape. Moreover, as is shown in FIG. 41, L-shaped grooves 1d that are open in a horizontal direction and whose innermost portion then curves in a vertical direction are provided in each side surface of the open side of the U shape. The L-shaped grooves 1d engage with an engaging shaft 86a that protrudes from the display unit mounting portion 86. In addition, a bottom end portion of the bracket 1b (refer to FIG. 41) engages from above as is shown in the drawing with the convex portion 88 of the display unit mounting portion 86 so that movement downwards is restricted and so that, consequently, there is no rotation around the engaging shaft 86a. A male thread is formed on distal ends of the engaging shaft 86a and fixing components 89 that can be screwed onto the male thread can be removably attached. As a result, after the bracket 1b has been installed on the display unit mounting portion 86, it can be fixed in place by the fixing members 89. If required, the bracket 1b can also be later removed.

Figure 44:
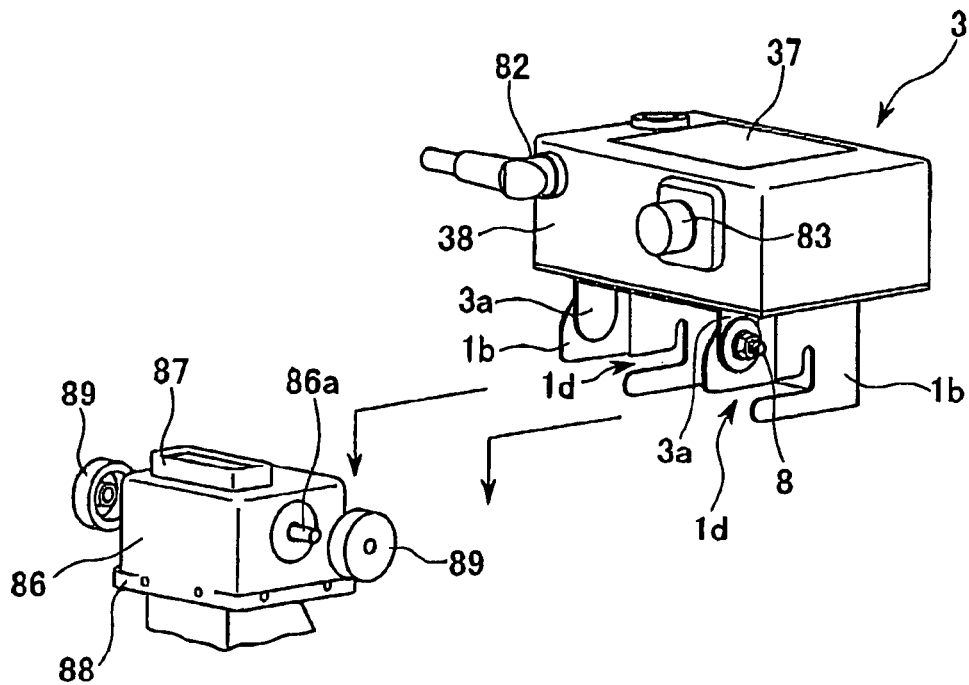
FIG. 44 is an exploded perspective view showing a state when the supporting portion of the endoscope system of the seventh embodiment is attached to an operating portion.
Figure 45:
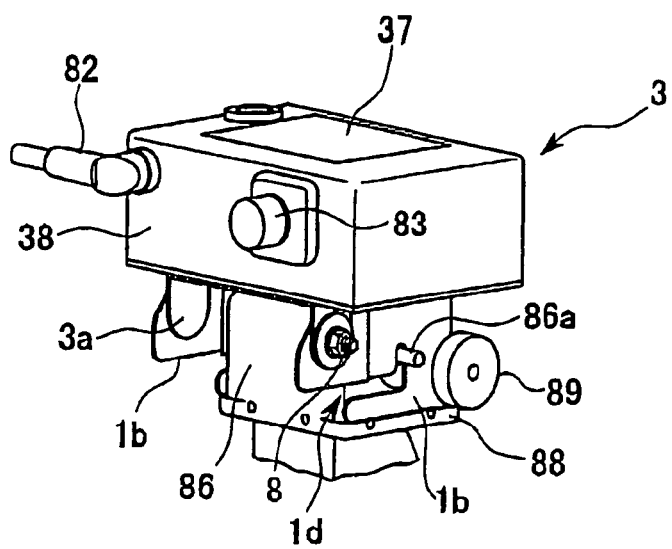
FIG. 45 is a perspective view showing state when the supporting portion of the endoscope system of the seventh embodiment is attached to the operating portion.

As is shown in FIG. 44, in order to mount the bracket 1b on the display unit mounting portion 86, the engaging shaft 86a is inserted through the aperture side in the engaging groove 1d, the bracket 1b is then moved in the horizontal direction shown in the drawings and is then pushed vertically downwards through the groove in the innermost portion of the engaging groove 1d, so as to be engaged with the display unit mounting portion 86 (refer to FIG. 45). The image display unit 3 is stably anchored by its own weight in this attitude on the display unit receiving surface 87 (refer to FIG. 44). Movement in a horizontal direction is also restricted by the groove on the inner side of the engaging groove 1d.

Accordingly, in this state, because there is no shift in the state of engagement of the image display unit 3 even if the gripping portion 10 is tilted, the advantage is obtained that the fixing components 89 can be screwed on with ease. Moreover, when the image display unit 3 is being removed, because it is not possible to remove it without undoing the fixing components 89 and then gripping the image display unit 3 and moving it along the engaging groove 1d, the advantage is obtained that, even if the fixing components 89 are undone, it is still possible to prevent the image display unit 3 from falling spontaneously due to its own weight or the like. Furthermore, even if the fixing components 89 are fixed only loosely by mistake, it is still difficult for the image display unit 3 to drop.

As regards the direction in which the bracket 1b is mounted, the center axis of the shaft hole 1c is positioned in a direction that intersects the longitudinal direction of the gripping portion 10. In the present embodiment, the direction is approximately 90 degrees to the optical axis 60, and is also substantially parallel with the shaft 12a which is the rotation shaft of the bending operation lever 20.

Figure 46:
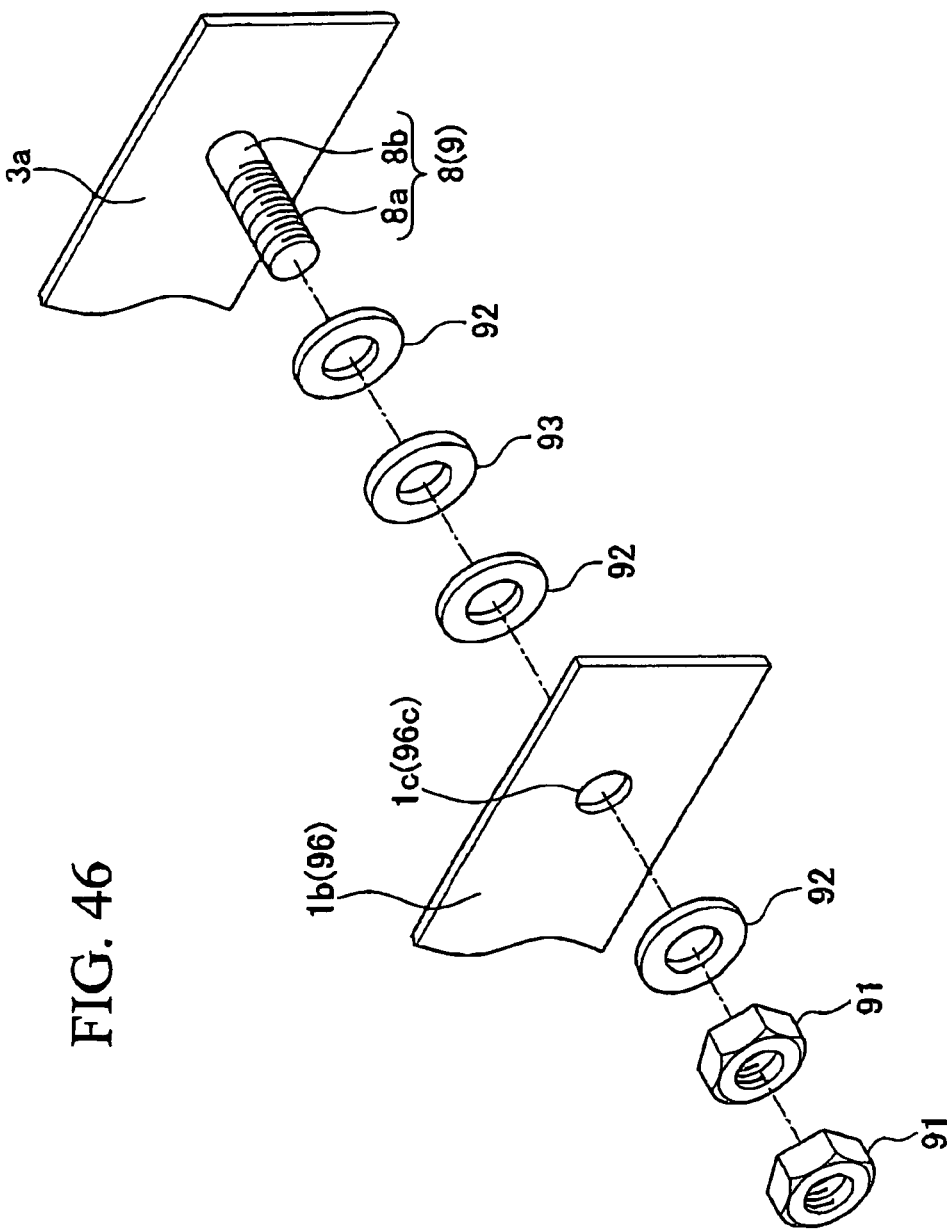
FIG. 46 is an exploded perspective view to illustrate in typical view a B portion of the endoscope system of the seventh embodiment that is shown in FIG. 4.
Figure 47:
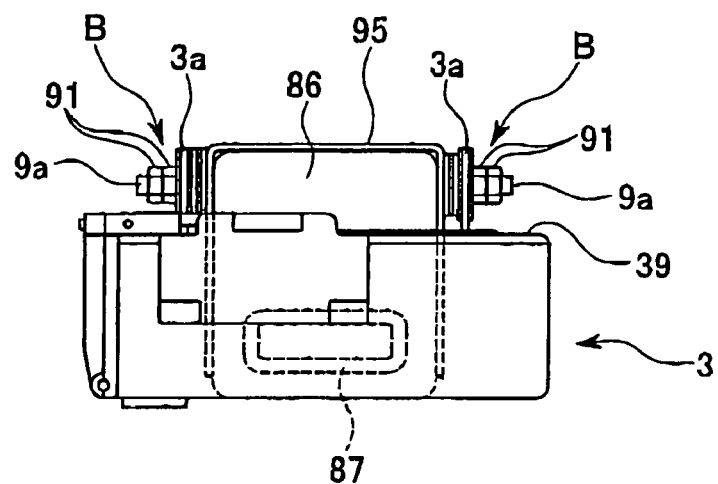
FIG. 47 is a plan view of an area adjacent to a display unit to illustrate the structure of a modification of the endoscope system of the seventh embodiment.

As is shown in FIG. 46, the brackets 3a and the bracket 1b are fixed by inserting the supporting shaft 8 into the shaft holes 1c sandwiching in this order a washer 92, a rubber plate 93, and a washer 92. A washer 92 is then placed over the threaded portion 8a as it protrudes from the shaft hole 1c and nuts 91 are then screwed onto the threaded portion 8a. Accordingly, the display unit 3 is able to rotate around a rotation shaft that is restricted by the supporting shaft 8 and the shaft hole 1c that are positioned coaxially.

The force used to fasten the nuts 91 is sufficiently large to suitably compress the rubber plate 93. The elastic repulsion force of the rubber plate 93 is adjusted so that the friction force in the rotation direction of the bracket 1b relative to the brackets 3a is a suitable value. As a result, the image display unit 3 can be held stationary at a desired position in the rotation direction by this friction force. However, it is also possible for the nuts 91 to be fastened tight when the image display unit 3 has been rotated to a particular position, and for them to be loosened when the orientation of the image display unit 3 is to be changed. In this case, it is preferable that an easily used structure is employed such as providing levers or knobs where these are required.

In an endoscope system that is structured in the manner described above, the image display unit 3 is provided such that it can be attached to or removed from the display unit mounting portion 86 via the bracket 1b. Accordingly, when the endoscope system is being transported the image display unit 3 can be removed so that the system is stored at a compact size. Moreover, during operations and observations, observations can be made within reach of the operator by installing the image display unit 3 in the operating section 12.

In the initial stage of an operation, in order to make it possible for the image display unit 3 to be transported in a compact size, as is shown by the double dot chain line in FIG. 41, the image display unit 3 can be pushed over such that the display unit rear surface 39 is in contact with the display unit receiving surface 87. This is the same state as that shown in FIG. 38. This state will now be described as the reference position of a rotation angle of 0 degrees. In this state, the display screen of the display element 37 is placed substantially orthogonal to the longitudinal direction of the gripping portion 10 and is placed favorably for an operator to make an observation from the Z direction in FIG. 38.

When gripping the gripping portion 10 and operating the bending operation lever 20, the manner in which the gripping portion 10 is gripped may be changed in accordance with requirements, however, as is shown in FIG. 38, gripping the gripping portion 10 using the four fingers while the thumb is facing towards the display unit mounting portion 86 side and the flat part of the thumb is pressed against the distal end portion 20a provides the greatest ease of operation. At this time, if the thumb is made to face upwards as is shown in the drawing and the gripping portion 10 is gripped in front of the operator, then the body of the operator ends up facing in the X direction in the drawings. In this case, because the operator must lower their head and look at the display element 37 from above (i.e., in the Z direction in FIG. 38), there is a possibility of the operator's neck becoming fatigued before the observation has ended.

In the present embodiment, in cases such as this, as is shown in FIG. 41, it is possible to rotate the image display unit 3 in the direction of the arrow by, for example, 90 degrees, and make the display screen of the display element 37 face towards the operator. Because the display screen is made to face directly towards the operator as a result of this, it is in an easily visible position. Namely, the operator is able to observe from the X direction in a comfortable forward-facing posture without bending their neck. Accordingly, the operator can adopt a posture that prevents them from becoming tired even if the observation takes considerable time.

The angle of rotation from the reference position is not limited to 90 degrees and may be an acute angle or an obtuse angle where this is necessary. For example, if the insertion portion 11 side is made to face forwards in the X direction from the state shown in FIG. 38 and is tilted 45 degrees from the vertical axis and then gripped, then if the image display unit 3 is rotated 45 degrees towards the operator, the display screen faces directly towards the operator in the same way as is described above. Accordingly, it has an easily viewed orientation. Moreover, if the operator is able to easily view the display screen, then it is not essential for the display screen to be oriented so as to face directly towards the operator. For example, if the orientation is set to an angle that causes less surface reflection on the display screen, or, if a liquid crystal screen is being used, to an easily viewed angle such as one that is within an appropriate angle of visibility, then even if the display screen is tilted away from a direct frontal direction, the orientation still provides good visibility. However, it is preferable that the angle of rotation can be suitably restricted in order, for example, to prevent the center of gravity of the endoscope system shifting due to the rotation of the image display unit 3 and it consequently becoming difficult to obtain a good grip.

In the present embodiment, a rotation restricting portion 1e is provided that cuts across the end portions of the open side of the bracket 1b in the direction of the optical axis 60. When the image display unit 3 is rotated 90 degrees, an engaging portion 90 that is provided on the display unit rear surface 39 side engages with the rotation restricting portion 1e and prevents any further rotation. By altering the configurations of the rotation restricting portion 1e and the engaging portion 90, the limit of the angle of rotation that is being restricted can be suitably altered.

Due to the structure of the wrist joint and the like, when gripping the operating section 12 as is described above, a range of rotation whose center is the longitudinal direction of the gripping portion 10 is comparatively narrow. Moreover, during actual use, in order to make observation easier, it is almost always necessary for an operator to change their grip so as to change the orientation of the longitudinal direction of the gripping portion 10. In the present embodiment, when the display screen is held using the above described grip, the orientation of the display screen can be rotated in a direction that intersects the longitudinal direction of the gripping portion 10 and the display screen can be rotated towards the operator. Therefore, in most cases, the display screen can be made to face in an easily viewed direction. Accordingly, compared with when the display screen cannot be rotated, there is a huge improvement in operability.

Next, a modification of the present embodiment will be described.

In this modification, instead of the bracket 1b of the above described embodiment, a bracket 95 (i.e., a supporting portion) is provided, and two plate-shaped arms 96 (i.e., arm components) that are provided with a shaft hole 96c the same as the shaft hole 1c at an end portion in the longitudinal direction thereof are provided between the brackets 3a and the bracket 95. Elements of this modification that are different from those in the above described embodiment are mainly described below.

The brackets 3a differ from the above described embodiment in that, instead of the supporting shaft 8, they have a supporting shaft 9a (i.e., a second rotation supporting portion) that fits smoothly in the shaft holes 96c.

Figure 48:
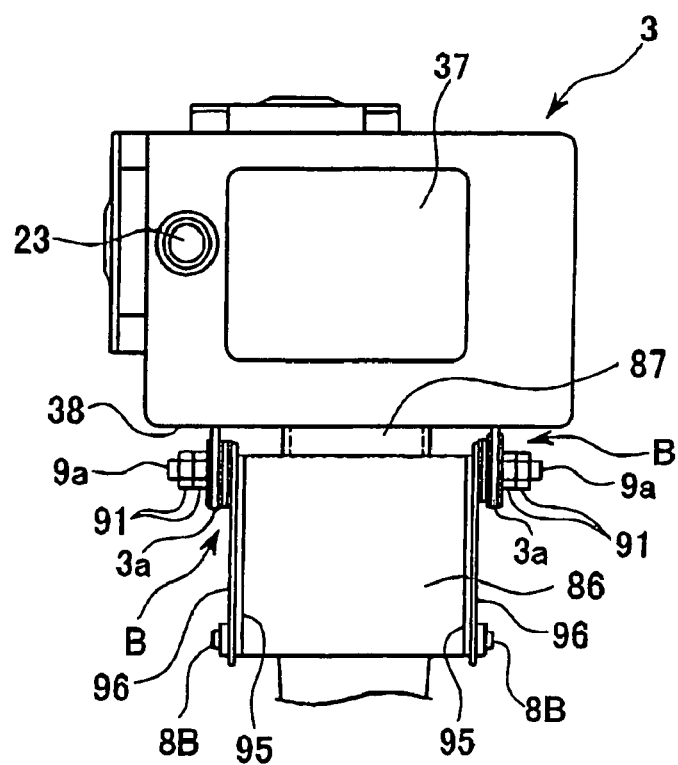
FIG. 48 is a frontal view of an area adjacent to a display unit to illustrate the structure of the modification of the endoscope system of the seventh embodiment.
Figure 49:
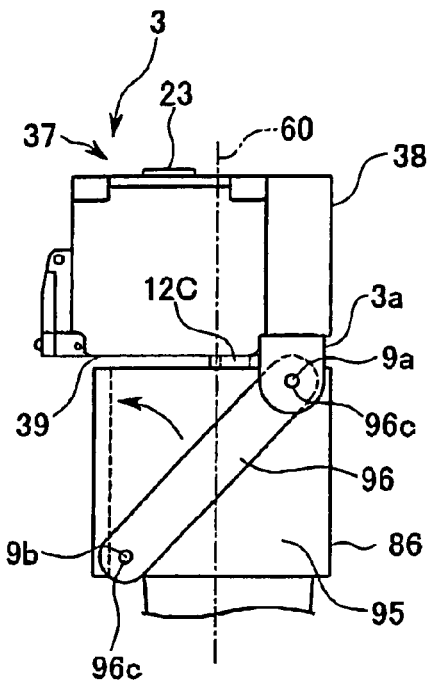
FIG. 49 is an operating diagram showing a left side surface to illustrate an operation of the above described modification.

As is shown in FIG. 48, the bracket 95 is formed substantially in a U shape when seen in plan view such that it can be engaged at the side surfaces of the display unit mounting portion 86. Moreover, as is shown in FIG. 49, supporting shafts (i.e., first rotation supporting portions) 9b are provided on the same axis as each other on the bend side of the U shape on the two side surfaces that form the opening of the U shape. The supporting shafts 9b are shaft components that fit smoothly into shaft holes that are provided in end portions of the arms 96, and the same structure may be employed for these as is employed, for example, for the supporting shaft 8.

The bracket 95 is fixed by a suitable device to the display unit mounting portion 86. For example, as in the above described embodiment, an engaging groove may be provided in the bracket 95 and an engaging shaft provided in the display unit mounting portion 86 thereby forming a fixing component for fixing the bracket 95. It is also possible to provide a threaded portion in the display unit mounting portion 86 and to fix the bracket 95 using bolts.

The arms 96 are connected such that the shaft holes 96c can rotate around the respective supporting shafts 9a and 9b. A rotation structure such as that shown in FIG. 46 can be employed for this, however, provided that rotation is possible, it is also possible for another rotation mechanism to be employed.

According to this type of structure, as is shown in FIG. 49, by positioning the arms 96 on the side surfaces of the brackets 95 such that they extend from the supporting shafts 9b diagonally towards the open side of the U shape, the image display unit 3 can be positioned in a compact manner substantially directly above the display unit mounting portion 86 with the display unit rear surface 39 in contact with the top of the display unit receiving surface 87.

Figure 50:
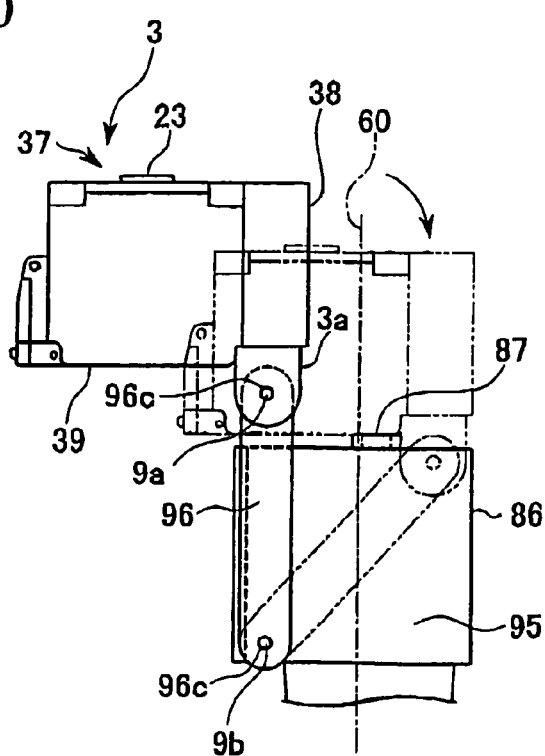
FIG. 50 is an operating diagram showing a left side surface to illustrate an operation of the above described modification.

Taking this state as a reference position, in order to rotate the display element 37 90 degrees towards the operator, firstly, as is shown in FIG. 50, the arms 96 are rotated anti-clockwise as seen in the drawing around the supporting shafts 9b and made to stand upright. As a result of this movement, the display unit rear surface 39 is able to move away from the display unit receiving surface 87.

Figure 51:
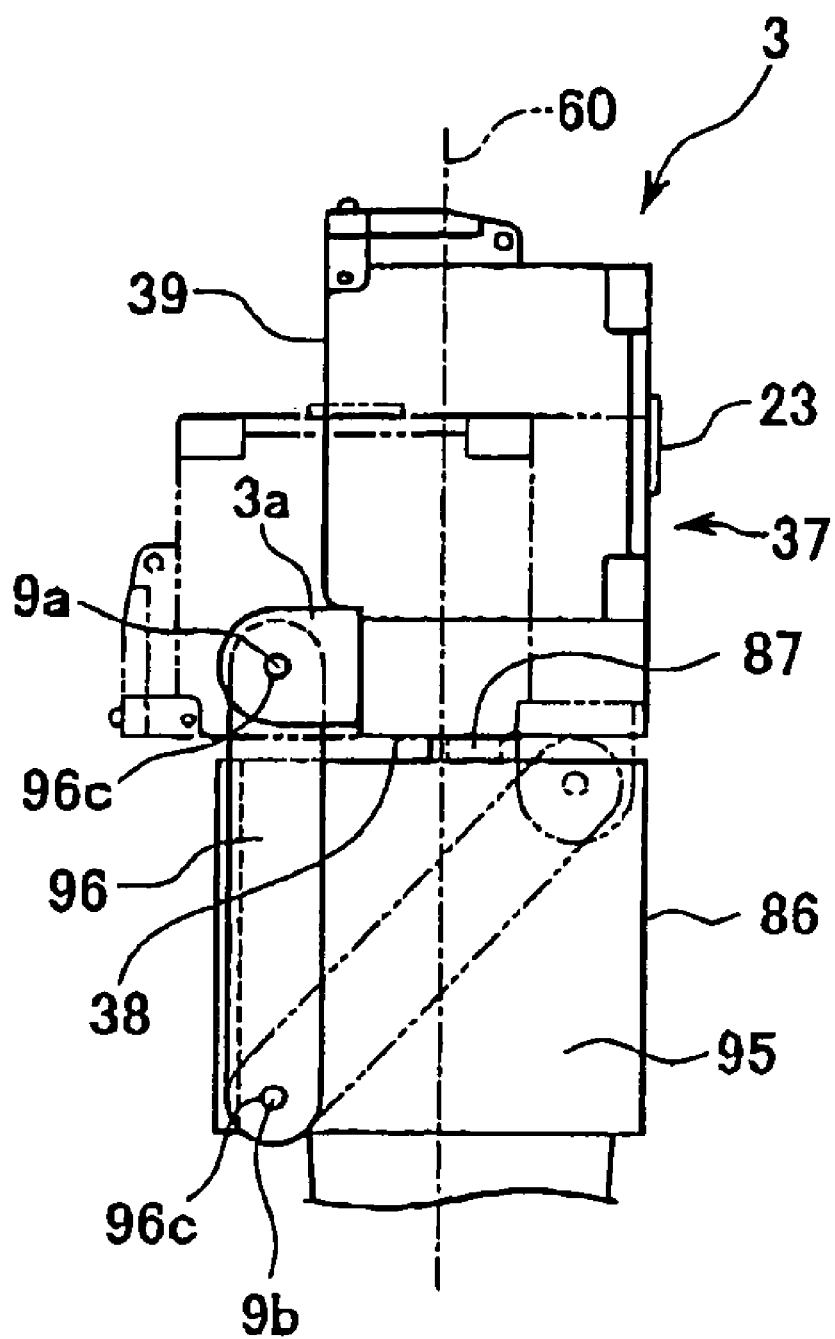
FIG. 51 is an operating diagram showing a left side surface to illustrate an operation of the above described modification.

Next, as is shown in FIG. 51, with the arms 96 left stationary, the image display unit 3 is rotated clockwise as seen in the drawing around the supporting shafts 9a. If the image display unit 3 is rotated 90 degrees, the display unit bottom surface 38 is placed in contact with the display unit receiving surface 87 and no further rotation is possible.

At this time, because the supporting shafts 9a are rotated while having been moved to the bend side of the U shape in the bracket 95, this rotation is executed in a space located above the display unit mounting portion 86. Because of this, the image display unit 3 can be positioned substantially directly above the display unit mounting portion 86 even when it is in contact with the display unit receiving surface 87. Namely, as in the case shown in FIG. 41, the image display unit 3 can be moved in a direction away from the optical axis 60 and prevented from moving into a space outside the display unit mounting portion 86.

In this manner, according to the present modification, the center of rotation is divided into two using the two parallel supporting shafts 9a and 9b, and after the supporting shafts 9b have been moved using the center of rotation of the supporting shafts 9a, the image display unit 3 can be rotated using a second rotation that is centered on the supporting shafts 9b. As a result, the placement and positioning of the image display unit 3 becomes comparatively free Because of this, the advantage is obtained that compact placement is made possible. Moreover, by adjusting the movement position of the image display unit 3, movement of the center of gravity in a direction orthogonal to the optical axis 60 is lessened. As a result, the advantage is obtained that it is possible to grip the endoscope in a stable manner and the endoscope is easy to hold and easy to operate. It is beneficial if this arm component is provided with an extendible and retractable structure as the structure can then be made mote compact and the degree of freedom when placing the image display unit 3 can also be raised.

An arm 100 which is a first modification of an arm component will now be described.

Figure 52:
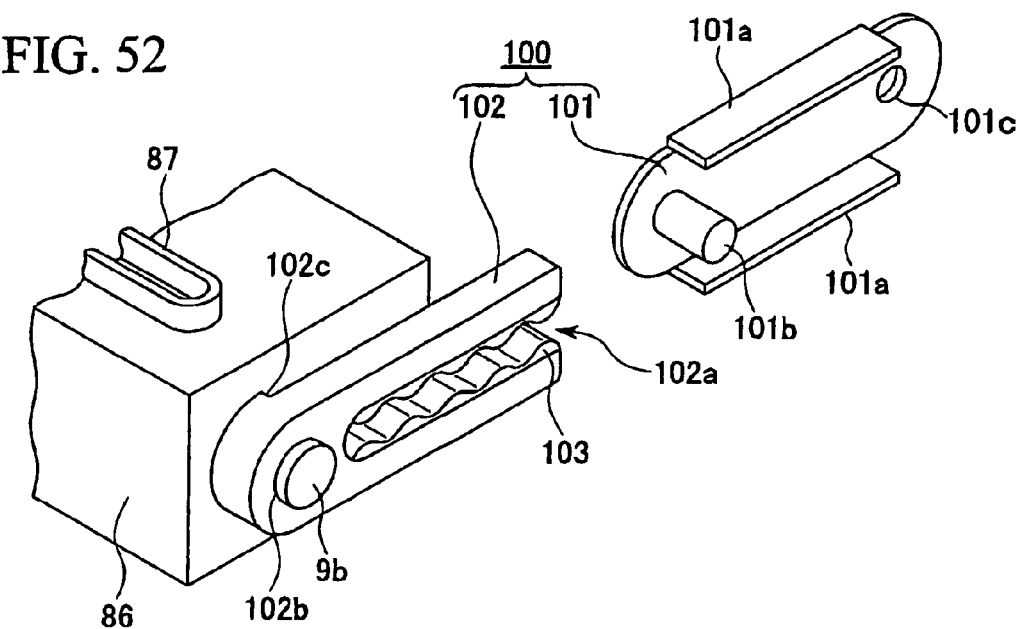
FIG. 52 is an exploded perspective view to illustrate a first modification of an arm component that is provided in the above described modification.

As is shown in FIG. 52, the arm 100 is formed by a sliding arm 101 and a fixed arm 102.

The sliding arm 101 has a shaft hole 101c formed at one end portion in the longitudinal direction thereof that is rotatably engaged with a supporting shaft 9a. A sliding shaft 101b protrudes from the other end portion and guide portions 101a that extend outwards in the direction in which the sliding shaft 101b protrudes are provided at the left and right in the longitudinal direction of the sliding arm 101.

The fixed arm 102 extends substantially in a U shape and a shaft hole 102b that rotatably engages with a supporting shaft 9b is provided in the curved portion of the U shape. A groove portion 102a that sandwiches the sliding shaft 101b is provided in the inner part of the U shape. Wave-shaped corrugated portions 103 that are made from a resilient component such as a plate spring and in which the corrugations face each other are provided in the groove portion 102a on the inner surfaces of the U shape of the fixed arm 102.

As a result, when the sliding shaft 101*b* is sandwiched in the groove portion 102*a*, the sliding shaft 101*b* can be held stationary at an appropriate position on the corrugations.

The transverse width of the fixed arm 102 fits inside the width formed by the guide portions 101*a* (refer to FIG. 54) and the sliding arm 101 is able to slide in the longitudinal direction.

A convex portion 102*c* that is in contact with the display unit mounting portion 86 is provided on the shaft hole 102*b* side of the fixed arm 102. Accordingly, a gap is formed for the sliding arm 101 to be sandwiched between the fixed arm 102 and a side surface of the display unit mounting portion 86.

Figure 53:
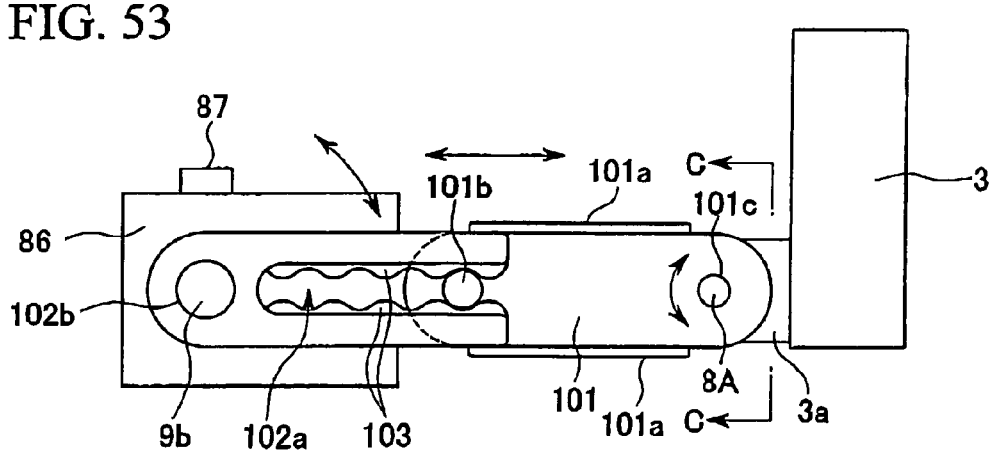
FIG. 53 is a frontal view to illustrate the first modification of the arm component that is provided in the above described modification.
Figure 54:
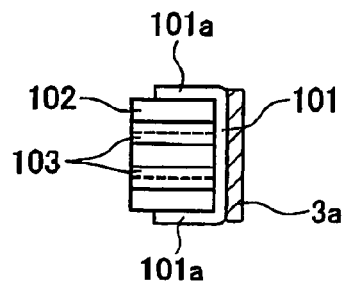
FIG. 54 is a cross-sectional view taken along a line C-C to illustrate the first modification of the arm component that is provided in the above described modification.

As is shown in FIG. 53, according to this type of arm 100, when the image display unit 3 is in a fixed state, it is possible to slide the sliding arm 101 in the longitudinal direction thereof inside the fixed arm 102 and fix its length at an appropriate holding position on the corrugated portions 103.

Accordingly, when moving the image display unit 3, the image display unit 3 can be moved easily by extending the arm 100, while when fixing the position of image display unit 3, the arm 100 can be retracted to the required length. As a result, the advantage is obtained that the image display unit 3 can be stored in a compact manner. Moreover, because the sliding shaft 101*b* is fixed by being nipped by the corrugated portions 103, it is not necessary for any task such as, for example, tightening screws to be performed. Therefore, the advantage is obtained that the length can be easily adjusted.

An arm 104 which is a second modification of an arm component will now be described.

Figure 55:
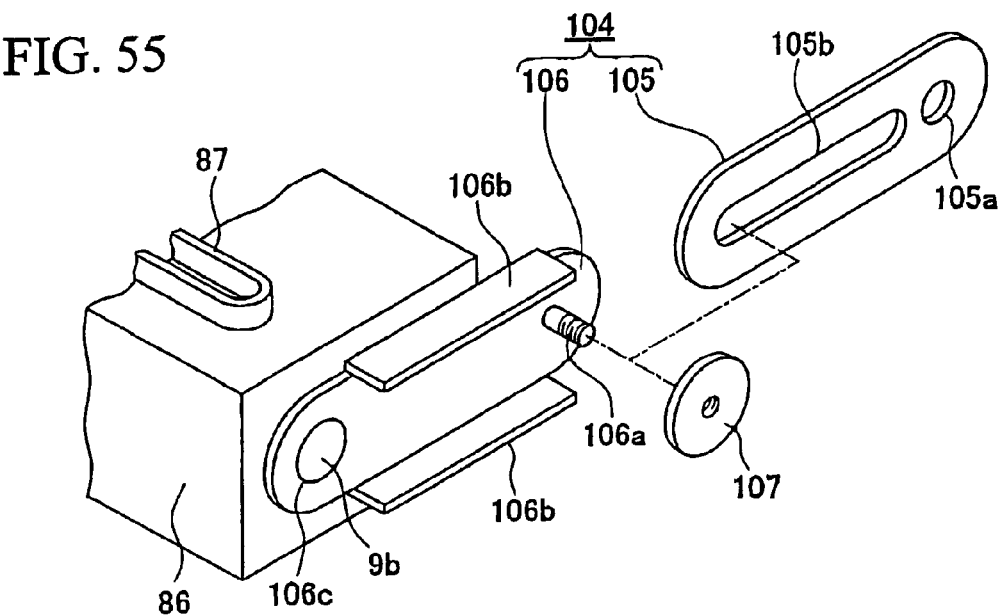
FIG. 55 is an exploded perspective view to illustrate a second modification of the arm component that is provided in the above described modification.

As is shown in FIG. 55, the arm 104 is formed by a sliding arm 105 and a fixed arm 105. The sliding arm 105 has a shaft hole 105*a* provided at one end portion in the longitudinal direction thereof that is rotatably engaged with a supporting shaft 9*a*, and a slide hole 105*b* that is provided in a center portion thereof and extends in the longitudinal direction.

The fixed arm 106 has a shaft hole 106*c* provided at one end in the longitudinal direction thereof that rotatably engages with a supporting shaft 9*b*, while a sliding shaft 106*a* that smoothly engages in the slide hole 105*b* of the sliding arm 105 and that can have a fixing nut 107 screwed onto its distal end protrudes from the other end portion of the fixed arm 106. Guide portions 106*b* that extend outwards in the direction in which the sliding shaft 106*a* protrudes are provided at the left and right in the longitudinal direction of the fixed arm 106. The width formed by the guide portions 106*b* of the fixed arm 106 is large enough to allow the transverse width of the sliding arm 105 to be able to slide along when it is fitted inside it (refer to FIG. 57).

Figure 56:
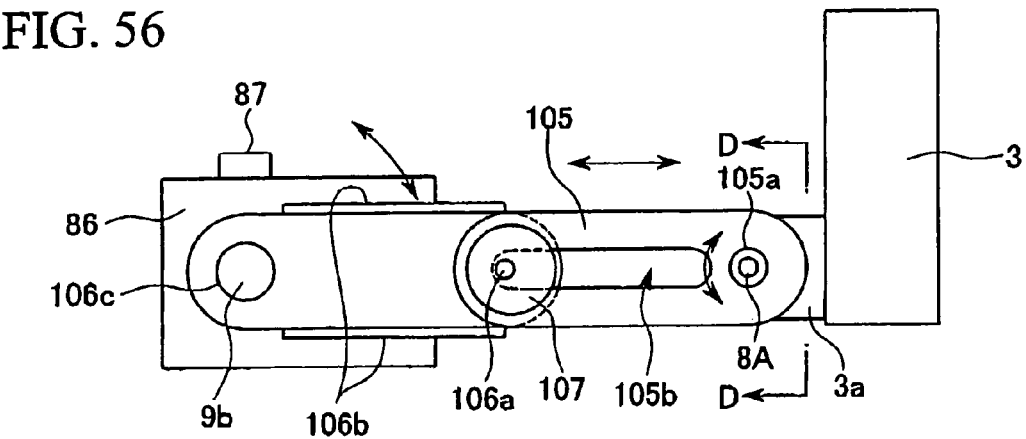
FIG. 56 is a frontal view to illustrate the second modification of the arm component that is provided in the above described modification.
Figure 57:
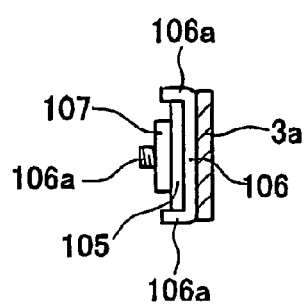
FIG. 57 is a cross-sectional view taken along a line D-D to illustrate the first modification of the arm component that is provided in the above described modification.

As is shown in FIG. 56, according to this type of arm 104, when the image display unit 3 is in a fixed state, then when the sliding shaft 106*a* has been inserted inside the slide hole 105*b*, the sliding arm 105 is held such that it is able to slide in the longitudinal direction of the fixed arn 106. By screwing the fixing nut 107 onto the sliding shaft 106*a*, the sliding arm 105 can be fixed at an appropriate length. Accordingly, when moving the image display unit 3, the image display unit 3 can be moved easily by extending the arm 104, while when fixing the position of image display unit 3, the arm 104 can be retracted to the required length. As a result, the advantage is obtained that the image display unit 3 can be stored in a compact manner. Moreover, because the sliding shaft 106*a* is fixed by screwing on the fixing nut 107, the length of the arm 104 can be reliably fixed. The advantage is thus obtained that the structure is highly resistant to impact.

Note that in the above description an example is described in which the direction of the center of rotation of the image display unit 3 is parallel with the direction of the shaft around which the bending operation lever 20 is rotated, however, provided that the image display unit 3 can be rotated to a direction where it can be easily viewed by an operator, then a center of rotation that is not parallel with the rotation shaft of the bending operation lever 20 may be used.

Moreover, in the above description an example is described in which the apparatus has a rod-shaped operating section and the direction in which the operating section extends is the same as the longitudinal direction of the gripping portion. In this apparatus, the center of rotation of the supporting portion is a direction that is orthogonal to the longitudinal direction of the gripping portion. However, any change in the orientation of the display screen achieved by changing the attitude of the grip is only relative to the longitudinal direction of the gripping portion and whether or not the entire operating section is rod shaped is irrelevant. Therefore, the shape of the operating section is not limited to being a rod shape.

Furthermore, in the above description of the modification, an example is described in which the angle of rotation of the image display unit 3 is 90 degrees, however, this is only an example, and any angle may be used.

Furthermore, in the above description of the modification, in order to simplify the explanation the L-shaped connector 82 and foot portion 83 are not shown in FIG. 47 through FIG. 51, however, the connector 82 and foot portion 83 can be positioned on the left and right side of the display unit bottom surface 38 as seen in FIG. 48 such that they do not interfere with the display unit mounting portion 86.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

The endoscope system of the present invention can be favorably used not only in the field of medicine as is described above, but also in the field of industry.

What is claimed is:

1. An endoscope system comprising:
  an endoscope that has an image pickup device that picks up an observation image of a test object;
  an image display unit that converts image pickup signals that have been sent from the image pickup device into images and then displays these images;
  a first mounting portion that is provided on an operating section of the endoscope and on which the image display unit is mounted; and
  a second mounting portion that is provided on the operating section of the endoscope and on which the image display unit is mounted in a different position from that of the first mounting portion.

2. The endoscope system according to claim 1, further comprising:
  a first output terminal that is provided on the first mounting portion and that outputs image pickup signals that have been sent from the image pickup device;
  a second output terminal that is provided on the second mounting portion and that outputs image pickup signals that have been sent from the image pickup device; and
  an input terminal that is provided on the image display unit and, when the image display unit is mounted at the first mounting portion, is connected to the first output terminal and inputs the image pickup signals into the image display unit, and, when the image display unit is mounted at the second mounting portion, is connected to the second output terminal and inputs the image pickup signals into the image display unit.

3. An endoscope system comprising:
an endoscope that has an image pickup device that picks up an observation image of a test object;
an image display unit that converts image pickup signals that have been sent from the image pickup device into images and then displays these images; and
a supporting portion that is provided on the operating section of the endoscope and that supports the image display unit such that it can be opened up from and shut against the operating section,
wherein the supporting portion includes:
a first rotation shaft that extends in a direction that intersects a side surface of the operating section and that forms a center of rotation when the image display unit is rotated; and
a second rotation shaft that extends in another direction that is perpendicular to the first rotation shaft and that forms a center of rotation when the image display unit is rotated in another direction.

4. An endoscope system comprising:
an endoscope that has anima ege pickup device that icks up an observation image of a test object;
an image display unit that converts image pickup signals that have been sent from the image pickup device into images and then displays these images; and
a supporting portion that is provided on the operating section of the endoscope and that supports the image display unit such that it can be opened up from and shut against the operating section,
wherein
the supporting portion includes:
a first rotation shaft that extends in a direction that intersects a side surface of the operating section and that forms a center of rotation when the image display unit is rotated; and
a second rotation shaft that extends in another direction that is perpendicular to the first rotation shaft and that forms a center of rotation when the image display unit is rotated in another direction, and
the supporting portion supports the image display unit such that it can be housed within a recessed portion that is provided in an outer circumferential surface of the operating section.

5. An endoscope system comprising:
an endoscope that has an image pickup device that picks up an observation image of a test object;
an image display unit that converts image pickup signals that have been sent from the image pickup device into images and then displays these images; and
a supporting portion that is provided on the operating section of the endoscope and that supports the image display unit such that it can be opened up from and shut against the operating section,
wherein the supporting portion supports the image display unit such that it can be housed within a recessed portion that is provided in an outer circumferential surface of the operating section.

6. The endoscope system according to claims 3 or 4, wherein the first rotation shaft and the second rotation shaft are each located away from the central axis of the image display unit.

7. An endoscope system comprising:
an endoscope that is provided with an image pickup device that picks up an image of a test object and a gripping portion that is formed in a longitudinal direction of the endoscope;
an image display unit that is formed integrally with the endoscope and that converts pictures of the test object that have been obtained by the image pickup device into images and then displays these images; and
a light source apparatus that is formed integrally with the endoscope and that protrudes in a symmetrically opposite direction from the image display unit with a longitudinal axis of the endoscope sandwiched in between, wherein
the image display unit is mounted so as to protrude from a side portion of the endoscope such that, when the gripping portion is gripped by a hand whose thumb is positioned uppermost, the image display unit is positioned above the fingers of the hand that is gripping the gripping portion excluding the thumb.

8. An endoscope system comprising:
an endoscope that is provided with an image pickup device that picks up an image of a test object and an operating section that operates the endoscope;
a finger piece portion that is provided so as to intersect an axis n the longitudinal direction of the operating section; and
an image display unit that is formed integrally with the finger piece portion and that converts pictures of the test object that have been obtained by the image pickup device into images and then displays these images,
wherein a rotatable operating lever is provided in the operating section, and the image display unit is provided at substantially the same position as a rotation shaft of the operating lever.

9. An endoscope system comprising:
an insertion portion that can be inserted inside a body cavity of a test object;
an observation image acquisition portion that acquires an observation image of the interior of the body cavity from a distal end side of the insertion portion;
an operating section that is connected to a base end portion of the insertion portion;
an observation portion that is provided in the operating section and that makes it possible to observe the observation images that have been acquired by the observation image acquisition portion; and
three setting down portions that are arranged in a triangle extending across at least one of the operating section and the observation portion.

10. The endoscope system according to claim 9, wherein at least one of the setting down portions is formed by a connector component that is used for connecting an external cable and is provided so as to protrude from the observation portion or the operating section.

11. An endoscope system comprising:
an insertion portion that can be inserted inside a body cavity of a test object;
an observation image acquisition portion that acquires an observation image of the interior of the body cavity from a distal end side of the insertion portion;
an image pickup device that picks up the observation images;
an image display unit that includes a display screen that displays observation images based on image pickup signals from the image pickup device;

an operating section that is provided with a gripping portion and that is connected to a base end portion of the insertion portion; and a supporting portion that is provided in the operating section and rotatably supports the image display unit, wherein the display screen can be rotated around an axis that intersects a longitudinal direction of the gripping portion.

12. The endoscope system according to claim 11, wherein the operating section is provided with an operating component that controls movements of the insertion portion, and, in the gripping portion, the operating component can be operated by an operator when the operator is gripping the gripping portion, and, in the image display unit, when the operator is gripping the gripping portion the display screen can be rotated so as to face towards the operator.

13. The endoscope system according to claim 11, wherein the supporting portion is provided with: a first rotation supporting portion that is provided on the operating section; a second rotation supporting portion that is provided on the image display unit; and an arm component that is rotatably linked to both the first rotation supporting portion and the second rotation supporting portion.

* * * * *